US012655115B2

(12) United States Patent
Andreae

(10) Patent No.: US 12,655,115 B2
(45) Date of Patent: Jun. 16, 2026

(54) SYNTHESIS OF PROSTATE SPECIFIC MEMBRANE ANTIGEN (PSMA) LIGANDS

(71) Applicant: NOVARTIS AG, Basel (CH)

(72) Inventor: Fritz Andreae, Raaba-Grambach (AT)

(73) Assignee: NOVARTIS AG, Basel (CH)

( * ) Notice: Subject to any disclaimer, the term of this patent is extended or adjusted under 35 U.S.C. 154(b) by 480 days.

(21) Appl. No.: 18/253,306

(22) PCT Filed: Nov. 19, 2021

(86) PCT No.: PCT/EP2021/082323
§ 371 (c)(1),
(2) Date: May 17, 2023

(87) PCT Pub. No.: WO2022/106629
PCT Pub. Date: May 27, 2022

(65) Prior Publication Data

US 2024/0025866 A1 Jan. 25, 2024

(30) Foreign Application Priority Data

Nov. 19, 2020 (EP) .................................... 20208556

(51) Int. Cl.
*C07D 257/02* (2006.01)

(52) U.S. Cl.
CPC ................................ *C07D 257/02* (2013.01)

(58) Field of Classification Search
CPC .................................................. C07D 257/02
USPC ......................................................... 540/474
See application file for complete search history.

(56) References Cited

U.S. PATENT DOCUMENTS

| | | | |
|---|---|---|---|
| 4,691,024 | A | 9/1987 | Shirahata |
| 4,713,249 | A | 12/1987 | Schroeder |
| 5,103,018 | A | 4/1992 | Motomichi |
| 5,266,333 | A | 11/1993 | Cady |
| 5,417,982 | A | 5/1995 | Modi |
| 5,418,982 | A | 5/1995 | Kishi |
| 5,627,165 | A | 5/1997 | Glazier |
| 5,795,877 | A | 8/1998 | Jackson |
| 5,863,536 | A | 1/1999 | Jackson |
| 5,866,679 | A | 2/1999 | DeFeo-Jones |
| 5,902,817 | A | 5/1999 | Jackson |
| 5,948,750 | A | 9/1999 | Garsky |
| 5,962,237 | A | 10/1999 | Ts'o |
| 5,962,521 | A | 10/1999 | Jackson |
| 5,968,915 | A | 10/1999 | Jackson |
| 5,998,362 | A | 12/1999 | Feng |
| 6,054,444 | A | 4/2000 | Jackson |
| 6,127,333 | A | 10/2000 | Brady |
| 6,174,858 | B1 | 1/2001 | Brady |
| 6,177,404 | B1 | 1/2001 | Defeo-Jones |
| 6,183,721 | B1 | 2/2001 | Albert |
| 6,232,287 | B1 | 5/2001 | Ruoslahti |
| 6,368,598 | B1 | 4/2002 | D'Amico |
| 6,391,305 | B1 | 5/2002 | Feng |
| 6,428,785 | B1 | 8/2002 | Gokcen |
| 6,479,470 | B1 | 11/2002 | Kozikowski |
| 6,528,499 | B1 | 3/2003 | Kozikowski |
| 6,692,724 | B1 | 2/2004 | Yang |
| 6,875,886 | B2 | 4/2005 | Frangioni |
| 6,946,133 | B1 | 9/2005 | Schlom |
| 7,008,765 | B1 | 3/2006 | Bussemakers |
| 7,128,893 | B2 | 10/2006 | Leamon |
| 7,129,254 | B2 | 10/2006 | Berger |
| 7,147,837 | B2 | 12/2006 | Lauffer |
| 7,192,586 | B2 | 3/2007 | Bander |
| 7,226,577 | B2 | 6/2007 | Cappelletti |
| 7,232,805 | B2 | 6/2007 | Weinshenker |
| 7,361,338 | B2 | 4/2008 | Jakobovits |
| 7,381,745 | B2 | 6/2008 | Kozikowski |
| 7,399,460 | B2 | 7/2008 | Wedeking |
| 7,408,079 | B2 | 8/2008 | Pomper |
| 7,485,299 | B2 | 2/2009 | Afar |
| 7,514,078 | B2 | 4/2009 | Bander |
| 7,517,903 | B2 | 4/2009 | Chen |
| 7,534,580 | B2 | 5/2009 | Reeves |
| 7,601,332 | B2 | 10/2009 | Vlahov |
| 7,635,682 | B2 | 12/2009 | Denmeade |
| 7,638,122 | B2 | 12/2009 | Yu |
| 7,659,395 | B2 | 2/2010 | Pajouhesh |
| 7,662,795 | B2 | 2/2010 | Rodriguez |
| 7,696,185 | B2 | 4/2010 | Berkman |
| 7,713,944 | B2 | 5/2010 | Kinberger |
| 7,740,847 | B2 | 6/2010 | Allan |
| 7,767,202 | B2 | 8/2010 | Pardoll |
| 7,767,803 | B2 | 8/2010 | Diener |

(Continued)

FOREIGN PATENT DOCUMENTS

| | | |
|---|---|---|
| AU | 2008289108 B2 | 9/2014 |
| AU | 2014348601 A1 | 5/2016 |

(Continued)

OTHER PUBLICATIONS

PCT Search Report and Written Opinion prepared for PCT Application No. PCT/EP2021/082323, completed Dec. 13, 2021.
Pratesi, Alessandro, et al., "Design and Solid Phase Synthesis of new DOTA Conjugated (+)-Biotin Dimers Planned to Develop Molecular Weight-Tuned Avidin Oligomers," 2015, Org. Biomol Chem., vol. 13, pp. 3988-4001.
Banerjee, Sangeeta Ray, et al., "Effect of Chelators on the Pharmacokinetics of 99mTc-Labeled Imaging Agents for the Prostate-Specific Membrane Antigen (PSMA)," 2013, J. Med Chem., vol. 56, No. 15, pp. 6108-6121.
Chan WC et al. "Fmoc-Solid Phase Peptide Synthesis—A practical approach passage", Mar. 1, 2000 (Mar. 1, 2000), FMOC Solid Phase Peptide Synthesis : A Practical Approach; [The Practical Approach Series , ISSN 0957-025X ; ZDB-10: 9132715 ; 222], Oxford University Press, GB, pp. X-XXIV.

(Continued)

*Primary Examiner* — Kristin A Vajda
(74) *Attorney, Agent, or Firm* — Barnes & Thornburg LLP

(57) ABSTRACT

The present disclosure relates to the synthesis of prostate specific membrane antigen (PSMA) ligands that are useful in the treatment of diseases like cancer. In particular, the disclosure relates to a method for synthesizing PSMA ligands having a glutamate-urea-lysine (GUL) moiety and a chelating agent that can comprise a radiometal.

12 Claims, 1 Drawing Sheet

(56) References Cited

U.S. PATENT DOCUMENTS 7,794,929 B2 9/2010 Baylin
7,862,798 B2 1/2011 Leamon
7,872,235 B2 1/2011 Rousso
7,875,586 B2 1/2011 Kovbasnjuk
7,879,981 B2 2/2011 Obata
7,910,594 B2 3/2011 Vlahov
RE42,275 E 4/2011 Berkman
7,990,533 B2 8/2011 Maier
8,000,773 B2 8/2011 Rousso
8,101,369 B2 1/2012 Nam
8,101,713 B2 1/2012 Cuello
8,105,568 B2 1/2012 Vlahov
8,153,595 B2 4/2012 Chen
8,211,401 B2 7/2012 Babich
8,211,402 B2 7/2012 Babich
8,211,473 B2 7/2012 Troiano
8,211,635 B2 7/2012 Barton
8,227,634 B2 7/2012 Pomper
8,236,330 B2 8/2012 Zale
8,246,968 B2 8/2012 Zale
8,258,111 B2 9/2012 Shen
8,273,363 B2 9/2012 Zale
8,313,128 B2 11/2012 Belyea
8,313,728 B2 11/2012 Leamon
8,388,977 B2 3/2013 Low
8,404,817 B2 3/2013 Sherman
8,414,898 B2 4/2013 Afar
8,445,851 B2 5/2013 Rousso
8,450,290 B2 5/2013 Worm
8,465,725 B2 6/2013 Babich
8,487,128 B2 7/2013 Weissbach
8,487,129 B2 7/2013 Babich
8,507,434 B2 8/2013 Popel
8,557,772 B2 10/2013 Popel
8,562,945 B2 10/2013 Babich
8,603,499 B2 12/2013 Zale
8,603,500 B2 12/2013 Zale
8,603,501 B2 12/2013 Zale
8,606,349 B2 12/2013 Rousso
8,644,910 B2 2/2014 Rousso
8,685,891 B2 4/2014 Muraca
8,703,918 B2 4/2014 Colombatti
8,709,483 B2 4/2014 Farokhzad
8,772,226 B2 7/2014 Denmeade
8,772,459 B2 7/2014 Ho
8,778,305 B2 7/2014 Pomper
8,802,153 B2 8/2014 Cheng
8,816,095 B2 8/2014 Brown
8,834,842 B2 9/2014 Leamon
8,840,865 B2 9/2014 Babich
8,852,630 B2 10/2014 Spiegel
8,859,509 B2 10/2014 Spiegel
8,865,126 B2 10/2014 Leamon
8,865,875 B2 10/2014 Liu
8,877,970 B2 11/2014 Zimmerman
8,901,294 B2 12/2014 Kim
8,907,058 B2 12/2014 Low
8,916,161 B2 12/2014 Buckley
8,916,167 B2 12/2014 Low
8,926,944 B2 1/2015 Babich
8,926,945 B2 1/2015 Port
8,940,871 B2 1/2015 Wu
8,946,388 B2 2/2015 Sahin
8,962,799 B2 2/2015 Babich
8,986,655 B2 3/2015 Weiss
8,987,319 B2 3/2015 Miller
9,044,468 B2 6/2015 Pomper
9,056,841 B2 6/2015 Pomper
9,193,763 B2 11/2015 Low
9,226,981 B2 1/2016 Pomper
9,242,012 B2 1/2016 Ma
9,278,067 B2 3/2016 Boulikas
9,295,727 B2 3/2016 Zale
9,309,193 B2 4/2016 Babich
9,629,918 B2 4/2017 Low
9,636,413 B2 5/2017 Vlahov
9,687,572 B2 6/2017 Babich
9,782,493 B2 10/2017 Vlahov
9,801,956 B2 10/2017 Kularatne
9,808,538 B2 11/2017 Kularatne
9,951,324 B2 4/2018 Low
9,968,691 B2 5/2018 Kularatne
10,046,054 B2 8/2018 Low
10,188,759 B2 1/2019 Vlahov
10,308,606 B2 6/2019 Kularatne
10,363,388 B2 7/2019 Fonseca
10,398,791 B2 9/2019 Eder
10,406,238 B2 9/2019 Low
10,406,240 B2 9/2019 Low
10,456,482 B2 10/2019 Kularatne
10,471,160 B2 11/2019 Eder
10,485,878 B2 11/2019 Low
10,517,956 B2 12/2019 Low
10,517,957 B2 12/2019 Low
10,557,128 B2 2/2020 Low
10,624,969 B2 4/2020 Low
10,624,970 B2 4/2020 Low
10,624,971 B2 4/2020 Low
10,646,581 B2 5/2020 Low
10,688,200 B2 6/2020 Kung
10,828,282 B2 11/2020 Low
10,842,887 B2 11/2020 Kularatne
10,898,596 B2 1/2021 Vlahov
10,912,840 B2 2/2021 Vlahov
11,045,564 B2 6/2021 Eder
11,083,710 B2 8/2021 Low
11,155,800 B2 10/2021 Low
11,298,341 B2 4/2022 Low
11,318,121 B2 5/2022 Low
11,369,590 B2 6/2022 Low
11,484,607 B2 11/2022 Kularatne
11,504,357 B2 11/2022 Low
11,717,514 B2 8/2023 Low
11,931,430 B2 3/2024 Eder
11,951,190 B2 4/2024 Eder
12,091,693 B2 9/2024 Low
12,133,900 B2 11/2024 Low
12,178,892 B2 12/2024 Vlahov
12,208,102 B2 1/2025 Armour
2001/0031252 A1 10/2001 Low
2002/0001782 A1 1/2002 Watanabe
2002/0055121 A1 5/2002 Vielkind
2002/0103136 A1 8/2002 Feng
2002/0115596 A1 8/2002 Garsky
2002/0132983 A1 9/2002 Junghans
2003/0035804 A1 2/2003 D'Amico
2003/0086900 A1 5/2003 Low
2003/0133927 A1 7/2003 Defeo-Jones
2003/0138432 A1 7/2003 Glazier
2003/0207808 A1 11/2003 Savitzky
2003/0215456 A1 11/2003 Yao
2003/0220241 A1 11/2003 Defeo-Jones
2003/0232760 A1 12/2003 Garsky
2004/0001846 A1 1/2004 Israeli
2004/0002478 A1 1/2004 Kozikowski
2004/0018203 A1 1/2004 Pastan
2004/0029778 A1 2/2004 Isaacs
2004/0033195 A1 2/2004 Leamon
2004/0052727 A1 3/2004 Dalton
2004/0054190 A1 3/2004 Pomper
2004/0058857 A1 3/2004 Yao
2004/0092890 A1 5/2004 Ash
2004/0110723 A1 6/2004 Frangioni
2004/0146516 A1 7/2004 Roben
2004/0213791 A1 10/2004 Bander
2004/0229845 A1 11/2004 Frangioni
2004/0242582 A1 12/2004 Green
2005/0002942 A1 1/2005 Vlahov
2005/0085417 A1 4/2005 Wickstrom
2005/0107325 A1 5/2005 Manoharan
2005/0119166 A1 6/2005 Brady
2005/0158780 A1 7/2005 Lupold
2005/0234247 A1 10/2005 Klar
2005/0239138 A1 10/2005 Hess

(56) References Cited

U.S. PATENT DOCUMENTS

| | | | |
|---|---|---|---|
| 2005/0239739 | A1 | 10/2005 | Matulic-Adamic |
| 2005/0245486 | A1 | 11/2005 | Frangioni |
| 2005/0255042 | A1 | 11/2005 | Lam |
| 2006/0024317 | A1 | 2/2006 | Boyd |
| 2006/0052312 | A1 | 3/2006 | Erhardt |
| 2006/0062793 | A1 | 3/2006 | Webb |
| 2006/0105975 | A1 | 5/2006 | Pendergrast |
| 2006/0106047 | A1 | 5/2006 | Jiang |
| 2006/0140871 | A1 | 6/2006 | Sillerud |
| 2006/0148718 | A1 | 7/2006 | Brady |
| 2006/0155021 | A1 | 7/2006 | Lenges |
| 2006/0155146 | A1 | 7/2006 | Lenges |
| 2007/0010014 | A1 | 1/2007 | Wood |
| 2007/0020177 | A1 | 1/2007 | McGill |
| 2007/0020327 | A1 | 1/2007 | Fikes |
| 2007/0031326 | A1 | 2/2007 | Shirvan |
| 2007/0031438 | A1 | 2/2007 | Junghans |
| 2007/0041901 | A1 | 2/2007 | Diener |
| 2007/0117153 | A1 | 5/2007 | Bieniarz |
| 2007/0128670 | A1 | 6/2007 | Klatzmann |
| 2007/0134332 | A1 | 6/2007 | Turnell |
| 2007/0142296 | A1 | 6/2007 | Mcbride |
| 2007/0148662 | A1 | 6/2007 | Israeli |
| 2007/0160617 | A1 | 7/2007 | Ma |
| 2007/0172422 | A1 | 7/2007 | Glazier |
| 2007/0179100 | A1 | 8/2007 | Manoharan |
| 2007/0201277 | A1 | 8/2007 | Nam |
| 2007/0219165 | A1 | 9/2007 | Berkman |
| 2007/0225213 | A1 | 9/2007 | Kosak |
| 2007/0244055 | A1 | 10/2007 | Brady |
| 2007/0254316 | A1 | 11/2007 | Rodriguez |
| 2007/0254317 | A1 | 11/2007 | Busseret-Michel |
| 2007/0280880 | A1 | 12/2007 | Moser |
| 2008/0008649 | A1 | 1/2008 | Cappelletti |
| 2008/0008719 | A1 | 1/2008 | Bowdish |
| 2008/0089842 | A1 | 4/2008 | Pagel |
| 2008/0089869 | A1 | 4/2008 | Denmeade |
| 2008/0114153 | A1 | 5/2008 | Steeves |
| 2008/0175789 | A1 | 7/2008 | Frangioni |
| 2008/0176821 | A1 | 7/2008 | Kozikowski |
| 2008/0193381 | A1 | 8/2008 | Babich |
| 2008/0214436 | A1 | 9/2008 | Yu |
| 2008/0248052 | A1 | 10/2008 | Vlahov |
| 2008/0269105 | A1 | 10/2008 | Taft |
| 2008/0311037 | A1 | 12/2008 | Heston |
| 2009/0061010 | A1 | 3/2009 | Zale |
| 2009/0117042 | A1 | 5/2009 | Pomper |
| 2009/0123467 | A1 | 5/2009 | Bedi |
| 2009/0180951 | A1 | 7/2009 | Zimmerman |
| 2009/0214636 | A1 | 8/2009 | Low |
| 2009/0247614 | A1 | 10/2009 | Manoharan |
| 2009/0258002 | A1 | 10/2009 | Barrett |
| 2009/0274625 | A1 | 11/2009 | Denmeade |
| 2010/0032400 | A1 | 2/2010 | James |
| 2010/0048490 | A1 | 2/2010 | Vlahov |
| 2010/0055735 | A1 | 3/2010 | Low |
| 2010/0092496 | A1 | 4/2010 | Boyd |
| 2010/0178246 | A1 | 7/2010 | Babich |
| 2010/0183509 | A1 | 7/2010 | Babich |
| 2010/0183517 | A1 | 7/2010 | Berkman |
| 2010/0209343 | A1 | 8/2010 | Bander |
| 2010/0234450 | A1 | 9/2010 | Schultz |
| 2010/0240701 | A1 | 9/2010 | Vlahov |
| 2010/0324008 | A1 | 12/2010 | Low |
| 2011/0008253 | A1 | 1/2011 | Babich |
| 2011/0027180 | A1 | 2/2011 | Magnani |
| 2011/0027274 | A1 | 2/2011 | Cheng |
| 2011/0064657 | A1 | 3/2011 | Pomper |
| 2011/0142760 | A1 | 6/2011 | Pomper |
| 2011/0172254 | A1 | 7/2011 | Leamon |
| 2011/0176998 | A1 | 7/2011 | Pomper |
| 2011/0200677 | A1 | 8/2011 | Chandran |
| 2011/0256157 | A1 | 10/2011 | Howard |
| 2011/0288152 | A1 | 11/2011 | Low |
| 2012/0009121 | A1 | 1/2012 | Pomper |
| 2012/0269726 | A1 | 10/2012 | Babich |
| 2012/0276007 | A1 | 11/2012 | Pomper |
| 2012/0276162 | A1 | 11/2012 | Zale |
| 2012/0322741 | A1 | 12/2012 | Low |
| 2013/0034494 | A1 | 2/2013 | Babich |
| 2013/0172406 | A1 | 7/2013 | Zale |
| 2013/0315821 | A1 | 11/2013 | D'Souza |
| 2013/0336888 | A1 | 12/2013 | Babich |
| 2014/0073763 | A1 | 3/2014 | Low |
| 2014/0107316 | A1 | 4/2014 | Vlahov |
| 2014/0140925 | A1 | 5/2014 | Leamon |
| 2014/0154702 | A1 | 6/2014 | Parker |
| 2014/0187501 | A1 | 7/2014 | Bilodeau |
| 2014/0228541 | A1 | 8/2014 | D'Souza |
| 2014/0314864 | A1 | 10/2014 | Cheng |
| 2015/0023875 | A1 | 1/2015 | Farokhzad |
| 2015/0079001 | A1 | 3/2015 | Pomper |
| 2015/0104387 | A1 | 4/2015 | Pomper |
| 2015/0110715 | A1 | 4/2015 | Eder |
| 2015/0110814 | A1 | 4/2015 | Olson |
| 2015/0246144 | A1 | 9/2015 | Pomper |
| 2015/0297735 | A1 | 10/2015 | Vlahov |
| 2015/0315196 | A1 | 11/2015 | Howard |
| 2015/0366968 | A1 | 12/2015 | Basilion |
| 2016/0045626 | A1 | 2/2016 | Mcbride |
| 2016/0067341 | A1 | 3/2016 | Low |
| 2016/0074526 | A1 | 3/2016 | Bilodeau |
| 2016/0114060 | A1 | 4/2016 | Pomper |
| 2016/0151508 | A1 | 6/2016 | Low |
| 2016/0208021 | A1 | 7/2016 | Chang |
| 2016/0220694 | A1 | 8/2016 | Vlahov |
| 2016/0228587 | A1 | 8/2016 | Eder |
| 2016/0256578 | A1 | 9/2016 | Tsukada |
| 2016/0256579 | A1 | 9/2016 | Shalom |
| 2016/0287731 | A1 | 10/2016 | Vlahov |
| 2016/0361376 | A1 | 12/2016 | Vlahov |
| 2016/0361432 | A1 | 12/2016 | Vlahov |
| 2016/0361433 | A1 | 12/2016 | Vlahov |
| 2017/0226141 | A1 | 8/2017 | Slusher |
| 2017/0258923 | A1 | 9/2017 | Low |
| 2017/0258932 | A1 | 9/2017 | Vlahov |
| 2018/0027190 | A1 | 1/2018 | Srinivasan |
| 2018/0207298 | A1 | 7/2018 | Berkman |
| 2018/0243431 | A1 | 8/2018 | Low |
| 2018/0256733 | A1 | 9/2018 | Vlahov |
| 2018/0256734 | A1 | 9/2018 | Vlahov |
| 2018/0256735 | A1 | 9/2018 | Vlahov |
| 2018/0256736 | A1 | 9/2018 | Vlahov |
| 2018/0256737 | A1 | 9/2018 | Vlahov |
| 2018/0271988 | A1 | 9/2018 | Low |
| 2018/0271989 | A1 | 9/2018 | Low |
| 2018/0271990 | A1 | 9/2018 | Low |
| 2018/0271991 | A1 | 9/2018 | Vlahov |
| 2018/0289826 | A1 | 10/2018 | Vlahov |
| 2018/0289827 | A1 | 10/2018 | Low |
| 2018/0289828 | A1 | 10/2018 | Low |
| 2018/0289829 | A1 | 10/2018 | Low |
| 2018/0303950 | A1 | 10/2018 | Low |
| 2018/0339071 | A1 | 11/2018 | Jeong |
| 2018/0346008 | A1 | 12/2018 | Nahum |
| 2019/0177345 | A1 | 6/2019 | Larsen |
| 2019/0314515 | A1 | 10/2019 | Vlahov |
| 2019/0389951 | A1 | 12/2019 | Murphy |
| 2020/0155695 | A1 | 5/2020 | Low |
| 2020/0155696 | A1 | 5/2020 | Low |
| 2020/0188523 | A1 | 6/2020 | Low |
| 2020/0261592 | A1 | 8/2020 | Low |
| 2020/0297701 | A1 | 9/2020 | Low |
| 2021/0077468 | A1 | 3/2021 | Low |
| 2021/0154311 | A1 | 5/2021 | Vlahov |
| 2021/0154312 | A1 | 5/2021 | Vlahov |
| 2021/0161911 | A1 | 6/2021 | Armour |
| 2021/0177996 | A1 | 6/2021 | Eder |
| 2021/0283279 | A1 | 9/2021 | Eder |
| 2021/0322388 | A1 | 10/2021 | Low |
| 2021/0323985 | A1 | 10/2021 | Leamon |
| 2021/0338641 | A1 | 11/2021 | Low |
| 2022/0096445 | A1 | 3/2022 | Low |
| 2022/0098564 | A1 | 3/2022 | Low |

(56) References Cited

U.S. PATENT DOCUMENTS

| | | | |
|---|---|---|---|
| 2022/0125957 | A1 | 4/2022 | Armour |
| 2022/0125958 | A1 | 4/2022 | Vlahov |
| 2022/0220085 | A1 | 7/2022 | Vlahov |
| 2022/0265841 | A1 | 8/2022 | Vlahov |
| 2023/0000836 | A1 | 1/2023 | Low |
| 2023/0098279 | A1 | 3/2023 | Leamon |
| 2023/0346752 | A1 | 11/2023 | Low |
| 2024/0181092 | A1 | 6/2024 | Catafau |
| 2024/0350680 | A1 | 10/2024 | Eder |
| 2024/0382631 | A1 | 11/2024 | Eder |
| 2025/0108039 | A1 | 4/2025 | Low |
| 2025/0127939 | A1 | 4/2025 | Vlahov |
| 2025/0170253 | A1 | 5/2025 | Vlahov |

FOREIGN PATENT DOCUMENTS

| | | | |
|---|---|---|---|
| CA | 2606138 | A1 | 10/2005 |
| CA | 2696627 | A1 | 2/2009 |
| CA | 2696627 | A | 9/2016 |
| CA | 2696627 | C | 9/2016 |
| CN | 1662263 | A | 8/2005 |
| CN | 1761488 | | 4/2006 |
| CN | 100528241 | | 8/2009 |
| CN | 101568352 | | 10/2009 |
| CN | 101678118 | | 3/2010 |
| CN | 101863924 | A | 10/2010 |
| CN | 102014956 | A | 4/2011 |
| CN | 103951668 | A | 7/2014 |
| CN | 104873982 | A | 9/2015 |
| CN | 105636924 | | 6/2016 |
| CN | 109134602 | | 1/2019 |
| CN | 111801121 | A | 10/2020 |
| CN | 109134602 | B | 7/2021 |
| DE | 202014008232 | U1 | 3/2015 |
| EP | 0116208 | | 8/1984 |
| EP | 0116208 | B1 | 3/1988 |
| EP | 1177200 | | 2/2002 |
| EP | 1472541 | | 11/2004 |
| EP | 1177200 | B1 | 6/2005 |
| EP | 1999136 | | 12/2008 |
| EP | 2097111 | | 9/2009 |
| EP | 2136788 | | 12/2009 |
| EP | 2170075 | | 4/2010 |
| EP | 2187965 | | 5/2010 |
| EP | 2240171 | | 10/2010 |
| EP | 2318366 | | 5/2011 |
| EP | 2136788 | B1 | 10/2011 |
| EP | 2373621 | A2 | 10/2011 |
| EP | 2389361 | | 11/2011 |
| EP | 2408755 | | 1/2012 |
| EP | 2436376 | | 4/2012 |
| EP | 2567711 | | 3/2013 |
| EP | 2644192 | | 10/2013 |
| EP | 2644594 | | 10/2013 |
| EP | 2648766 | | 10/2013 |
| EP | 2706057 | | 3/2014 |
| EP | 2436376 | B1 | 7/2014 |
| EP | 2759535 | A1 | 7/2014 |
| EP | 2170075 | B1 | 12/2014 |
| EP | 2823826 | A2 | 1/2015 |
| EP | 2097111 | B1 | 7/2015 |
| EP | 2921482 | | 9/2015 |
| EP | 2938364 | A1 | 11/2015 |
| EP | 2942065 | | 11/2015 |
| EP | 2958596 | | 12/2015 |
| EP | 2993171 | A1 | 3/2016 |
| EP | 2706057 | B1 | 4/2016 |
| EP | 3038996 | | 7/2016 |
| EP | 2389361 | B1 | 8/2016 |
| EP | 3116208 | | 1/2017 |
| EP | 2318366 | B1 | 5/2017 |
| EP | 2408755 | B1 | 5/2017 |
| EP | 2644192 | B1 | 5/2017 |
| EP | 2644594 | B1 | 8/2017 |
| EP | 2648766 | B1 | 4/2018 |
| EP | 2942065 | B1 | 6/2018 |
| EP | 2921482 | B1 | 9/2018 |
| EP | 3388086 | | 10/2018 |
| EP | 2187965 | B1 | 10/2019 |
| EP | 2958596 | B1 | 12/2019 |
| EP | 3038996 | B1 | 6/2022 |
| IL | 203998 | A | 8/2015 |
| JP | 2002506204 | A | 2/2002 |
| JP | 3596479 | | 12/2004 |
| JP | 2004536034 | A | 12/2004 |
| JP | 3625690 | | 3/2005 |
| JP | 2005274569 | A | 10/2005 |
| JP | 2006501149 | A | 1/2006 |
| JP | 2006514961 | A | 5/2006 |
| JP | 2006518712 | A | 8/2006 |
| JP | 2007521803 | A | 8/2007 |
| JP | 2009519209 | A | 5/2009 |
| JP | 2010515732 | A | 5/2010 |
| JP | 2010518112 | A | 5/2010 |
| JP | 2010531363 | | 9/2010 |
| JP | 2010532754 | A | 10/2010 |
| JP | 2010536790 | A | 12/2010 |
| JP | 2010540535 | | 12/2010 |
| JP | 2011132258 | A | 7/2011 |
| JP | 2012511023 | A | 5/2012 |
| JP | 2014221779 | A | 11/2014 |
| JP | 5902237 | B2 | 4/2016 |
| JP | 2016153410 | A | 8/2016 |
| JP | 2016535013 | A | 11/2016 |
| JP | 2017530109 | A5 | 10/2017 |
| JP | 2018058847 | A | 4/2018 |
| JP | 2018150350 | A | 9/2018 |
| JP | 2019503919 | A | 2/2019 |
| JP | 6596479 | B2 | 10/2019 |
| JP | 6625690 | B2 | 12/2019 |
| JP | 2020073472 | A | 5/2020 |
| JP | 2020530007 | A | 10/2020 |
| KR | 20030031905 | A | 4/2003 |
| PH | 12016500656 | A | 6/2016 |
| RU | 2004136995 | A | 7/2005 |
| RU | 2404193 | C2 | 11/2010 |
| WO | 1988001622 | A1 | 3/1988 |
| WO | 1991007418 | A1 | 5/1991 |
| WO | 1995033766 | A1 | 12/1995 |
| WO | 1999045374 | | 9/1999 |
| WO | 2000001419 | | 1/2000 |
| WO | 2000064911 | A1 | 11/2000 |
| WO | 2000066091 | A1 | 11/2000 |
| WO | 2001091807 | A2 | 12/2001 |
| WO | 2002043773 | | 6/2002 |
| WO | 02062398 | | 8/2002 |
| WO | 2002098885 | A1 | 12/2002 |
| WO | 03000201 | | 1/2003 |
| WO | 2003060523 | A1 | 7/2003 |
| WO | 2003092742 | A1 | 11/2003 |
| WO | 2003097105 | A1 | 11/2003 |
| WO | 2003097647 | A1 | 11/2003 |
| WO | 2004010957 | A2 | 2/2004 |
| WO | 2004069159 | A2 | 8/2004 |
| WO | 2004069285 | A1 | 8/2004 |
| WO | WO2005023314 | | 3/2005 |
| WO | 2005082023 | A2 | 9/2005 |
| WO | 2005112919 | A2 | 12/2005 |
| WO | 2006012527 | A1 | 2/2006 |
| WO | 2006093991 | A1 | 9/2006 |
| WO | 2006096754 | A2 | 9/2006 |
| WO | 2006104911 | A2 | 10/2006 |
| WO | 2006136564 | A1 | 12/2006 |
| WO | 2007006041 | A2 | 1/2007 |
| WO | 2007022493 | A2 | 2/2007 |
| WO | 2007022494 | A2 | 2/2007 |
| WO | 2007042504 | A2 | 4/2007 |
| WO | 2007106869 | A1 | 9/2007 |
| WO | 2008057437 | A2 | 5/2008 |
| WO | 2008058192 | A2 | 5/2008 |
| WO | 2008088648 | A2 | 7/2008 |
| WO | 2008098112 | A2 | 8/2008 |
| WO | 2008101231 | A2 | 8/2008 |
| WO | 2008121949 | A1 | 10/2008 |

(56) References Cited

FOREIGN PATENT DOCUMENTS

| | | | |
|---|---|---|---|
| WO | 2009002529 | A2 | 12/2008 |
| WO | 2009002993 | A1 | 12/2008 |
| WO | 2009026177 | A1 | 2/2009 |
| WO | 2009070302 | A1 | 6/2009 |
| WO | 2009079024 | A1 | 6/2009 |
| WO | 2009082606 | A2 | 7/2009 |
| WO | 2009089383 | A2 | 7/2009 |
| WO | 2010014933 | A2 | 2/2010 |
| WO | 2010065899 | A2 | 6/2010 |
| WO | 2010065902 | A2 | 6/2010 |
| WO | 2010065906 | A2 | 6/2010 |
| WO | 2010108125 | A2 | 9/2010 |
| WO | 2011014821 | A1 | 2/2011 |
| WO | 2011017249 | A1 | 2/2011 |
| WO | 2011106639 | A1 | 9/2011 |
| WO | 2011108125 | A2 | 9/2011 |
| WO | 2012078534 | A1 | 6/2012 |
| WO | 2012166923 | A2 | 12/2012 |
| WO | 2012174136 | A1 | 12/2012 |
| WO | 2013022797 | A1 | 2/2013 |
| WO | 2013028664 | A1 | 2/2013 |
| WO | 2013130776 | A1 | 9/2013 |
| WO | 2014062697 | A2 | 4/2014 |
| WO | 2014078484 | A1 | 5/2014 |
| WO | 2014106208 | A1 | 7/2014 |
| WO | 2014127365 | A1 | 8/2014 |
| WO | 2014134543 | A1 | 9/2014 |
| WO | 2015027205 | A1 | 2/2015 |
| WO | 2015055318 | A1 | 4/2015 |
| WO | 2015057250 | A1 | 4/2015 |
| WO | 2015171792 | A1 | 11/2015 |
| WO | 2016030329 | A1 | 3/2016 |
| WO | 2016040179 | A1 | 3/2016 |
| WO | 2017089515 | A1 | 6/2017 |
| WO | 2017116994 | A1 | 7/2017 |
| WO | 2017117687 | | 7/2017 |
| WO | 2018031507 | A1 | 2/2018 |
| WO | 2018108287 | A1 | 6/2018 |
| WO | 2018187791 | A1 | 10/2018 |
| WO | 2018191376 | A2 | 10/2018 |
| WO | WO2018223180 | | 12/2018 |
| WO | 2019115684 | A1 | 6/2019 |
| WO | 2019165200 | A1 | 8/2019 |
| WO | 2019204335 | A1 | 10/2019 |
| WO | 2020061293 | A1 | 3/2020 |
| WO | WO2020236808 | | 11/2020 |

OTHER PUBLICATIONS

Delker, Andreas, et al., "Dosimetry for 177Lu-DKFZ-PSMA-617: a New Radiopharmaceutical for the Treatment of Metastatic Prostate Cancer," 2016, European Journal of Nuclear Medicine and Molecular Imaging, vol. 43, No. 1, pp. 42-51.

Kiess, A. P., et al., "Prostate-Specific Membrane Antigen as a Target for Cancer Imaging and Therapy," 2015, Q J Nucl Med Mol Imaging., vol. 59, No. 3, pp. 241-268.

Benesova, Martina, et al., "Preclinical Evaluation of a Tailor-Made DOTA-Conjugated PSMA Inhibitor with Optimized Linker Moiety for Imaging and Endoradiotherapy of Prostate Cancer," 2015, J. Nucl. Med., No. 56, pp. 914-920.

Marchal, C., et al., Expression of Prostate Specific Membrane Antigen (PSMA) in Prostatic Adenocarcinoma and Prostatic Intraepithelial Neoplasia, 2004, Histol Histopathol, No. 19, pp. 715-718.

Benesova, Martina, et al., "Linker Modification Strategies To Control the Prostate-Specific Membrane Antigen {PSMA)-Targeting and Pharmacokinetic Properties of DOTA-Conjugated PSMA Inhibitors," 2016, J. Med. Chem., No. 59, pp. 1761-1775.

Eder, Matthias, et al., "68 Ga-Complex Lipophilicity and the Targeting Property of a Ure••Based PSMA Inhibitor for PET Imaging," 2012, BioConnjugate Chem., No. 23, pp. 688-697.

Mease, Ronnie C., et al., PET Imaging in Prostate Cancer: Focus on Prostate-Specific Membrane Antigen, 2013, Curr Top Med Chem., vol. 13, No. 8, pp. 951-962.

Spahn, et al., "We soil die Hormontherapie beim kastrationsresistenten Prostatakarzinom fortgefiihrt werden?," 2012, Urologe, 51 pp. 15-19.

Supplemental European Search Report, prepared for EP Application No. 19789294, mailed Nov. 26, 2021.

Sweat, et al., "Prostate-Specific Membrane Antigen Expression is Greatest in Prostate Adenocarcinomaand Lymph Node Metastases," 1998, Urology, 52(4) pp. 637-640.

Tan, G. et al. The efficacy and safety of abiraterone acetate in patients with high-risk prostate cancer: a meta-analysis based on six randomized control trials. Transl. Androl. Urol. 2020, 9, 1691-1699.

Tang, et al., "Prostate targeting ligands based on N-acetylated a-linked acidic dipeptidase," 2003, Biochemical and Biophysical Research Communications, 307(1) pp. 8-14.

Tang, et al., "Updated Application of Prostate-Specific Membrane Antigen to the Diagnosis and Treatment of Prostate Cancer," 2008, National Journal of Andrology, 14(1) pp. 79-82.

Tasch, J., et al., "A Unique Folate Hydrolase, Prostate-Specific Membrane Antigen (PSMA): A Target for Immunotherapy?" 2001, Critical Reviews in Immunology, 21(1-3) pp. 249-261.

Taylor et al., "Prostate Cancer Targeting Motifs: Expression of anb3, Neurotensin Receptor 1, Prostate Specific Membrane Antigen, and Prostate Stem Cell Antigen in Human Prostate Cancer Cell Lines and Xenografts," The Prostate 72:523-532 (2012).

Tehrani, O., et al., "Tumor Imaging Using 1-(2'-deoxy-2'-18F-Fluoro-(3-D-Arabinofuranosyl)Thymine and PET," 2007, Journal of Nuclear Medicine, 48(9) pp. 1436-1441.

Testa, et al., "Prostate Cancer: Sextant Localization with MR Imaging, MR Spectroscopy, and 11C-Choline PET/CT," 2007, Radiology, 244(3).

Thalmamm, G., "Advanced Prostate Cancer," English translation, 2012, Urologe, 51(1) pp. 7.

Thalmann, G., "Fortgeschrittenes Prostatakarzinom," 2012, Urologe, 51 pp. 7.

The Chemistry of Oxygen and Sulfur, https://web.archive.org/web/20080625021202/http:// chemed.chem.purdue.edu/genchem/topicreview/bp/ch10/group6.php#oxygen (date Jun. 25, 2008) accessed online on May 31, 2019, 21 pages (Year: 2008).

Truffert, J., et al., "Synthesis, Purification, and Characterization of Two Peptide-Oligonucleotide Conjugates as Potential Artificial Nucleases," 1996, Tetrahedron, 52(8) pp. 3005-3016.

Tykvart, et al., "Rational design of urea-based glutamate carboxypeptidase II (GCPII) inhibitors as versatile tools for specific drug targeting and delivery," 2014, Bioorganic & Medicinal Chemistry, 22(15) pp. 4099-4108.

Uprimny, et al., "68Ga-PSMA ligand PET versus 18F-NaF PET: evaluation of response to 223Ra therapy in a prostate cancer patient," 2015, European Journal of Nuclear Medicine and Molecular Imaging, 42(2) pp. 362-363.

Vallabhajosula, et al., "Radioimmunotherapy of Prostate Cancer in Human Xenografts Using Monoclonal Antibodies Specific to Prostate Specific Membrane Antigen (PSMA): Studies in Nude Mice," 2004, The Prostate, 58(2) pp. 145-155.

Vavere, et al., "1-11C-Acetate as a PET Radiopharmaceutical for Imaging Fatty Acid Synthase Expression in Prostate Cancer," 2008, Journal of Nuclear Medicine, 49(2) pp. 327-334.

Vees, H., et al., "18F-choline and/or 11C-acetate positron emission tomography: detection of residual or progressive subclinical disease at very low prostate-specific antigen values ( <1 ng/ml) after radical prostatectomy," 2007, BJU International, 99(6) pp. 1415-1420.

Viola-Villegas, N., et al., "Targeting Gallium to Cancer Cells through the Folate Receptor," 2008, Drug Target Insights, 3 pp. 13-25.

Viola-Villegas, N., et al., "Targeting the Folate Receptor (FR): Imaging and Cytotoxicity of Rel Conjugates in FR-Overexpressing Cancer Cells," 2008, ChemMedChem, 3(9) pp. 1387-1394.

Violet, J., et al., "Long-Term Follow-up and Outcomes of Retreatment in an Expanded 50-Patient Single-Center Phase II Prospective

(56) References Cited

OTHER PUBLICATIONS

Trial of 177Lu-PSMA-617 Theranostics in Metastatic Castration-Resistant Prostate Cancer," Journal of Nuclear Medicine, 2020, 61(6) pp. 857-865.
Vlahov, I., et al., "Design and regioselective synthesis of a new generation of targeted chemotherapeutics. Part 1: EC145, a folic acid conjugate of desacetylvinblastine monohydrazide," 2006, ScienceDirect, Bioorganic & Medical Chemistry Letters, 16(19) pp. 5093-5096.
Wang, et al., "Bioisosterism of urea-based GCPII inhibitors: Synthesis and structure—activity relationship studies," 2010, Bioorganic & Medicinal Chemistry Letters, 20(1) pp. 392-397.
Wang, et al., "Development of Targeted Near-Infrared Imaging Agents for Prostate Cancer," 2014, Molecular Cancer Therapeutics, 13(11) pp. 2595-2606.
Wang, et al., "Prostate-Specific Membrane Antigen Targeted Tubulysin Conjugates for Cancer Therapy," 246th ACS National Meeting and Exposition (Sep. 8, 2013) Poster.
Wang, Z., Single Low-Dose Injection of Evans Blue Modified PSMA-617 Radioligand Therapy Eliminates Prostate-Specific Membrane Antigen Positive Tumors, Bioconjugate Chemistry, 2018, 29, pp. 3213-3221.
Weineisen, et al., "Synthesis and preclinical evaluation of DOTAGA-conjugated PSMA ligands for functional imaging and endoradiotherapy of prostate cancer," 2014, EJNMMI Research, 4(63).
Weissbach, L. "Which Components Should 'Living Guidelines' Contain?," English translation, 2012, Urologe, 51(1) pp. 57-59.
Weissbach, L., "Welche Inhalte sollte eine living guideline besetzen?," 2012, Urologe, 51 pp. 57-59.
Whitaker, et al., "N-acetyl-L-aspartyl-L-glutamate peptidase-like 2 is overexpressed in cancer and promotes a pro-migratory and pro-metastatic phenotype," 2014, Oncogene, 33 pp. 5274-5287.
Wiberg, et al., "A comparison of some properties of C=O and C=S bonds," 2011, Arkivoc, 5 pp. 45-56.
Wiehr, et al., "Pharmacokinetics and PET Imaging Properties of Two Recombinant Anti-PSMA Antibody Fragments in Comparison to their Parental Antibody," 2014, The Prostate, 74(7) pp. 743-755.
Wright, et al., "Expression of Prostate-Specific Membrane Antigen in Normal, Benign, and Malignant Prostate Tissues," 1995, Urologic Oncology, 1(1) pp. 18-28.
Wu, et al., "A mild deprotection procedure for tert-butyl esters and tert-butyl ethers using ZnBr2 in methylene chloride," 2000, Tetrahedron Letters, 41(16) pp. 2847-2849.
Wu, et al., "The molecular pruning of a phosphoramidate peptidomimetic inhibitor of prostate-specific membrane antigen," 2007, Bioorganic & Medicinal Chemistry, 15(23) pp. 7434-7443.
Yadav, M.P. et al., "177Lu-DKFZ-PSMA-617 therapy in metastatic castration resistant prostate cancer: safety, efficacy, and quality of life assessment," European Jouranl of Nuclear Medicine and Molecular Imaging, 2016, 44(1) pp. 81-91.
Yamaguchi, et al., "Prostate cancer: a comparative study of 11C-choline PET and MR imaging combined with proton MR spectroscopy," 2005, European Journal of Nuclear Medicine and Molecular Imaging, 32(7) pp. 742-748.
Yang, J., et al., "Characterization of the pH of Folate Receptor-Containing Endosomes and the Rate of Hydrolysis of Internalized Acid-Labile Folate-Drug Conjugates," 2007, Journal of Pharmacology and Experimental Therapeutics, 321 (2) pp. 462-468.
Zaheer, et al., "New Agents and Techniques for Imaging Prostate Cancer," 2009, Journal of Nuclear Medicine, 50(9) pp. 1387-1390.
Zechmann, et al., "Radiation dosimetry and first therapy results with a 1241/131 1-labeled small molecule (MIP-1095) targeting PSMA for prostate cancer therapy," 2014, European Journal of Nuclear Medicine and Molecular Imaging, 41(7) pp. 1280-1292.
Zhang, et al., "A Remote Arene-Binding Site on Prostate Specific Membrane Antigen Revealed by Antibody-Recruiting Small Molecules," 2010, Journal of the American Chemical Society, 132(36) pp. 12711-12716.
Zhang, et al., "Prostate Specific Membrane Antigen (PSMA): A Novel Modulator of p38 for Proliferation, Migration, and Survival in Prostate Cancer Cells," 2013, The Prostate, 73(8) pp. 835-841.
Zhou J., et al., "Naag Peptidase Inhibitors and Their Potential for Diagnosis and Therapy," 2005, Nature Reviews Drug Discovery, 4(12) pp. 1015-1026.
Zhou, J., "In vivo evaluation of medical device-associated inflammation using macrophage-specific position emission tomography (PET) imaging," 2013, Bioorganic and Medicinal Chemistry Letters, 23(7) pp. 2044-2047.
Zophel, K. and Kotzerke, J., "Is 11C-choline the most appropriate tracer for prostate cancer?" 2004, European Journal of Nuclear Medicine and Molecular Imaging, 31(5) pp. 756-759.
Easton (An unexpected success for cancer immunotherapy treating prostate cancer. U Chicago Medicine. 2018.) (Year: 2018).
Extended European Search Report for application No. EP24221005.2, dated Jun. 26, 2025.
Harsanyi et al. "Synthesis of 2-phosphinoxidomethyl- and 2-phosphonomethyl glutaric acid derivatives", Heteroatom Chemistry, vol. 16, No. 7, Jan. 1, 2005 (Jan. 1, 2005), pp. 562-565.
Nedelcovych, M. et al. "Enhanced Brain Delivery of 2-(Phosphonomethyl)pentanedioic Acid Following Intranasal Administration of Its y-Substituted Ester Prodrugs", Molecular Pharmaceutics, vol. 14, No. 10, Oct. 2, 2017 (Oct. 2, 2017), pp. 3248-3257.
Rais, et al., "Bioanalytical method for evaluating the pharmacokinetics of the GCP-II inhibitor 2-phosphonomethylpentanedioicacid (2-PMPA)," 2014, Journal of Pharmaceutical and Biomedical Analysis, 88(25) pp. 162-169.
Rajasekaran, et al., "A Novel Cytoplasmic Tail MXXXL Motif Mediates the Internalization of Prostate-specific Membrane Antigen," 2003, Molecular Biology of the Cell, 14(12) pp. 4835-4845.
Ranasinghe, M., et al., " A Facile Synthesis of Unsymmetrical Thiolsulfonates via Sulfonylation of Mercaptans," 1988, Synthetic Communications, 18(3) pp. 227-232.
Rathke, H. et al. Repeated 177Lu-Labeled PSMA-617 Radioligand Therapy Using Treatment Activities of Up to 9.3 GBq. J Nucl Med, 2018, 59, 459-465.
Reddy, J., et al., "PSMA-specific anti-tumor activity of the targeted-tubulysin conjugate, EC1169," American Association for Cancer Research Annual Meeting (Apr. 8, 2013) Poster.
Reske, "Nuclear Imaging of Prostate Cancer," English translation, 2007, Urologe, 46(11) pp. 1485-1499.
Reske, et al., "[11C]choline PET/CT imaging in occult local relapse of prostate cancer after radical prostatectomy," 2008, European Journal of Nuclear Medicine and Molecular Imaging, 35 pp. 9-17.
Reske, et al., "[11C]Choline uptake with PET/CT for the initial diagnosis of prostate cancer: relation to PSA levels, tumour stage and anti-androgenic therapy," 2008, European Journal of Nuclear Medicine and Molecular Imaging, 35(9) pp. 1740-1741.
Reske, et al., "Advancement of PET and PET/CT in Prostate Carcinoma," English translation, 2006, Urologe, 45(6) pp. 707-714.
Reske, et al., "Nuklearmedizinische Diagnostik beim Prostatakarzinom," 2007, Urologe, 46 pp. 1485-1499.
Reske, et al., "PET and PET/CT in Relapsing Prostate Carcinoma," English translation, 2006, Urologe, 45(10) pp. 1240-1250.
Reske, et al., "PET und PET/CT in der Rezidivdiagnostik des Prostatakarzinoms," 2006, Urologe, 45 pp. 1240-1250.
Reske, et al., "Weiterentwicklung der PET und des PET/CT beim Prostatakarzinom," 2006, Urologe, 45 pp. 707-714.
Reske, S., et al., "Imaging Prostate Cancer with 11C-Choline PET/CT," 2006, Journal of Nuclear Medicine, 47(8) pp. 1249-1254.
Rich, J.N. Cancer stem cells in radiation resistance. Cancer research. Oct. 1, 2007; 67(19):8980-4.
Rinnab, et al., "[11C]Choline PET/CT for Targeted Salvage Lymph Node Dissection in Patients with Biochemical Recurrence after Primary Curative Therapy for Prostate Cancer," 2008, Urology International, 81 pp. 191-197.
Rinnab, et al., "[11C]choline PET/CT in prostate cancer patients with biochemical recurrence after radical prostatectomy," 2009, World Journal of Urology, 27 pp. 619-625.
Rinnab, L., et al., "Evaluation of [11C]-choline positron-emission/computed tomography in patients with increasing prostate-specific

(56) References Cited

OTHER PUBLICATIONS antigen levels after primary treatment for prostate cancer," 2007, BJU International, 100(4), pp. 786-793.
Rioja, et al., "Role of positron emission tomography in urological oncology," BJU International, 106(11) pp. 1578-1593.
Ristau, et al., "The prostate-specific membrane antigen: Lessons and current clinical implications from 20 years of research," 2014, Urologic Oncology: Seminars and Original Investigations, 32(3) pp. 272-279.
Roethke, et al., "Hyrbid Positron Emission Tomography-Magnetic Resonance Imaging with Gallium 68 Prostate-specific Membrane Antigen Tracer: A Next Step for Imaging of Recurrent Prostate Cancer—Preliminary Results," 2013, European Urology, 64(5) pp. 862-864.
Rojas et al., "Kinetics and inhibition of glutamate carboxypeptidase II using a microplate assay." Analytical biochemistry. Nov. 1, 2002;310(1):50-4. (Year: 2002).
Rong, et al., "Molecular Modeling of the Interaction of Glutamate Carboxypeptidase II with Its Potent NAAG-Based Inhibitors," 2002, Journal of Medicinal Chemistry, 45(19) pp. 4140-4152.
Rosar, F. et al. Molecular imaging and biochemical response assessment after a single cycle of [225Ac]Ac-PSMA-617/[1 77Lu]LuPSMA-6 1 7 tandem therapy in mCRPC patients whohave progressed on [1 77Lu]Lu-PSMA-617 monotherapy. Theranostics. 2021; 11(9): 4050-4060. doi: 10.7150/thno.56211.
Rosenthal, S., et al., "Utility of Capromab Pendetide (ProstaScint) Imaging in the Management of Prostate Cancer," 2001, Techniques in Urology, 7(1) pp. 27-37.
Rossi et al., "N-Nmoc-L-glutamate, a new caged glutamate with high chemical stability and low pre-photolysis activity," J Biol Chem. 272(52):32933-9 (1997).
Rothke, M., et al. "Potenziale der PET/MRT in der Diagnostik des Prostatakariznoms," 2013, Radiologe, 53(8) pp. 676-681.
Roy, J., et al., "DUPA Conjugation of a Cytotoxic Indenoisoquinoline Topoisomerase I Inhibitor for Selective Prostate Cancer Cell Targeting," 2015, Journal of Medicinal Chemistry, 58(7) pp. 3094-3103.
Rybalov, et al., "Impact of total PSA, PSA doubling time and PSA velocity on detection rates of 11C-Choline positron emission tomography in recurrent prostate cancer," 2013, World Journal of Urology, 31(2) pp. 319-323.
Sacha, et al., "Expression of Glutamate Carboxypeptidase II in Human Brain," 2007, Neuroscience, 144(4) pp. 1361-1372.
Sartor, O. et al., "Lutetium-177-PSMA-617 for Metastatic Castration-Resistant Prostate Cancer," The New England Journal of Medicine, Jun. 23, 2021, pp. 1-13.
Sathekge, M., et al., "225Ac-PSMA-617 in chemotherapy-naïve patients with advanced prostate cancer: a pilot study," European Journal of Nuclear Medicine and Molecular Imaging, Springer Berlin Heidelberg, Sep. 19, 2018, 46(1) pp. 129-138.
Scattoni, et al., "Detection of Lymph-Node Metastases with Integrated [11C]Choline PET/CT in Patients with PSA Failure after Radical Retropubic Prostatectomy: Results Confirmed by Open Pelvic-Retroperitoneal Lymphadenectomy," 2007, European Urology, 52(2) pp. 423-429.
Schafer, et al., "A dimerized urea-based inhibitor of the prostate-specific membrane antigen for 68Ga-PET imaging of prostate cancer," 2012, EJNMMI Research, 2(1) pp. 23.
Scheffel, et al., "PET Imaging of GRP Receptor Expression in Prostate Cancer," 2004, The Journal of Nuclear Medicine, 45(8) pp. 1277-1278.
Scher, B., et al., "Value of 11C-choline PET and PET/CT in patients with suspected prostate cancer," 2007, European Journal of Nuclear Medicine and Molecular Imaging, 34 pp. 45-53.
Scher, et al., "PET/CT imaging of recurrent prostate cancer," 2008, European Journal of Nuclear Medicine and Molecular Imaging, 35 pp. 5-8.
Schulke, N., et al., "The homodimer of prostate-specific membrane antigen is a functional target for cancer therapy," 2003, Proceedings of the National Academy of Sciences of the United States of America, 100(22) pp. 12590-12595.
Schuster, D., et al., "Initial Experience with the Radiotracer Anti-1-Amino-3-18F-Fluorocyclobutane-1-Carboxylic Acid with PET/CT in Prostate Carcinoma," 2007, Journal of Nuclear Medicine, 48(1) pp. 56-63.
Seifert, R. et al. Radioligand therapy using [177Lu]Lu-PSMA-617 in mCRPC: a pre-Vision single-center analysis. European Journal of Nuclear Medicine and Molecular Imaging (2020) 47:2106-2112.
Shvarts, et al., "Positron Emission Tomography in Urologic Oncology," 2002, Cancer Control, 9(4) pp. 335-342.
Silver, et al., "Prostate-specific Membrane Antigen Expression in Normal and Malignant Human Tissues," 1997, Clinical Cancer Research, 3(1) pp. 81-85.
Silverman, R., "The Organic Chemistry of Drug Design and Drug Action," Elsevier Academic Press, 2nd Edition, Jan. 12, 2004, Hardback ISBN: 9780126437324.
Silvola, J., et al., "A118F-NOTA-Folate Accumulates in Atherosclerotic Plaques and Can be Detected by PET/CT", Poster presented Nov. 7, 2015 in Orlando, FL at the 2015 American Heart Association, Resuscitation Science Symposium (http://newsroom_heart.org/events/scientific-sessions-2015-newsroom-2942760).
Silvola, J., et al.,"A118F-NOTA-Folate Accumulates in Atherosclerotic Plaques and Can be Detected by PET/CT", Published reference of poster, Nov. 10, 2015, at http://circ.ahajournals.org/ content/132/Suppl_3/A18873?cited-by=&legid=circulationaha;132/Suppl_3/A18873; Circulation, 2015, 132:A18873.
Simone, et al., "What's in a Label? Radioimmunotherapy for Metastatic Prostate Cancer," 2013, Clinical Cancer Research, 19(18) pp. 4908-4910.
Slusher, et al., "Immunocytochemical Localization of the N-Acetyl-Aspartyl-Glutamate (NAAG) Hydrolyzing Enzyme N-Acetylated a-Linked Acidic Dipeptidase (NAALADase)," 1992, The Journal of Comparative Neuorology, 315(2) pp. 217-229.
Slusher, et al., "Selective inhibition of NAALADase, which converts NAAG to glutamate, reduces ischemic brain injury," 1999, Nature Medicine, 5(12) pp. 1396-1402.
Soloviev, et al., "PET imaging with 11C-acetate in prostate cancer: a biochemical, radiochemical and clinical perspective," 2008, European Journal of Nuclear Medicine and Molecular Imaging, 35(5) pp. 942-949.
Spahn, et al., "How Should Hormone Therapy for Castration-Resistant Prostate Cancer be Continued?," English translation, 2012, Urologe, 51(1) pp. 15-19.
Afshar-Oromieh, et al., "[68Ga]Gallium-labelled PSMA ligand as superior PET tracer for the diagnosis of prostate cancer: comparison with 18F-FECH," 2012, European Journal of Nuclear Medicine and Molecular Imaging, 39 pp. 1085-1086.
Afshar-Oromieh, et al., "Comparison of PET imaging with a 68Ga-labelled PSMA ligand and 18F-choline-based PET/CT for the diagnosis of recurrent prostate cancer," 2014, European Journal of Nuclear Medicine and Molecular Imaging, 41(1) pp. 11-20.
Afshar-Oromieh, et al., "Comparison of PET/CT and PET/MRI hybrid systems using a 68Ga-labelled PSMA ligand for the diagnosis of recurrent prostate cancer: initial experience," 2014, European Journal of Nuclear Medicine and Molecular Imaging, 41(5) pp. 887-897.
Afshar-Oromieh, et al., "PET imaging with a [68Ga]gallium-labelled PSMA ligand for the diagnosis of prostate cancer: biodistribution in humans and first evaluation of tumour lesions," 2013, European Journal of Nuclear Medicine and Molecular Imaging, 40 pp. 486-495.
Afshar-Oromieh, et al., "PET/MRI with a 68Ga-PSMA ligand for the detection of prostate cancer," 2013, European Journal of Nuclear Medicine and Molecular Imaging, 40(10) pp. 1629-1630.
Afshar-Oromieh, et al., "The diagnostic value of PET/CT imaging with the 68Ga-labelled PSMA ligand HBED-CC in the diagnosis of recurrent prostate cancer," 2015, European Journal of Nuclear Medicine and Molecular Imaging, 42 pp. 197-209.
Agarwal, et al., "A Dimeric Peptide That Binds Selectively to Prostate-Specific Membrane Antigen and Inhibits its Enzymatic Activity," 2006, Cancer Research, 66(18) pp. 9171-9177.

(56) References Cited

OTHER PUBLICATIONS

Ahmadzadehfar, H. et al. "Early side effects and first results of radioligand therapy with (177)Lu-DKFZ-617 PSMA of castrate-resistant metastatic prostate cancer: a two-centre study." EJNMMI Res. Dec. 2015;5(1):114. doi: 10.1186/s13550-015-0114-2. Epub Jun. 20, 2015.
Ahmadzadehfar, H., et al., "Overall survival and response pattern of castration-resistant metastatic prostate cancer to multiple cycles of radioligand therapy using [177Lu] Lu-PSMA-617," European Journal of Nuclear Medicine and Molecular Imaging, 2017, 44(9) pp. 1448-1454.
Alt, et al., "High-Resolution Animal PET Imaging of Prostate Cancer Xenografts with Three Different 64Cu-Labeled Antibodies against Native Cell-Adherent PSMA," 2010, The Prostate, 70(13) pp. 1413-1421.
Ananias, et al., "Expression of the Gastrin-Releasing Peptide Receptor, the Prostate Stem Cell Antigen and the Prostate-Specific Membrane Antigen in Lymph Node and Bone Metastases of Prostate Cancer," 2009, The Prostate, 69(10) pp. 1101-1108.
Anderson, et al., "Substrate specificity of prostate-specific membrane antigen," 2007, Bioorganic & Medicinal Chemistry, 15(21) pp. 6678-6686.
Antunes, et al., "PGC and PSMA in prostate cancer diagnosis: tissue analysis from biopsy samples," 2013, International Brazilian Jurnal of Urology, 39(5) pp. 649-656.
Armor, et al., "A comparison of 2D and 3D regions within the same patient to derive organ and tissue kinetics," 2012, Journal of Nuclear Medicine, 53(1) pp. 13.
Australian Application Serial No. 2021200067, First Examination Report mailed Feb. 16, 2022, 4 pgs.
Bacich, et al., "Cloning, expression, genomic localization, and enzymatic activities of the mouse homolog of prostate-specific membrane antigen/NAALADase/folate hydrolase," 2001, Mammalian Genome, 12 pp. 117-123.
Baiz, et al., "Synthesis and Characterization of a Novel Prostate Cancer-Targeted Phosphatidylinositol-3-kinase Inhibitor Prodrug," 2012, Journal of Medicinal Chemistry, 55(18 pp. 8038-8046.
Banerjee, et al., "64Cu-Labeled Inhibitors of Prostate-Specific Membrane Antigen for PET Imaging of Prostate Cancer," 2014, Journal of Medicinal Chemistry, 57(6) pp. 2657-2669.
Banerjee, et al., "68Ga-Labeled Inhibitors of Prostate-Specific Membrane Antigen (PSMA) for Imaging Prostate Cancer," 2010, Journal of Medicinal Chemistry, 53(14) pp. 5333-5341.
Banerjee, et al., "A Modular Strategy to Prepare Multivalent Inhibitors of Prostate-Specific Membrane Antigen (PSMA)," 2011, Oncotarget, 2(12) pp. 1244-1253.
Banerjee, S., et al., "Sequential SPECT and Optical Imaging of Experimental Models of Prostate Cancer with a Dual Modality Inhibitor of the Prostate-Specific Membrane Antigen," 2011, Angewandte Chemie International Edition, 50(39) pp. 9167-9170.
Banerjee, S., et al., "Synthesis and Evaluation of Technetium-99m-and Rhenium-Labeled Inhibitors of the Prostate-Specific Membrane Antigen (PSMA)," 2008, Journal of Medicinal Chemistry, 51(15) pp. 4504-4517.
Barinka, et al., "A high-resolution structure of ligand-free human glutamate carboxypeptidase II," 2007, Acta Crystallographica, 63(3) pp. 150-153.
Barinka, et al., "Interactions between Human Glutamate Carboxypeptidase II and Urea-Based Inhibitors: Structural Characterization," 2008, Journal of Medicinal Chemistry, 51 pp. 7737-7743.
Barinka, et al., "Structural Insight into the Pharmacophore Pocket of Human Glutamate Carboxypeptidase II," 2007, Journal of Medicinal Chemistry, 50(14) pp. 3267-3273.
Barraclough, H. et al. Biostatistics Primer: What a Clinician Ought to Know: Hazard Ratios. J. Thorac. Oneal. 2011, 978-982.
Barrett, et al., "First-in-Man Evaluation of 2 High-Affinity PSMA-Avid Small Molecules for Imaging Prostate Cancer," 2013, Journal of Nuclear Medicine, 54(3) pp. 380-387.
Beheshti, et al., "Prostate Cancer: Role of SPECT and PET in Imaging Bone Metastases," 2009, Seminars in Nuclear Medicine, 39(6) pp. 396-407.
Behr, S.C. et al. Phase I Study of CTT1057, an 18F-Labeled Imaging Agent with Phosphoramidate Core Targeting Prostate-Specific Membrane Antigen in Prostate Cancer. J Nucl Med 2019; 60:910-916.
Bellmunt et al., "Castration-resistant prostate cancer: new science and therapeutic prospects." Therapeutic advances in medical oncology. May 2010; 2(3):189-207.
Belloli, et al., "Characterization of preclinical models of prostate cancer using PET-based molecular imaging," 2009, European Journal of Nuclear Medicine and Molecular Imaging, 36 pp. 1245-1255.
Benesova, M., et al., "Linker Modifications of DOTA-conjugated Inhibitors of the Prostate-Specific Membrane Antigen (PSMA)," abstract, European Journal of Nuclear Medicine and Molecular Imaging, available Oct. 16, 2013,40, Suppl. 2, S193.
Benesova, M., et al., "Linker Modifications of DOTA-conjugated Inhibitors of the Prostate-Specific Membrane Antigen (PSMA)," poster, presented at the European Association of Nuclear Medicine Conference on Oct. 21, 2013.
Bennett, V. and Simmons, M.," Analysis of fluorescently labeled substance P analogs: binding, imaging and receptor activation," 2001, BMC Chemical Biology, 1:1. doi:10.1186/1472-6769-1-1.
Bostwick, et al., "Prostate Specific Membrane Antigen Expression in Prostatic Intraepithelial Neoplasia and Adenocarcinoma," 1998, Cancer, 82(11) pp. 2256-2261.
Bouchelouche, et al., -Image and treat: an individualized approach to urological tumors, 2010, Current Opinion in Oncology, 22(3) pp. 274-280.
Bouchelouche, et al., "Imaging Prostate Cancer: An Update on Positron Emission Tomography and Magnetic Resonance Imaging," 2010, Current Urology Reports, 11 pp. 180-190.
Bouchelouche, et al., "PET/CT Imaging and Radioimmunotherapy of Prostate Cancer," 2011, Seminar in Nuclear Medicine, 41(1) pp. 29-44.
Bouchelouche, et al., "Prostate Specific Membrane Antigen—A Target for Imaging and Therapy with Radionuclides," 2010, Discovery Medicine, 9(44) pp. 55-61.
Bouchelouche, K., et al., "Positron emission tomography/computed tomography and radioimmunotherapy of prostate cancer," Current Opinion in Oncology, 21(5) pp. 469-474.
Brauer, A. et al., "177Lu-PSMA-617 radioligand therapy and outcome in patients with metastasized castration-resistant prostate cancer," European Journal of Nuclear Medicine and Molecular Imaging, 2017, 44(10) pp. 1663-1670.
Bzdega, et al., "The cloning and characterization of a second brain enzyme with NAAG peptidase activity," 2004, Journal of Neurochemistry, 89(3) pp. 627-635.
Calais, J. et al. Prospective phase 2 trial of PSMA-targeted molecular Radiotherapy with 177Lu-PSMA-617 for metastatic castration-reSISTant Prostate Cancer (RESIST-PC): efficacy results of the UCLA cohort. J Nucl Med, 2021, 62:1440-1446.
Ceci, et al., "11C-Choline PET/CT in patients with hormone-resistant prostate cancer showing biochemical relapse after radical prostatectomy," 2013, European Journal of Nuclear Medicine and Molecular Imaging, 40(2) pp. 149-155.
Chandran, et al., "Characterization of a targeted nanoparticle functionalized with a urea-based inhibitor of prostate-specific membrane antigen (PSMA)," 2008, Cancer Biology & Therapy, 7(6) pp. 974-982.
Chang, et al., "Five Different Anti-Prostate-specific Membrane Antigen (PSMA) Antibodies Confirm PSMA Expression in Tumor-associated Neovasculature," 1999, Cancer Research, 59(13) pp. 3192-3198.
Chang, et al., "The clinical role of prostate-specific membrane antigen (PSMA)," 2002, Urologic Oncology, 7(1) pp. 7-12.
Chatalic, K. et al. Towards Personalized Treatment of Prostate Cancer: PSMA I&T, a Promising Prostate-Specific Membrane Antigen-Targeted Theranostic Agent. Theranostics. 2016; 6(6): pp. 849-861.
Chen, et al., "2-(3-{1-Carboxy-5-[(6-[18F]Fluoro-Pyridine-3-Carbonyl)-Amino]-Pentyl}-Ureido)-Pentanedioic Acid, [18F]DCFPyL,

(56) References Cited

OTHER PUBLICATIONS a PSMA-Based PET Imaging Agent for Prostate Cancer," 2011, Clinical Cancer Research, 17(24) pp. 7645-7653.
Chen, et al., "A low molecular weight PSMA-based fluorescent imaging agent for cancer," 2009, Biochemical and Biophysical Research Communications, 390(3) pp. 624-629.
Priftakis (Neuroendocrine differentiation in castration resistant prostate cancer: A case report. Molecular and Clinical Oncology. 2015) (Year: 2015).
Sandhu, Shahneen et al.: "Poster Discussion Session-5017-Prince: Phase I trial of 177 Lu-PSMA-617 in combination with pembrolizumab in patients with metastatic castration-resistant prostate cancer (mCRPC)", Journal of clinical oncology, vol. 40, No. 16 Suppl, Jun. 2, 2022 (Jun. 2, 2022).
Reexamination Report dated Sep. 16, 2025 of Australian Patent 2020201329, 6 pages.
Panwar P et al, "Radiolabeling and Biological Evaluation of Dota-Ph-Al Derivative Conjugated to Anti-EGFR Antibody IOR EGF/R3 for Targeted Tumor Imaging and Therapy", Cancer Biology & Therapy, Landes Bioscience, US, (Aug. 1, 2005), vol. 4, No. 8, ISSN 1538-4047, pp. 854-860.
Doronina Svetlana O et al, "Development of potent monoclonal antibody auristatin conjugates for cancer therapy", Nature Biotechnology, Nature Publishing Group US, New York, (Jul. 1, 2003), vol. 21, No. 7, ISSN 1087-0156, pp. 778-784.
Rathke, H. et al., "Deescalated 225Ac-PSMA-617 Versus 177Lu/225Ac-PSMA-617 Cocktail Therapy: A Single-Center Retrospective Analysis of 233 Patients," Journal of Nuclear Medicine, 2024, 65, 1057-1063.
Meyer, C. et al., "Tandem Isotope Therapy with 225Ac- and 177Lu-PSMA-617 in a Murine Model of Prostate Cancer," The Journal of Nuclear Medicine, 2023, 64, 1772.
Sheikh, G.T. et al. "RECIP 1.0 + PSA for response assessment in mCRPC patients treated with 225Ac / 177Lu PSMA combination therapy." EJNMMI Research, 2025, 15:19.
Haberkorn, U. et al. "The Future of Radioligand Therapy: a, b, or Both?" Journal of Nuclear Medicine, 2017, 58 (7), 1017-1018.
Lange, P., "ProstaScint scan for staging prostate cancer," 2001, Urology, 57(3) pp. 402-406.
Lapi, et al., "Assessment of an 18F-Labeled Phosphoramidate Peptidomimetic as a New Prostate-Specific Membrane Antigen—Targeted Imaging Agent for Prostate Cancer," 2009, Journal of Nuclear Medicine, 50(12) pp. 2042-2048.
Larock, R., "Comprehensive Organic Transformations: A Guide to Functional Group Preparations," VCH Publishers, Inc. New York (1989).
Larson, S., et al., "Tumor Localization of 1613-18F-Fluoro-5a-Dihydrotestosterone Versus 18F-FDG in Patients with Progressive, Metastatic Prostate Cancer," 2004, Journal of Nuclear Medicine, 45(3) pp. 366-373.
Lau, J., "Bench to Bedside: Albumin Binders for Improved Cancer Radioligand Therapies," 2019, Bioconjugate Chemistry, 30, pp. 487-502.
Leek, et al., "Prostate-specific membrane antigen: evidence for the existence of a second related human gene," 1995, British Journal of Cancer, 72 pp. 583-588.
Lees, et al., "Active surveillance in prostate cancer: patient selection and triggers for intervention," 2012, Current Opinion in Urology, 22(3) pp. 210-215.
Lesche, et al., "Preclinical evaluation of BAY 1075553, a novel 18F-labelled inhibitor of prostate-specific membrane antigen for PET imaging of prostate cancer," 2014, European Journal of Nuclear Medicine and Molecular Imaging, 41 pp. 89-101.
Liu, et al., "A targeted low molecular weight near-infrared fluorescent probe for prostate cancer," 2010, Bioorganic & Medicinal Chemistry Letters, 20(23) pp. 7124-7126.
Liu, et al., "C-11 Choline PET/CT Imaging for Differentiating Malignant From Benign Prostate Lesions," 2008, Clinical Nuclear Medicine, 33(10) pp. 671-676.
Liu, et al., "Constitutive and Antibody-induced Internalization of Prostate-specific Membrane Antigen," 1998, Cancer Research, 58(18) pp. 4055-4060.
Liu, et al., "Functional prostate-specific membrane antigen is enriched in exosomes from prostate cancer cells," 2014, International Journal of Oncology, 44(3) pp. 918-922.
Liu, et al., "Prolonged androgen deprivation leads to downregulation of androgen receptor and prostate-specific membrane antigen in prostate cancer cells," 2012, International Journal of Oncology, 41(6) pp. 2087-2092.
Liu, et al., "Pseudoirreversible Inhibition of Prostate-Specific Membrane Antigen by Phosphoramidate Peptidomimetics," 2008, Biochemistry, 47(48) pp. 12658-12660.
Liu, et al., "Targeting prostate cancer cells with a multivalent PSMA inhibitor-guided streptavidin conjugate," 2012, Bioorganic & Medicinal Chemistry Letters, 22(12) pp. 3931-3934.
Liu, M., et al., "Synthesis and Biological Evaluation of Diethylenetriamine Pentaacetic acid-Polyethylene Glycol Folate: A new Folate-Derived, 99mTc-Based Radiopharmaceutical," 2005, Bioconjugate Chemistry, 16(5) pp. 1126-1132.
Lord, et al., "18F-Fluorocholine integrated PET/MRI for the initial staging of prostate cancer," 2011, European Journal of Nuclear Medicine and Molecular Imaging, 38 pp. 2288.
Lu, G., et al., "Synthesis and SAR of 99mTc/Re-labeled small molecule prostate specific membrane antigen inhibitors with novel polar chelates," 2013, Bioorganic and Medicinal Chemistry Letters, 23(5) pp. 1557-1563.
Luboldt, et al., "Prostate Carcinoma: Diffusion-weighted Imaging as Potential Alternative to Conventional MR and 11C-Choline PET/CT for Detection of Bone Metastases," 2008, Radiology, 249(3) pp. 1017-1025.
Lupoid, et al., "Identification and characterization of nuclease-stabilized RNA molecules that bind human prostate cancer cells via the prostate-specific membrane antigen." Cancer Res. 2002; 62:4029-4033.
Lupold, S., et al., "Identification and Characterization of Nuclease-stabilized RNA Molecules that Bind Human Prostate Cancer Cells via the Prostate-specific Membrane Antigen," 2002, Cancer Research, 62(14) pp. 4029-4033.
Lutje, et al., "Dual-Modality Image-Guided Surgery of Prostate Cancer with a Radiolabeled Fluorescent Anti-PSMA Monoclonal Antibody," 2014, Journal of Nuclear Medicine, 55(6) pp. 995-1001.
Lutje, et al., "Prospects in Radionuclide Imaging of Prostate Cancer," 2012, The Prostate, 72(11) pp. 1262-1272.
Lymperis et al., "Radiometal-Dependent Biological Profile of the Radiolabeled Gastrin-Releasing Peptide Receptor Antagonist SB3 in Cancer Theranostics: Metabolic and Biodistribution Patterns Defined by Neprilysin," Bioconjug Chem. 29(5):1774-84 (2018).
Majer, P. et al. Discovery of Orally Available Prodrugs of the Glutamate Carboxypeptidase II (GCPII) Inhibitor 2-Phosphonomethylpentanedioic Acid (2-PMPA). Journal of Medicinal Chemistry, 2016. 59 (6), pp. 2810-2819. DOI: 10.1021/acs.jmedchem.6b00062.
Majer, P., et al., "Synthesis and Biological Evaluation of Thiol-Based Inhibitors of Glutamate Carboxypeptodase II: Discovery of an Orally Active GCP II Inhibitor," 2003, Journal of Medicinal Chemistry, 46(10) pp. 1989-1996.
Malik, et al., "One pot radiofluorination of a new potential PSMA ligand [Al18F]NOTA-DUPA-Pep," 2012, Journal of Labelled Compounds and Radiopharmaceuticals, 55(9) pp. 320-325.
Malik, et al., "Radiosynthesis of a new PSMA targeting ligand ([18F]FPy-DUPA-Pep)," 2011, Applied Radiation and Isotopes, 69(7) pp. 1014-1018.
Mannweiler, et al., "Heterogeneity of Prostate-Specific Membrane Antigen (PSMA) Expression in Prostate Carcinoma with Distant Metastasis," 2009, Pathology and Oncology Research, 15(2) pp. 167-172.
Maresca, et al., "Influence of functionalized chelators on affinity and pharmacokinetics of 99mTc(CO)3-labeled small molecules targeting prostate specific membrane antigen (PSMA)," 2010, Journal of Nuclear Medicine, 51(2) pp. 250.

(56) References Cited

OTHER PUBLICATIONS

Maresca, K., et al., "A Series of Halogenated Heterodimeric Inhibitors of Prostate Specific Membrane Antigen (PSMA) as Radiolabeled Probes for Targeting Prostate Cancer," 2009, Journal of Medicinal Chemistry, 52(2) pp. 347-357.
Maresca, K., et al., "Molecular targeting of prostate cancer with small molecule inhibitors of prostate specific membrane antigen (PSMA)," 2007, Journal of Nuclear Medicine, 48 (Supplement 2 ).
Martin, P., et al., "A New Access to 2'-O-Alkylated Ribonucleosides and Properties of 2'-O-Alkylated Oligoribonucleotides," 1995, Helvetica Chimica Acta, 78(2) pp. 486-504 and Abstract.
Matthies, et al., "Imaging of prostate cancer metastases with 18F-fluoroacetate using PET/CT," 2004, European Journal of Nuclear Medicine and Molecular Imaging, 31 pp. 797.
Mcbride, et al., "Radiofluorination using aluminum-fluoride (A118F)", 2013, EJNMMI Research, 3(36) pp. 1-11.
Mcnamara, J., et al., "Cell Type Specific Delivery of siRNAs with Aptamer-siRNA Chimeras," 2006, Nature Biotechnolgy, 24(8) pp. 1005-1015.
Mease, R., "General Approach for the Preparation of Fluorescent PSMA GCPII Inhibitors", Abstract ID: 470 Poster board space: 29, Molecular Imaging, vol. 5, No. 3, (Jul. 2006), 322-323.
Mease, R., et al., "N-[N-[(S)-1,3-Dicarboxypropyl]Carbamoyl]-4-[18F]Fluorobenzyl-LCysteine, [18F]DCFBC: A New Imaging Probe for Prostate Cancer," 2008, Clinical Cancer Research, 14(10) pp. 3036-3043.
Meighan, et al., "Recombinant Glutamate Carboxypeptidase II (Prostate Specific Membrane Antigen-PSMA)-Cellular Localization and Bioactivity Analyses," 2003, Journal of Protein Chemistry, 22(4) pp. 317-326.
Meinenhofer, et al., "Solid-Phase Synthesis with Attachment of Peptide to Resin through an Amino Acid Side Chain: [8-Lysine]-Vasopressin," 1971, Proceedings of the National Academy of Sciences of the United States of America, 68(5) pp. 1006-1009.
Meinhardt et al., "Laparoscopic Sentinel Lymph Node Biopsy for Prostate Cancer: The Relevance of Locations Outside the Extended Dissection Area," Prostate Cancer vol. 2012, Article ID 751753, 4 pages.
Melby, E., et at., "Entry of Protein Toxins in Polarized Epithelial Cells," Cancer Research, 1993, 53(8) pp. 1755-1760.
Mertens, et al., "PET with 18F-labelled choline-based tracers for tumour imaging: a review of the literature," 2010, European Journal of Nuclear Medicine and Molecular Imaging, 37 pp. 2188-2193.
Mesters, J., et al., "Structure of Glutamate Carboxypeptidase II, a Drug Target in Neuronal Damage and Prostate Cancer," 2006, The EMBO Journal, 25(6) pp. 1375-1384.
Mhawech-Fauceglia, et al., "Prostate-specific membrane antigen (PSMA) protein expression in normal and neoplastic tissues and its sensitivity and specificity in prostate adenocarcinoma: an immunohistochemical study using mutiple tumour tissue microarray technique," 2007, Histopathology, 50(4) pp. 472-483.
Mier, W., et al., "Conjugation of DOTA Using Isolated Phenolic Active Esters: The Labeling and Biodistribution of Albumin as Blood Pool Marker," 2005, Bioconjugate Chemistry, 16(1) pp. 237-240.
Milowsky, et al., "Phase I Trial of Yttrium-90 -Labeled Anti-Prostate-Specific Membrane Antigen Monoclonal Antibody J591 for Androgen-Independent Prostate Cancer," 2004, Journal of Clinical Oncology, 22(13) pp. 2522-2531.
Minner, et al., "High Level PSMA Expression Is Associated With Early PSA Recurrence in Surgically Treated Prostate Cancer," 2011, The Prostate, 71(3) pp. 281-288.
Mlcochova, et al., "Mapping of the active site of glutamate carboxypeptidase II by site-directed mutagenesis," 2007, FEBS Journal, 274 pp. 4731-4741.
Moltzahn, et al., "Die ossare Metastasierung des Prostatakarzinoms," 2012, Urologe, 51 pp. 20-26.
Moltzhan, et al., "Bone Metastasis in Prostate Cancer," English translation, 2012, Urologe, 51(1) pp. 20-26.
Morris, et al., "11C-acetate PET imaging in prostate cancer," 2007, European Journal of Nuclear Medicine and Molecular Imaging, 34 pp. 181-184.
Muller, Folate-based radiotracers for PET imaging—update and perspectives. Molecules. Apr. 29, 2013;18 (5):5005-31. doi: 10.3390/molecules18055005. PMID: 23629756; PMCID: PMC6269920.
Muller, C., et al., "Synthesis and in Vitro/in Vivo Evaluation of Novel 99mTc(CO)3-Folates," 2006, Bioconjugate Chemistry, 17(3) pp. 797-806.
Murphy, et al., "Current Evaluation of the Tissue Localization and Diagnostic Utility of Prostate Specific Membrane Antigen," 1998, Cancer, 83(11) pp. 2259-2269.
Nan, F., et al., "Dual Function Glutamate-Related Ligands: Discovery of a Novel, Potent Inhibitor of Glutamate Carboxypeptidase II Possessing mGluR3 Agonist Activity," 2000, Journal of Medicinal Chemistry, 43(5) pp. 772-774.
Nedelcovych, M.T. et al. JHU-2545 selectively shields salivary glands and kidneys during PSMA-targeted radiotherapy. bioRxiv. Oct. 30, 2018:457085.
Nedrow-Byers, et al., "A Phosphoramidate-Based Prostate-Specific Membrane Antigen-Targeted SPECT Agent," 2012, The Prostate, 72(8) pp. 904-912.
Nedrow-Byers, et al., "PSMA-Targeted SPECT Agents: Mode of Binding Effect on In Vitro Performance," 2013, The Prostate, 73(4) pp. 355-362.
New Zealand Application Serial No. 758917, Subsequent Examiners Report mailed Feb. 9, 2022, 1 pg.
O'Keefe, et al., "Comparative Analysis of Prostate-Specific Membrane Antigen (PSMA) Versus a Prostate-Specific Membrane Antigen-Like Gene," 2004, The Prostate, 58(2) pp. 200-210.
Oehr et al., "Imaging of prostate cancer," 2007, Current Opinion in Oncology, 19 pp. 259-264.
Olsnes, S., et al., "Immunotoxins-Entry into Cells and Mechanisms of Action," 1989, Immunology Today, 10(9) pp. 291-295.
Oluwatayo F. Ikotun et al, "Investigation of a Vitamin B 12 Conjugate as a PET Imaging Probe", Chemmedchem, DE, (20140417), vol. 9, No. 6, doi:10.1002/cmdc.201400048, ISSN 1860-7179, pp. 1244-1251, XP055350292.
Omlin, et al., "Androgen- and Ostrogen-biosynthesehemmer beim kastrationsresistenten Prostatakarzinom," 2012, Urologe, 51 pp. 8-14.
Omlin, et al., "Inhibitors of Androgen and Estrogen Biosynthesis in Castration-Resistant Prostate Cancer," English translation, 2012, Urologe, 51(1) pp. 8-14.
Oppostion Correspondence dated Jan. 6, 2025 in reference to the Request for Re-Examination of Australian Patent 2020201329 dated Dec. 13, 2024.
Osborne, et al., "A Prospective Pilot Study of 89Zr-J591/Prostate Specific Membrane Antigen Positron Emission Tomography in Men with Localized Prostate Cancer Undergoing Radical Prostatectomy," 2014, The Journal of Urology, 19195) pp. 1439-1445.
Oyama et al., "11C-Acetate PET Imaging of Prostate Cancer: Detection of Recurrent Disease at PSA Relapse," J Nucl Med 2003; 44:549-555.
Oyama, et al., "11C-Acetate PET Imaging of Prostate Cancer," 2002, Journal of Nuclear Medicine, 43(2) pp. 181-186.
Oyama, et al., "PET Imaging in Prostate Cancer," 2006, Hinyokika Kiyo, 52(6) pp. 503-505.
Paranjpe, P., et al., "Tumor-targeted bioconjugate based delivery of camptothecin: design, synthesis and in vitro evaluation," 2004, ScienceDirect Journal of Controlled Release, 100(2) pp. 275-292.
Parker, et al., "Design, production, and characterization of a single-chain variable fragment (ScFv) derived from the prostate specific membrane antigen (PSMA) monoclonal antibody J591," 2013, Protein Expression and Purification, 89(2) pp. 136-145.
Pathak, T., et al., "Enzymic Protecting Group Techniques in Organic Synthesis," 2000, Stereoselective Biocatalysis pp. 775-797.
Pavlicek, et al., "Glutamate Carboxypeptidase II: An Overview of Structural Studies and Their Importance for Structure-Based Drug Design and Deciphering the Reaction Mechanism of the Enzyme," 2012, Current Medicinal Chemistry, 19(9) pp. 1300-1309.

(56) References Cited

OTHER PUBLICATIONS

Pavlicek, et al., "Structural characterization of P1'-diversified urea-based inhibitors of glutamate carboxypeptidase II," 2014, Bioorganic & Medicinal Chemistry Letters, 24(10) pp. 2340-2345.
PCT International Search Report and Written Opinion for PCT/US2011/026238, mailed Apr. 27, 2011.
PCT International Search Report and Written Opinion for PCT/US2013/070007, mailed Mar. 5, 2014.
PCT International Search Report and Written Opinion prepared for PCT/US2019/027720, completed May 30, 2019.
PCT International Search Report for PCT/US2008/073375 dated Oct. 26, 2008.
PCT International Search Report for PCT/US2016/012653, completed Mar. 11, 2016.
PCT International Search Report/Written Opinion for PCT/US2009/061049, completed Mar. 15, 2010.
PCT International Search Report/Written Opinion for PCT/US2009/061067, completed May 28, 2010.
PCT Search Report & Written Opinion issued in App. No. PCT/US2014/065467, mailed Apr. 15, 2015.
PCT Search Report and Written Opinion prepared for PCT/US2019/051903, completed Oct. 25, 2019.
PCT Search Report and Written Opinion prepared for PCT/US2019/052161, completed Dec. 18, 2019.
PCT Search Report and Written Opinion prepared for PCT/US2021/018447, completed May 6, 2021.
Peltier, H., et al., "The Total Synthesis of Tubulysin D,"2006, Journal of the American Chemical Society, 128(50) pp. 16018-16019.
Perner, et al., "Prostate-specific membrane antigen expression as a predictor of prostate cancer progression," 2007, Human Pathology, 38(5) pp. 696-701.
Pillarsetty, et al., "2-18F-Fluoropropionic Acid as a PET Imaging Agent for Prostate Cancer," 2009, Journal of Nuclear Medicine, 50(10) pp. 1709-1714.
Pinto, et al., "Imaging in Prostate Cancer Staging: Present Role and Future Perspectives," 2012, Urology International, 88 pp. 125-136.
Pomper, M., et al., "11C-MCG: synthesis, uptake selectivity, and primate PET of a probe for glutamate carboxypeptidase II (NAALADase)," 2002, Molecular Imaging, 1(2) pp. 96-101.
Ponde, et al., "18F-Fluoroacetate: A Potential Acetate Analog for Prostate Tumor Imaging—In Vivo Evaluation of 18F-Fluoroacetate Versus 11C-Acetate," 2007, Journal of Nuclear Medicine, 48(3) pp. 420-428.
Poulsen, et al., "[18F] fluoromethylcholine (FCH) positron emission tomography/computed tomography (PET/CT) for lymph node staging of prostate cancer: a prospective study of 210 patients," 2012, BJU International, 110(11) pp. 1666-1671.
Poulsen, et al., "[18F]-fluorocholine positron-emission/computed tomography for lymph node staging of patients with prostate cancer: preliminary results of a prospective study," 2010, BJU International, 106(5) pp. 639-644.
Preusser, et al., "Castration-Resistant Prostate Cancer," English translation, 2012, Urologe, 51(1) pp. 27-31.
Preusser, et al., "Kastrationsresistentes Prostatakarzinom," 2012, Urologe, 51 pp. 27-31.
Pubchem, Compound summary for: CID 58099954, Aug. 19, 2012.
Radioisotopes in Medicine, from http://www.word-nuclearorg/information-library/non-power-nuclear applications/radioisotopes-research/radioisotopes-in-medicine.aspx, Dec. 28, 2016, pp. 1-20.
Rahbar, K. et al., "Delayed response after repeated 177Lu-PSMA-617 radioligand therapy in patients with metatstatic castration resistant prostate cancer," European Journal of Nuclear Medicine and Molecular Imaging, 2017, 45(2) pp. 243-246.
Hwang, et al., "N-3-[18F]Fluoropropylputrescine as Potential PET Imaging Agent for Prostate and Prostate Derived Tumors," 1989, Journal of Nuclear Medicine, 30(7) pp. 1205-1210.
Igerc, et al., "The value of 18F-Choline PET/CT in patients with elevated PSA-level and negative prostate needle biopsy for localisation of prostate cancer," 2008, European Journal of Nuclear Medicine and Molecular Imaging, 35(5) pp. 976-983.
International Search Report and Written Opinion for International Patent Application No. PCT/US2020/033584, mailed Aug. 14, 2020 (12 pages).
Istard Posters, 2012, European Journal of Nuclear Medicine and Molecular Imaging, 39(2) pp. 304-353.
Jackson, et al., "Design, Synthesis, and Biological Activity of a Potent Inhibitor of the Neuropeptidase N-Acetylated a-Linked Acidic Dipeptidase," 1996, Journal of Medicinal Chemistry, 39(2) pp. 619-622.
Jackson, P. and Slusher, B., "Design of NAALADase Inhibitors: A Novel Neuroprotective Strategy," 2001, Current Medicinal Chemistry, 8(8) pp. 949-957.
Jadvar, et al., "Glucose Metabolism of Human Prostate Cancer Mouse Xenografts," 2005, Molecular Imaging, 4(2) pp. 91-97.
Jadvar, et al., "Imaging evaluation of prostate cancer with 18F-fluorodeoxyglucose PET/CT: utility and limitations," 2013, European Journal of Nuclear Medicine and Molecular Imaging, 40 (Suppl 1) pp. S5-S10.
Jadvar, et al., "Molecular imaging of prostate cancer with 18F-fluorodeoxyglucose PET," 2009, Nature Reviews Urology, 6(6) pp. 317-323.
Jadvar, et al., "Molecular Imaging of Prostate Cancer: PET Radiotracers," 2012, AJR, 199 pp. 278-291.
Jambor, et al., "Functional Imaging of Localized Prostate Cancer Aggressiveness Using 11C-Acetate PET/CT and 1H-MR Spectroscopy," 2010, Journal of Nuclear Medicine, 51(11) pp. 1676-1683.
James, Shelly, "Urea based rhenium tricarbonyl dipeptide compounds as potential radiopharmaceuticals for PSMA imaging." Poster. INOR258.
Jayaprakash, S., et al. "Design and Synthesis of a PSMA inhibitor—doxorubicin Conjugate for Targeted Prostate Cancer Therapy," 2006, ChemMedChem, 1(3) pp. 299-302.
Jemaa, et al., "A Comparison of the Biological Features of Prostate Cancer with (PSA+, PSMA+) Profile according to RKIP," 2013, BioMed Research International, 2013(12) Article ID 409179,7 pages.
Jemaa, et al., "A novel regulation of PSMA and PSA expression by Q640X AR in 22Rv1 and LNCaP prostate cancer cells," 2013, Cell Biology International, 37(5) pp. 464-470.
Jemaa, et al., "Cellular distribution and heterogeneity of PSA and PSMA expression in normal, hyperplasia and human prostate cancer," 2013, La Tunisie Medicale, 91(7) pp. 458-463.
Jeong, et al., "Preparation of a Promising Angiogenesis PET Imaging Agent: 68Ga-Labeled c(RGDyK)-Isothiocyanatobenzyl-1,4,7-Triazacyclononane-1,4,7-Triacetic Acid and Feasibility Studies in Mice," 2008, The Journal of Nuclear Medicine, 49(5) pp. 830-836.
Jivan, S. et al. P 140: Fully automated preparation of [18FJCTT1057, a new prostate cancer imaging agent, prepared using the ORA Neptis Perform Synthesizer®. 22nd International Symposium on Radiopharmaceutical Sciences, Poster: S297, J Label Compd Radiopharm, 2017: 60 (Suppl. 1): S11-S640.
Kahkoska, "Vitamin B12-Based Bioconjugate Probes for in Vitro and in Vivo Imaging" (2013). Renee Crown University Honors Thesis Projects—All. 64. https://surface.syr.edu/honors_capstone/64.
Kahn, et al., "111Indium-Capromab Pendetide in the Evaluation of Patients with Residual or Recurrent Prostate Cancer After Radical Prostatectomy," 1998, The Journal of Urology, 159(6) pp. 2041-2047.
Kairemo K. et al., Lu-177-PSMA treatment for metastatic prostate cancer-case examples of miracle responses, Urology Herald, Jul. 3, 2018 , v. 6, No. 1, p. 65-75.
Kasperzyk, et al., "Prostate-Specific Membrane Antigen Protein Expression in Tumor Tissue and Risk of Lethal Prostate Cancer," Cancer Epidemiol Biomarkers Prey, 22(12) pp. 2354-2363.
Kasten, et al., "Targeting prostate cancer cells with PSMA inhibitor-guided gold nanoparticles," 2013, Bioorganic & Medicinal Chemistry Letters, 23(2) pp. 565-568.
Kaur, G., et al., "Biological evaluation of tubulysin A: a potential anticancer and antiangiogenic natural product," 2006, Biochemical Journal, 396(2) pp. 235-242.

(56) References Cited

OTHER PUBLICATIONS

Khreish, F. et al.225Ac-PSMA-617/1 77Lu-PSMA-617 tandem therapy of metastatic castration-resistant prostate cancer: pilot experience. European Journal of Nuclear Medicine and Molecular Imaging (2020) 47:721-728. https://doi.org/10. 1007/s00259-019-04612-0.
Kim, et al., "Tribody: Robust Self-Assembled Trimeric Targeting Ligands with High Stability and Significantly Improved Target-Binding Strength," 2013, Biochemistry, 52(41) pp. 7283-7294.
Kinoshita, et al., "Expression of Prostate-Specific Membrane Antigen in Normal and Malignant Human Tissues," 2006, World Journal of Surgery, 30(4) pp. 628-636.
Klotz, L. "Cancer overdiagnosis and overtreatment," 2012, Current Opinion in Urology, 22(3) pp. 203-209.
Klusak, et al., "Reaction Mechanism of Glutamate Carboxypeptidase II Revealed by Mutagenesis, X-ray Crystallography, and Computational Methods," 2009, Biochemistry, 48(19) pp. 4126-4138.
Korean Application Serial No. 10-2016-7015740, Notice of Preliminary Rejection mailed Nov. 19, 2020, (w/ English translation), 12 pgs.
Koseki, Y. et al., "Drug release is determined by the chain length of fatty acid-conjugated anticancer agent as one component of nanoprodrug." Bulletin of the Chemical Society of Japan. May 2016; 89(5): 540-5.
Kosuri, et al., "Review of Salvage Therapy for Biochemically Recurrent Prostate Cancer: The Role of Imaging and Rationale for Systemic Salvage Targeted Anti-Prostate-SpecificMembrane Antigen Radioimmunotherapy," 2012, Advances in Urology, 2012(6) Article ID 921674,8 pages.
Kothari, et al., "18F-labeled small molecule inhibitors of prostate specific membrane antigen (PSMA) for PET imaging of prostate cancer," 2012, Journal of Nuclear Medicine, 53(1) pp. 1721.
Kotzerke, et al., "PET for Prostate Cancer Imaging: Still a Quandary or the Ultimate Solution?," 2002, The Journal of Nuclear Medicine, 43(2) pp. 200-202.
Kovar, et al., "Pharmacokinetic and Biodistribution Assessment of a Near Infrared-Labeled PSMA-Specific Small Molecule in Tumor-Bearing Mice," 2014, Prostate Cancer, 2014 Article ID 104248, 10 pages.
Kozikowski, A., et al., "Design of Remarkably Simple, Yet Potent Urea-Based Inhibitors of Glutamate Carbozypeptidase II (NAALADase)," 2001, Journal of Medicinal Chemistry, 44(3) pp. 298-301.
Kozikowski, A., et al., "Synthesis of Urea-Based Inhibitors as Active Site Probes of Glutamate Carboxypeptodase II: Efficacy as Analgesic Agents," 2004, Journal of Medicinal Chemistry, 47(7) pp. 1729-1738.
Kratochwil, C et al. "Targeted alpha-Therapy of Metastatic Castration-Resistant Prostate Cancer with 225Ac-PSMA-617: Swimmer-Plot Analysis Suggests Efficacy Regarding Duration of Tumor Control"; J Nucl Med. 2018. vol. 59, No. 5, pp. 795-802, DOI: 10.2967/jnumed.117.203539, Jan. 11, 2018 (Jan. 11, 2018).
Kratochwil, C., et al., "[177Lu]Lutetium-labelled PSMA ligand-induced remission in a patient with metastatic prostate cancer," Eur J Nucl Med Mol Imaging, 2015, 42, 987-88.
Kratochwil, C., et al., "PSMA-Targeted Radionuclide Therapy of Metastatic Castration-Resistant Prostate Cancer with 177 Lu-Labeled PSMA-617," The Journal of Nuclear Medicine, Mar. 16, 2016, 57(8) pp. 1170-1176.
Kratochwil, et al. "225Ac-PSMA-617 for PSMA-Targeted a-Radiation Therapy of Metastatic Castration-Resistant Prostate Cancer." J Nucl Med 2016; 57:1941-1944. DOI: 10.2967/jnumed.116.178673.
Krohn, et al., "[68Ga]PSMA-HBED uptake mimicking lymph node metastasis in coeliac ganglia: an important pitfall in clinical practice," 2015, European Journal of Nuclear Medicine and Molecular Imaging, 42(2) pp. 210-214.
Kularatne, et al., "Design, Synthesis, and Preclinical Evaluation of Prostate-Specific Membrane Antigen Targeted 99mTc-Radioimaging Agents," 2009, Molecular Pharmaceuticals, 6(3) pp. 790-800.
Kularatne, S., et al., "Comparative Analysis of Folate Derived PET Imaging Agents with [18F]-2-Fluoro-2-deoxy-D-glucose Using Rodent Inflammatory Paw Model," 2013, Molecular Pharmaceutics, 10(8)pp. 3103-3111.
Kularatne, S., et al., "Prostate-specific membrane antigen targeted imaging and therapy of prostate cancer using a PSMA inhibitor as a homing ligand," 2009, Molecular Pharmaceutics, 6(3) pp. 780-789.
Kularatne, S., et al., "Synthesis and Biological Analysis of Prostate-Specific Membrane Antigen-Targeted Anticancer Prodrugs," 2010, Journal of Medicinal Chemistry, 53(21) pp. 7767-7777.
Kuru et al., "MRT-navigierte stereotaktische Prostatabiopsie," Urologe 2012-51:50-56.
Kuru, et al., "MRI Navigated Stereotactic Prostate Biopsy," English Translation, 2012, Urologe, 51(1) pp. 50-56.
Kwee, et al., "18F-choline PET/CT imaging of RECIST measurable lesions in hormone refractory prostate cancer," 2009, Annals of Nuclear Medicine, 23 pp. 541-548.
Lambert, et al., "Molecular Evolution of the Transferrin Receptor/Glutamate Carboxypeptidase II Family," 2007, Journal of Molecular Evolution, 64(1) pp. 113-128.
Farokhzad, O., et al., "Nanoparticle-Aptamer Bioconjugates: A New Approach for Targeting Prostate Cancer Cells," 2004, Cancer Research, 64(21) pp. 7668-7672.
Fay et al., "Blocking the PD-1/PD-L1 axis in advanced prostate cancer: are we moving in the right direction?", Ann Oncol, vol. 29, Jan. 1, 2018 (Jan. 1, 2018), pp. 1807-1813, XP055866909, DOI: 10.21037/atm.2019.01.37, Retrieved from the Internet: URL: https://repositorio.pucrs.br/dspace/bitstream/10923/17345/2/Blocking_the_PD_1_PD_L1_axis_in_advanced_prostate_cancer_are_we_moving_in_the_right_direction.pdf.
Fendler et al., "177Lu-PSMA Radioligand Therapy for Prostate Cancer." Journal of Nuclear Medicine Aug. 2017, 58(8) 1196-1200) (Year: 2017).
Fortmuller, et al., "Effective Targeting of Prostate Cancer by Lymphocytes Redirected by a PSMAx CD3 Bispecific Single-Chain Diabody," 2011, The Prostate, 71(6) pp. 588-596.
Fortuin, et al., "Value of PET/CT and MR Lymphography in Treatment of Prostate Cancer Patients With Lymph Node Metastases," 2012, International Journal of Radiation Oncology, Biology, Physics, 84(3) pp. 712-718.
Foss, C., et al. "Radiolabeled Small-molecule Ligands for Prostate-specific Membrane Antigen: In vivo Imaging in Experimental Models of Prostate Cancer," 2005, Clinical Cancer Research, 11(11) pp. 4022-4028.
Foss, et al., "GCPII Imaging and Cancer," 2012, Current Medicinal Chemistry, 19(9) pp. 1346-1359.
Foss, et al., "Synthesis and Validation of a Novel Small-Molecule Fluorescent Probe for PSMA Expression in Human Tumor Neovasculature," 2005, Abstract. Abstract ID: 362.
Franc, et al., "Detection and localization of carcinoma within the prostate using high resolution transrectal gamma imaging (TRGI) of monoclonal antibody directed at prostate specific membrane antigen (PSMA)—Proof of concept and initial imaging results," 2013, European Journal of Radiology, 82(11) pp. 1877-1884.
Frigerio, et al., "A single-chain fragment against prostate specific membrane antigen as a tool to build theranostic reagents for prostate cancer," 2013, European Journal of Cancer, 49(9) pp. 2223-2232.
Ghosh, et al., "Tumor Target Prostate Specific Membrane Antigen (PSMA) and its Regulation in Prostate Cancer," 2004, Journal of Cellular Biochemistry, 91(3) pp. 528-539.
Giovacchini, et al., "Predictive factors of [11C]choline PET/CT in patients with biochemical failure after radical prostatectomy," 2010, European Journal of Nuclear Medicine and Molecular Imaging, 37(2) pp. 301-309.
Gomez-Hens, A. and Aguilar-Caballos, M., "Long Wavelength Fluorophores: New Trends in Their Analytical Use," 2004, Trends in Analytical Chemistry, 23(2), pp. 127-136.
Goodman Jr., et al., "Interaction of prostate specific membrane antigen with clathrin and the adaptor protein complex-2," 2007, International Journal of Oncology, 31(5) pp. 1199-1203.
Graham, et al., "Radiofluorinated Derivatives of 2-(Phosphonomethyl)pentanedioiAcid as Inhibitors of Prostate Spe-

(56) References Cited

OTHER PUBLICATIONS cific Membrane Antigen (PSMA) for the Imaging of Prostate Cancer," 2012, Journal of Medicinal Chemistry, 55(22) pp. 9510-9520.
Grant et al., "Prostate Specific Membrane Antigen (PSMA) Regulates Angiogenesis Independently of VEGF during Ocular Neovascularization," PLoS One 7(7): e41285.
Greene, T., and Wuts, P., "Protective Groups ion Organic Synthesis," 2d edition, John Wiley & Sons, Inc. New York (1991).
Gregor, et al., "Induction of autoantibodies to syngeneic prostate-specific membrane antigen by xenogeneic vaccination," 2005, International Journal of Cancer, 116(3) pp. 415-421.
Haberkorn, et al., "Mechanistic and high-throughput approaches for the design of molecular imaging probes and targeted therapeutics," 2014, Clinical and Translational Imaging, 2 pp. 33-41.
Haffner, et al., "Prostate-specific membrane antigen expression in the neovasculature of gastric and colorectal cancers," 2009, Human Pathology, 40(12) pp. 1754-1761.
Hain, et al., "Positron emission tomography for urological tumours," 2003, BJU International, 92(2) pp. 159-164.
Hamilou et al., "Treatment of Castration-naive Metastatic Prostate Cancer" European Urology Focus, 2017, vol. 3, No. 6, pp. 518-521. (Year: 2017).
Hara, et al., "11C-Choline and 2-Deoxy-2-[18F]Fluoro-D-Glucose in Tumor Imaging with Positron Emission Tomography," 2002, Molecular Imaging and Biology, 4(4) pp. 267-273.
Hara, et al., "Development of 18F-Fluoroethylcholine for Cancer Imaging with PET: Synthesis, Biochemistry, and Prostate Cancer Imaging," 2002, Journal of Nuclear Medicine, 43(2) pp. 187-199.
Hara, et al., "PET Imaging of Prostate Cancer Using Carbon-11-Choline," 1998, Journal of Nuclear Medicine, 39(6) pp. 990-995.
Harada, et al., "Preparation of Asymmetric Urea Derivatives that Target Prostate-Specific Membrane Antigen for SPECT Imaging," 2013, Journal of Medicinal Chemistry, 56(20) pp. 7890-7901.
Haseman, M., et al., "Capromab Pendetide Imaging of Prostate Cancer," 2009, Cancer Biotherapy and Radiopharmaceuticals, 15(2) pp. 131-140.
Heidenreich, A., "Immunotherapy For Metastatic Prostate Cancer-Do We Really Need This?," English translation (Abstract Only), 2012, Urologe, 51(1) pp. 32-38.
Heidenreich, A., "Immuntherapie beim metastasierten Prostatakarzinom—brauchen wir diese wirklich?," 2012, Urologe, 51 pp. 32-38.
Henne, W., et al., "Synthesis and activity of a folate peptide camptothecin prodrug," 2006, ScienceDirect, Bioorganic & Medical Chemistry Letters 16(20) pp. 5350-5355.
Henry, et al., "A Prostate-Specific Membrane Antigen-Targeted Monoclonal Antibody—Chemotherapeutic Conjugate Designed for the Treatment of Prostate Cancer," 2004, Cancer Research, 64(21) pp. 7995-8001.
Hillier, et al., "[1311] MIP-1466, a small molecule prostate-specific membrane antigen (PSMA) inhibitor for targeted radiotherapy of prostate cancer (PCa),"2012, Journal of Nuclear Medicine, 53(1) pp. 170.
Hillier, et al., "1231-MIP-1072, a Small-Molecule Inhibitor of Prostate-Specific Membrane Antigen, Is Effective at Monitoring Tumor Response to Taxane Therapy," 2011, Journal of Nuclear Medicine, 52(7) pp. 1087-1093.
Hillier, et al., "99mTc-Labeled Small-Molecule Inhibitors of Prostate-Specific Membrane Antigen for Molecular Imaging of Prostate Cancer," 2013, Journal of Nuclear Medicine, 54(8) pp. 1369-1376.
Hillier, S., et al., "Preclinical Evaluation of Novel Glutamate-Urea-Lysine Analogues That Target Prostate-Specific Membrane Antigen as Molecular Imaging Pharmaceuticals for Prostate Cancer," 2009, Cancer Research, 69(17) pp. 6932-6940.
Hlouchova, et al., "Biochemical characterization of human glutamate carboxypeptidase III," 2007, Journal of Neurochemistry, 101(3) pp. 682-696.
Hlouchova, et al., "GCPII Variants, Paralogs and Orthologs," 2012, Current Medicinal Chemistry, 19(9) pp. 1316-1322.
Hlouchova, et al., "Structural insight into the evolutionary and pharmacologic homology of glutamate carboxypeptidases II and III," 2009, FEBS Journal, 276)16) pp. 4448-4462.
Ho, et al., "Molecular Imaging, Pharmacokinetics, and Dosimetry of 111In-AMBA in Human Prostate Tumor-Bearing Mice," 2011, Journal of Biomedicine and Biotechnology, Article ID 101497,8 pages.
Hofman, M.S., et al., "[177Lu]Lu-PSMA-617 versus cabazitaxel in patients with metastatic castration-resistant prostate cancer (TheraP): a randomised, open-label, phase 2 trial," Published Online at The Lancet, Articles, Feb. 11, 2021, pp. 1-8.
Holland, et al., "89Zr-DFO-J591 for ImmunoPET of Prostate-Specific Membrane Antigen Expression In Vivo," 2010, Journal of Nuclear Medicine, 51(8) pp. 1293-1300.
Hong, et al., "Positron emission tomography imaging of prostate cancer," 2010, Amino Acids, 39(1) pp. 11-27.
Hospers, et al., "PET Imaging of Steroid Receptor Expression in Breast and Prostate Cancer," 2008, Current Pharmaceutical Design, 14(28) pp. 3020-3032.
Huang, et al., "Improving the Biodistribution of PSMA-Targeting Tracers With Highly Negatively Charged Linker," 2014, The Prostate, 74(7) pp. 702-713.
Huang, et al., "PSMA-Targeted Stably Linked Dendrimer-Glutamate Urea-Methotrexate' as a Prostate Cancer Therapeutic," 2014, Biomacromolecules, 15(3) pp. 915-923.
Humblet, et al., "High-affinity Near-infrared Fluorescent Small-molecule Contrast Agents for In Vivo Imaging of Prostate-specific Membrane Antigen," 2005, Molecular Imaging, 4(4) pp. 448-462.
Humblet, et al., "Multivalent Scaffolds for Affinity Maturation of Small Molecule Cell Surface Binders and Their Application to Prostate Tumor Targeting," 2009, Journal of Medicinal Chemistry , 52(2) pp. 544-550.
Humblet, V., et al., "An HPLC/mass spectrometry platform for the development of multimodality contrast agents and targeted therapeutics: prostate-specific membrane antigen small molecule derivatives," 2006, Contrast Media and Molecular Imaging, 1(5) pp. 196-211.
Husarik, et al., "Evaluation of [18F]-choline PET/CT for staging and restaging of prostate cancer," 2008, European Journal of Nuclear Medicine and Molecular Imaging, 35 pp. 253-263.
Hwang, et al., "Imaging Prostate Derived Tumors with PET and N-(3-[18F]Fluoropropyl)putrescine," 1990, Nuclear Medicine and Biology, 17(6) pp. 525-532.
Chen, et al., "PSMA-Targeted Theranostic Nanoplex for Prostate Cancer Therapy," 2012, ACS Nano, 6(9) pp. 7752-7762.
Chen, et al., "Synthesis and Biological Evaluation of Low Molecular Weight Fluorescent Imaging Agents for the Prostate-Specific Membrane Antigen," 2012, Bioconjugate Chemisty, 23(12) pp. 2377-2385.
Chen, Y., et al., "Radiohalogenated Prostate-Specific Membrane Antigen (PSMA)-Based Ureas as Imaging Agents for Prostate Cancer," 2008, Journal of Medicinal Chemistry, 51(24), pp. 7933-7943.
Chopra, A., "68Ga-Labeled 2-{3-[5-(7-{1-benzyloxycarbonyl-5-[2-(4,7, 10-triscarboxymethyl-1,4,7, 10-tetraazacyclododec-1-I)acetylamino]pentylcarbamoyl}-heptanoylamino)-1-carboxypentyl]ureido}pentanedioic acid," 2010, Molecular Imaging and Contrast Agent Database (MICAD), pp. 2004-2013.
Chuu, et al., "Androgen suppresses proliferation of castrationresistant LNCaP 104-R2 prostate cancer cells through androgen receptor, Skp2, and c-Myc," 2011, Cancer Science, 102(11) pp. 2022-2028.
Cimitan, et al., "[18F]fluorocholine PET/CT imaging for the detection of recurrent prostate cancer at PSA relapse: experience in 100 consecutive patients," 2006, European Journal of Nuclear Medicine and Molecular Imaging, 33 pp. 1387-1398.
ClinicalTrials.gov, "99mTc-MIP-1404 for Imaging Prostate Cancer: Phase I Clinical Study to Assess the Image Quality of a Simplified Kit Formulation Compared to a Multi-step Preparation of 99mTc-MIP-1404," ClinicalTrials.gov Identifier: NCT01654874, available online at: https://clinicaltrials.gov/ct2/show/NCT01654874.

(56) References Cited

OTHER PUBLICATIONS

ClinicalTrials.gov, "A Phase 1 Pilot Study of 99mTc-MIP-1404 SPECT/CT Imaging to Histology in Men With Prostate Cancer," Identifier: NCT01615406, available online at: https://clinicaltrials.gov/ct2/show/NCT01615406.
ClinicalTrials.gov, "A Phase 2 Study With MIP-1404 in Men With High-Risk PC Scheduled for RP and EPLND Compared to Histopathology," ClinicalTrials.gov Identifier: NCT01667536, available online at: https://clinicaltrials.gov/ct2/show/NCT01667536?id=NCT01667536.
ClinicalTrials.gov, "Pilot Study of 99mTc-MIP-1404 SPECT/CT Imaging in Men With Prostate Cancer Undergoing Prostatectomy and/or Pelvic Lymph Node Dissection," ClinicalTrials.gov Identifier: NCT01572701, available online at: https://clinicaltrials.gov/ct2/show/NCT01572701.
ClinicalTrials.gov, "PSMA-directed endoRadiotherapy of castration reSISTant Prostate Cancer (Resist-PC). A Phase II clinical trial." Clinical Trial Results Website, Study Start Date Jul. 2017, Study Competition Date Jan. 2020, 24 pages.
Colabufo, et al., "PB183, a sigma receptor ligand, as a potential PET probe for the imaging of prostate adenocarcinoma," 2008, Bioorganic & Medicinal Chemistry Letters, 18(6) pp. 1990-1993.
Cole, A., et al., "Cancer theranostics: the rise of targeted magnetic nanoparticles," 2011, Trends in Biotechnology, 29 (7) pp. 323-332.
Cunha, et al., "Tissue-specificity of prostate specific antigens: Comparative analysis of transcript levels in prostate and non-prostatic tissues," 2006, Cancer Letters, 236(2) pp. 229-238.
Dahl, et al., "Sarcosine induces increase in HER2/neu expression in androgen-dependent prostate cancer cells," 2011, Molecular Biology Reports, 38 pp. 4237-4243.
Davis, M., et al., "Crystal Structure of Prostate-Specific Membrane Antigen, A Tumor Marker and Peptidase," 2005, Proceedings of the National Academy of Sciences of the United States of America, 102(17) pp. 5981-5986.
De Santis, et al., "Role of Chemotherapy in Castration Resistant Prostate Cancer," 2012, English translation, Urologe, 51(1) pp. 39-43.
De Santis, et al., "Rolle der Chemotherapie beim kastrationsresistenten Prostatakarzinom," 2012, Urologe, 51 pp. 39-43.
Debnath et al., "PSMA-targeting imaging and theranostic agents—Current status and future perspective." International journal of molecular sciences. Jan. 21, 2022;23(3):1158. (Year: 2022).
Definition of ligand, Random House Kernerman Webster's College Dictionary, downloaded on Jan. 25, 2014 from http://www.thefreedictionary.com/ligand, 1 page.
Degrado, et al., "Synthesis and Evaluation of 18F-Labeled Choline Analogs as Oncologic PET Tracers," 2001, Journal of Nuclear Medicine, 42(12) pp. 1805-1814.
Degrado, et al., "Synthesis and Evaluation of 18F-labeled Choline as an Oncologic Tracer for Positron Emission Tomography: Initial Findings in Prostate Cancer," 2000, Cancer Research, 61(1) pp. 110-117.
Dimitrakopoulou-Strauss, et al., "PET Imaging of Prostate Cancer with 11C-Acetate," 2003, Nuclear Medicine, 44(4) pp. 556-558.
Divyya, et al., "GCPII modulates oxidative stress and prostate cancer susceptibility through changes in methylation of RASSF1, BNIP3, GSTP1 and Ec-SOD," 2013, Mol Biol Rep, 40 pp. 5541-5550.
Drake et al., "Blocking the regulatory T cell molecule LAG-3 augments in vivo anti-tumor immunity in an autochthonous model of prostate cancer", Journal of Clinical Oncology, Grune & Stratton, vol. 24, No. 18, suppl, Jun. 20, 2006 (Jun. 20, 2006), p. 2573, XP009138507, ISSN: 0732-183x.
Dumas, et al., "Molecular Expression of PSMA mRNA and Protein in Primary Renal Tumors," 1999, International Journal of Cancer, 80(6) pp. 799-803.
Dusich, et al., "General Approach for the Preparation of Fluorescent PSMA/GCPII Inhibitors," 2006, Abstract. Abstract ID: 470, Poster board space: 29.
Eder, et al., "Novel Preclinical and Radiopharmaceutical Aspects of [68Ga]Ga-PSMA-HBED-CC: A New PET Tracer for Imaging of Prostate Cancer," 2014, Pharmaceuticals, 7(7) pp. 779-796.
Eder, et al., "Pharmacokinetic Properties of Peptidic Radiopharmaceuticals: Reduced Uptake of (EH)3-Conjugates in Important Organs," 2013, Nuclear Medicine, 54(8) pp. 1-4.
Eder, et al., "Preclinical Evaluation of a Bispecific Low-Molecular HeterodimerTargeting Both PSMA and GRPR for Improved PET Imaging and Therapy of Prostate Cancer," 2014, The Prostate, 74(6) pp. 659-668.
Eder, et al., "PSMA as a target for radiolabelled small molecules," 2013, European Journal of Nuclear Medicine and Molecular Imaging, 40 pp. 819-823.
Eiber, et al., "68Ga-PSMA PET/MR with multimodality image analysis for primary prostate cancer," 2015, Abdom Imaging, 40(6) pp. 1769-1771.
El-Zaria, et al., "Preparation and evaluation of carborane-derived inhibitors of prostate specific membrane antigen (PSMA)," 2014, Dalton Transactions, 43 pp. 4950-4961.
Elsasser-Beile, et al., "A New Generation of Monoclonal and Recombinant Antibodies Against Cell-Adherent Prostate Specific Membrane Antigen for Diagnostic and Therapeutic Targeting of Prostate Cancer," 2006, The Prostate, 66(13) pp. 1359-1370.
Elsasser-Beile, et al., "PET Imaging of Prostate Cancer Xenografts with a Highly Specific Antibody against the Prostate-Specific Membrane Antigen," 2009, Journal of Nuclear Medicine, 50(4) pp. 606-611.
Elsasser-Beile, et al., "Targeted Therapies for Prostate Cancer Against the Prostate Specific Membrane Antigen," 2009, Current Drug Targets, 10(2) pp. 118-125.
Emmett, L. et al. ENZA-p: A randomized phase II trial using PSMA as a therapeutic agent and prognostic indicator in men with metastatic castration-resistant prostate cancer treated with enzalutamide. Poster. J. Clin. Oneal. 2021, 39, TPS177.
Emmett, L. et al. Lutetium 177 PSMA radionuclide therapy for men with prostate cancer: a review of the current literature and discussion of practical aspects of therapy. J Med Radiat Sci. Mar. 2017;64(1):52-60. doi: 10.1002/jmrs.227.
Emonds, et al., "Do androgens control the uptake of 18F-FDG, 11C-choline and 11C-acetate in human prostate cancer cell lines?," 2011, European Journal of Nuclear Medicine and Molecular Imaging, 38(10) pp. 1842-1853.
European Patent Application No. EP 14861854, by Endocyte, Inc et al.: Partial Supplementary Search Report with Opinion; Dated May 19, 2017 (15 pages).
European Search Report in EP 18175078.7 dated Sep. 14, 2018.
European Search Report in EP 18184296 mailed Feb. 12, 2019.
European Search Report in EP 18203547 mailed Apr. 4, 2019.
European Search Report in EP 20180928, completed Dec. 7, 2020.
European Supplemental Search Report, prepared for EP Application No. 21757774, completed Jun. 5, 2024.
Evans, et al., "Noninvasive measurement of androgen receptor signaling with a positron-emitting radiopharmaceutical that targets prostate-specific membrane antigen," 2011, Proceedings of the National Academy of Sciences of the United States of America, 108(23) pp. 9578-9582.
Extended European Search Report for application No. EP21150716.5, mailed Jul. 23, 2021.
Fair, et al., "Prostate-Specific Membrane Antigen," 1997, The Prostate, 32(2) pp. 140-148.
Fall, et al., "Prostate-Specific Antigen Levels as a Predictor of Lethal Prostate Cancer," 2007, Journal of the National Cancer Institute, 99(7) pp. 526-532.
Fani, M. et al. In vivo imaging of folate receptor positive tumor xenografts using novel 68Ga-NODAGA-folate conjugates. Mol Pharm. May 7, 2012;9(5):1136-45.

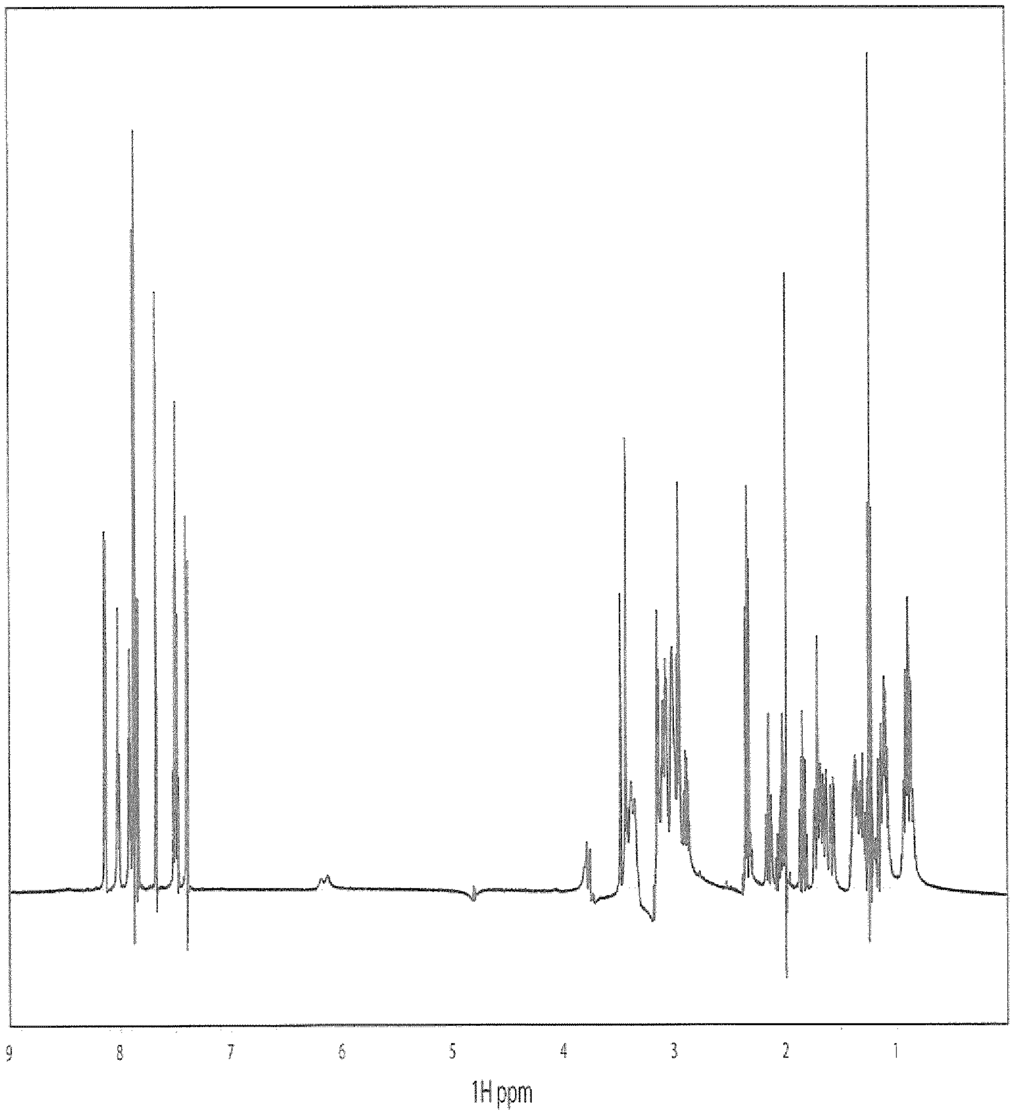
9
8
7
6
5
4
3
2
1
1H ppm

SYNTHESIS OF PROSTATE SPECIFIC MEMBRANE ANTIGEN (PSMA) LIGANDS

CROSS-REFERENCE TO RELATED APPLICATIONS

This application is a national stage entry of PCT International Application No. PCT/EP2021/082323, filed Nov. 19, 2021, which claims the benefit of European Patent Application No. 20208556.9, filed Nov. 19, 2020, the disclosure of each of which are each hereby incorporated by reference in their entirety.

TECHNICAL FIELD

The present disclosure relates to the synthesis of prostate specific membrane antigen (PSMA) ligands that are useful in the treatment of diseases like cancer. In particular, the disclosure relates to a method for synthesizing PSMA ligands having a glutamate-urea-lysine (GUL) moiety and a chelating agent that can comprise a radiometal.

BACKGROUND ART

Prostate cancer is one of the most widespread cancers in the US and in Europe. In particular, metastatic prostate cancer (mCRPC) is associated with poor prognosis and diminished quality of life.

Recently, a new development stream for treating prostate cancer is represented by the Radio Ligand Therapy (RLT) based on PSMA ligands, as PSMA is considered to be a suitable target for imaging and therapy due to its over-expression in primary cancer lesions and in soft-tissue/bone metastatic disease. Also, PSMA expression seems to be even higher in the most aggressive castration-resistant variants of the disease, which represents a patient population with high unmet medical need. (Marchal et al., Histol Histopathol, 2004, July; 19(3):715-8; Mease et al., Curr Top Med Chem, 2013, 13(8):951-62).

Among many small-molecule ligands targeting PSMA, the urea-based low molecular weight agents have been the most extensively investigated ones. These agents were shown to be suitable for prostate cancer clinical assessment as well as for PRRT therapy (Kiess et al., Q J Nucl Med Mol Imaging, 2015; 59:241-68). Some of these agents have glutamate-urea-lysine (GUL) as the targeting scaffold. A class of molecules was created following the strategy to attach a linker between the chelator and GUL moiety. This approach allows the urea to reach the binding site while keeping the metal chelated portion on the exterior of the binding site. This strategy was successful in xenograft PSMA positive tumors due to its demonstrated high uptake and retention as well as fast renal clearance (Banerjee et al., J Med Chem, 2013; 56:6108-21).

Moreover, specific compounds, like $^{177}$Lu-PSMA-617, have been widely studied. Different studies show that $^{177}$Lu-PSMA-617 is a promising radiopharmaceutical in the treatment of prostate cancer (Delker et al., European Journal of Nuclear Medicine and Molecular Imaging (2016), 43(1), 42-51; Yadav et al., European Journal of Nuclear Medicine and Molecular Imaging (2017), 44(1), 81-91).

Because of the interest in urea-based PSMA ligands, and in PSMA-617 in particular, there is a need to provide synthesis methods that are cost-effective and that can deliver important quantities of product with a high purity.

SUMMARY OF THE DISCLOSURE

The present disclosure relates to a method for synthesizing a PSMA ligand that is useful in the treatment of diseases like cancer, and in particular prostate cancer.

The present disclosure also relates to a method for synthesizing a compound of formula (I), or a pharmaceutically acceptable salt thereof, using solid phase synthesis:

(I)

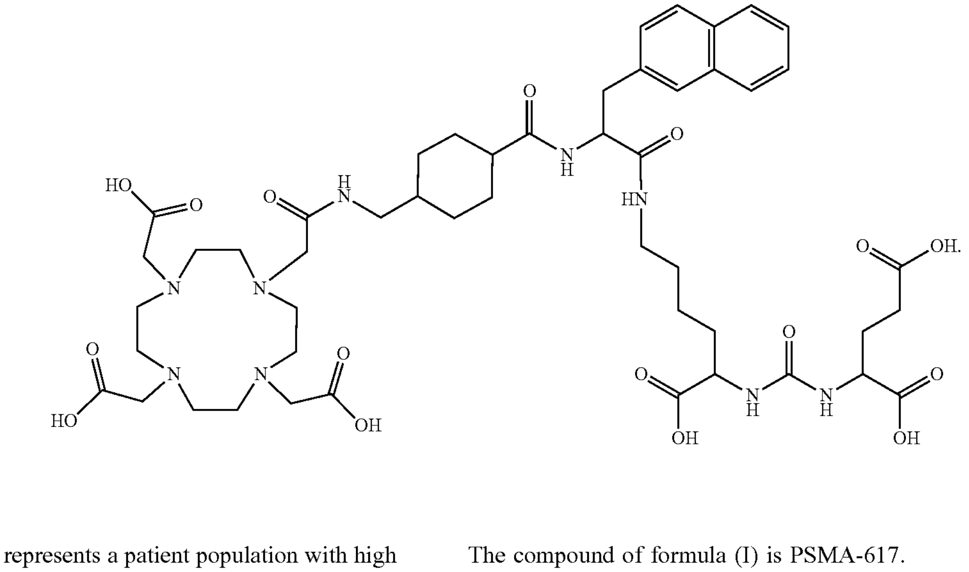

The compound of formula (I) is PSMA-617.

According to a first embodiment, the method comprises at least one of the following steps:

a) contacting a supported, preferably a resin-based, compound of formula (II)

(II)

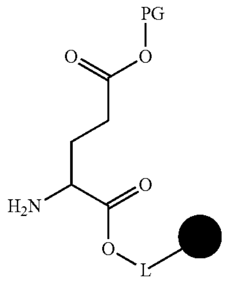

with a compound of formula (III)

(III)

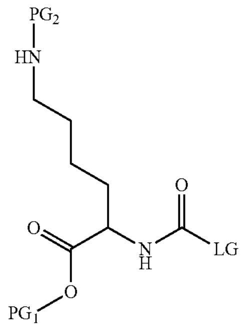

to provide a supported, preferably a resin-based, compound of formula (IV)

(IV)

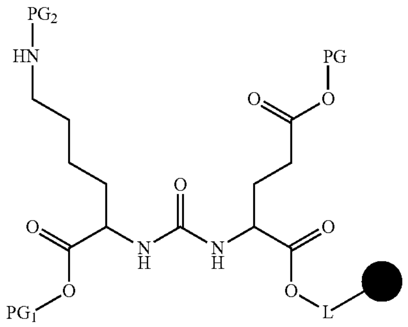

b) contacting the supported, preferably the resin-based, compound of formula (IV) with a deprotecting agent to provide a supported, preferably a resin-based, compound of formula (V)

(V)

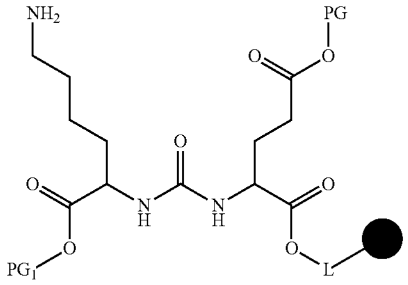

c) contacting the supported, preferably the resin-based, compound of formula (V) with a compound of formula (VI)

(VI)

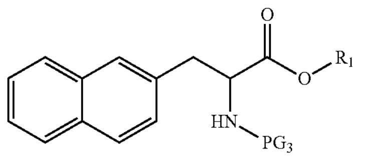

to provide a supported, preferably a resin-based, compound of formula (VII)

(VII)

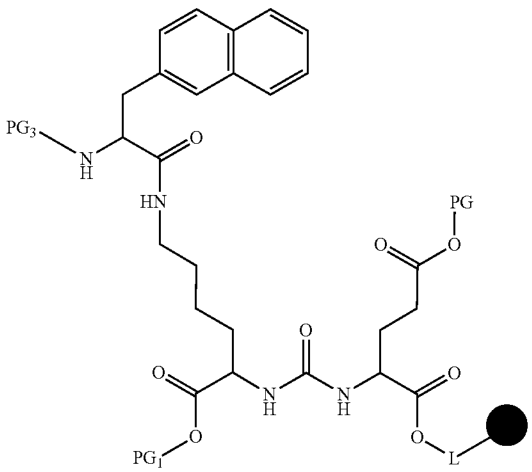

d) contacting the supported, preferably the resin-based, compound of formula (VII) with a deprotecting agent to provide a supported, preferably a resin-based, compound of formula (VIII)

(VIII)

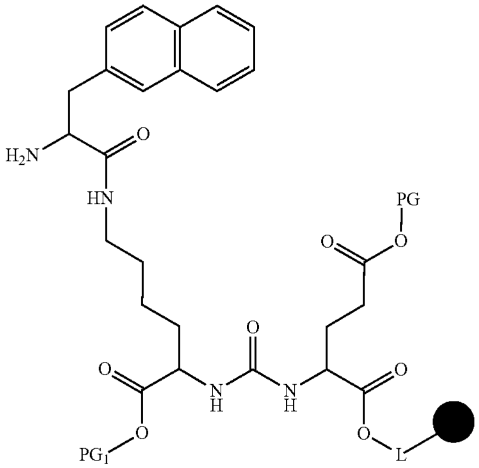

e) contacting the supported, preferably the resin-based, compound of formula (VIII) with a compound of formula (IX)

(IX)

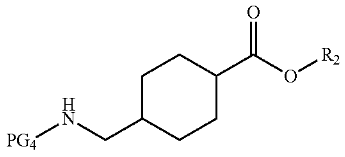

to provide a supported, preferably a resin-based, compound of formula (X)

(X)

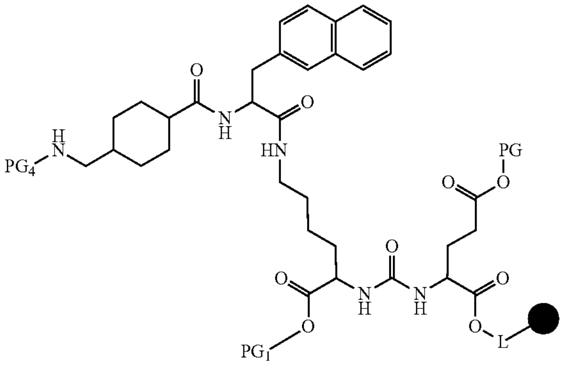

f) contacting the supported, preferably the resin-based compound of formula (X) with a deprotecting agent to provide a supported, preferably a resin-based, compound of formula (XI)

(XI)

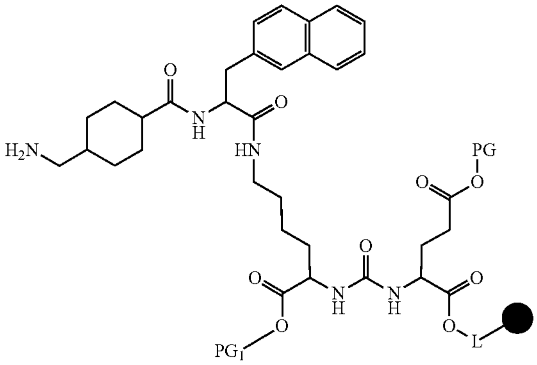

g) contacting the supported, preferably the resin-based, compound of formula (XI) with a compound (XII)

(XII)

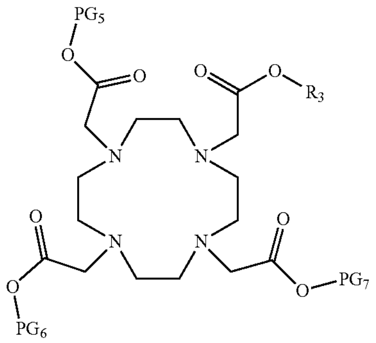

to provide a supported, preferably a resin-based, compound of formula (XIII)

(XIII)

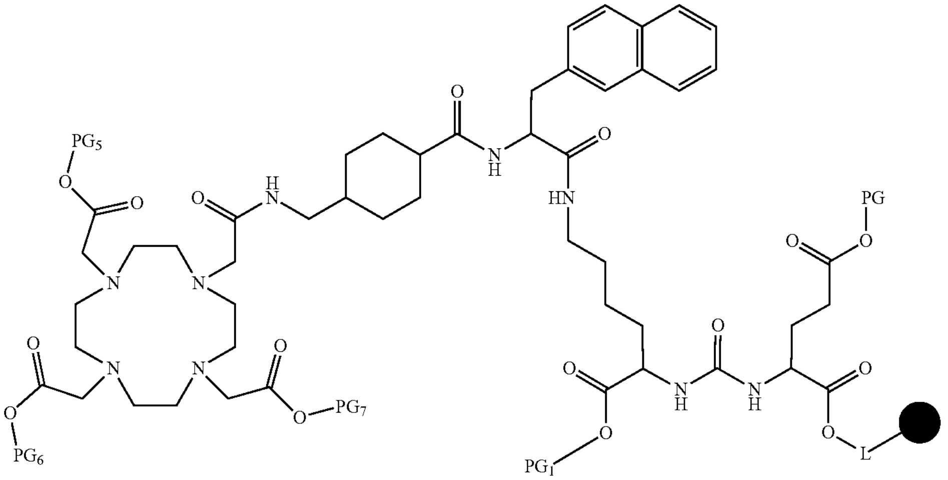

h) contacting the supported, preferably the resin-based, compound of formula (XIII) with a cleavage reagent, and optionally with a deprotecting agent, to provide the compound of formula (I), or a pharmaceutically acceptable salt thereof;

wherein

PG, PG1, PG5, PG6 and PG7 are each independently a carboxyl protecting group;

L is a linker;

PG2, PG3 and PG4 are each independently an amino protecting group;

R1, R2 and R3 are each independently H, or an activating ester group, and

LG is a leaving group selected from the group the group consisting of imidazole, halogens and activating ester groups.

According to a second embodiment, the method comprises at least one of the following steps:

a') contacting a supported, preferably a resin-based, compound of formula (II')

(II')

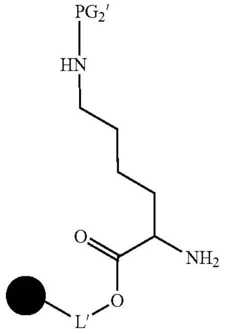

with a compound of formula (III')

(III')

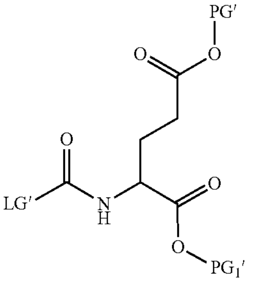

to provide a supported, preferably a resin-based, compound of formula (IV')

(IV')

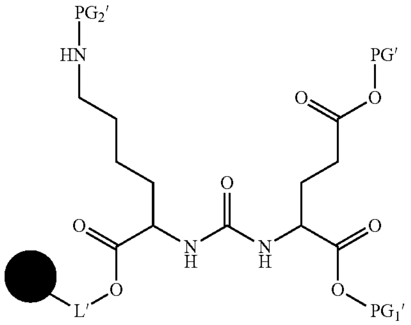

b') contacting the supported, preferably the resin-based, compound of formula (IV') with a deprotecting agent to provide a supported, preferably a resin-based, compound of formula (V')

(V')

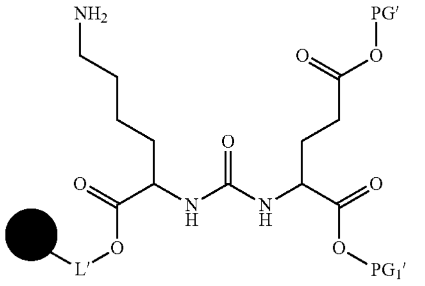

c') contacting the supported, preferably the resin-based, compound of formula (V') with a compound of formula (VI')

(VI')

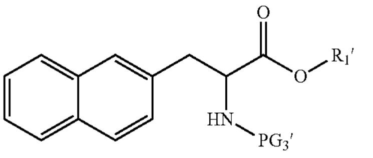

to provide a supported, preferably a resin-based, compound of formula (VII')

(VII')

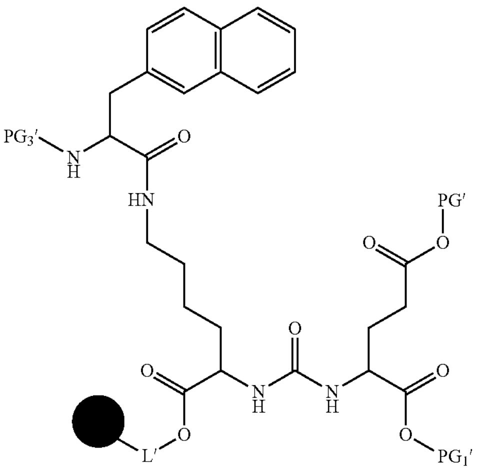

d') contacting the supported, preferably the resin-based, compound of formula (VII') with a deprotecting agent to provide a supported, preferably a resin-based, compound of formula (VIII')

(VIII')

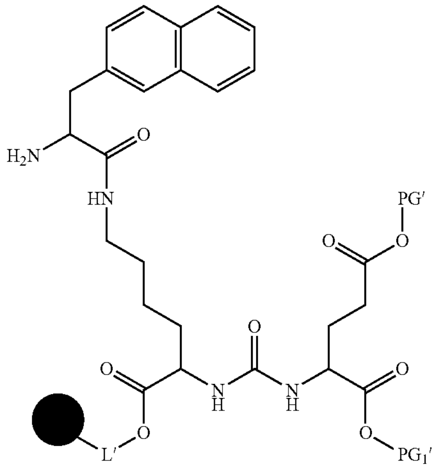

e') contacting the supported, preferably the resin-based, compound of formula (VIII') with a compound of formula (IX')

(IX')

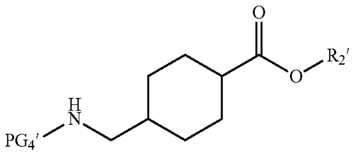

to provide a supported, preferably a resin-based, compound of formula (X')

(X')

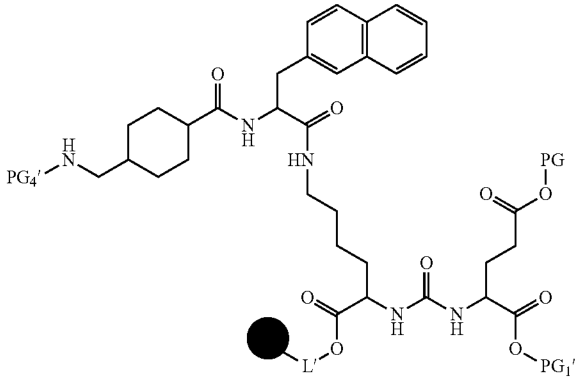

f') contacting the supported, preferably the resin-based, compound of formula (X') with a deprotecting agent to provide a supported, preferably a resin-based, compound of formula (XI')

(XI')

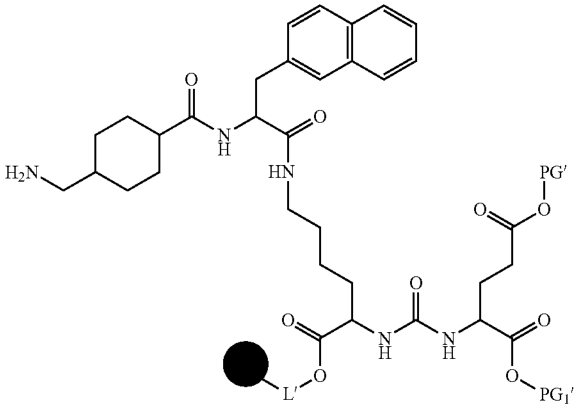

g') contacting the supported, preferably the resin-based, compound of formula (XI') with a compound (XII')

(XII')

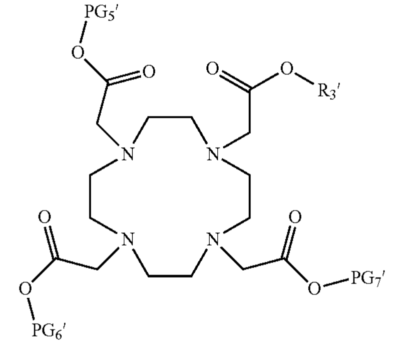

to provide a supported, preferably a resin-based, compound of formula (XIII')

(XIII')

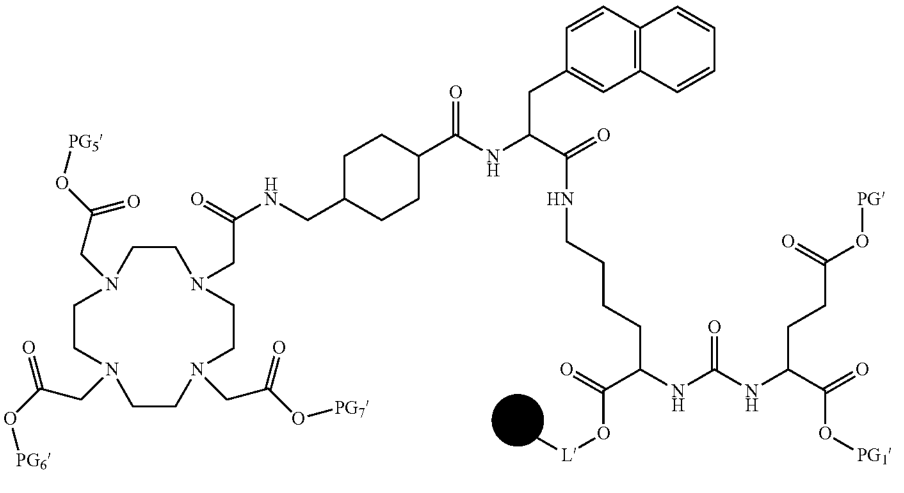

h') contacting the supported, preferably the resin-based, compound of formula (XIII') with a cleavage reagent, and optionally with a deprotecting agent, to provide the compound of formula (I), or a pharmaceutically acceptable salt thereof, wherein PG', PG1', PG5', PG6' and PG7' are each independently a carboxyl protecting group;

L' is a linker;

PG2', PG3' and PG4' are each independently an amino protecting group;

R1', R2' and R3' are each independently H or an activating ester group, and

LG' is a leaving group selected from the group consisting of imidazole, halogens and activating ester groups.

The fact that the synthesis is performed using solid phase synthesis allows for an efficient synthesis which is cost-effective. In particular, the overall yield of the synthesis can be greater than or equal to 20%, based on the supported starting material, compound (II) or (II').

DETAILED DESCRIPTION

Definitions

As used herein, the terms "solid phase synthesis" refer to a synthesis of chemical compounds whereby the reactant molecule is chemically bound to an insoluble material (a solid support, typically a resin) and reagents are added in the solution-phase. The reactant molecule is usually chemically bound to the solid support through a linker. Solid phase synthesis is commonly used to synthesize peptide, the person skilled in the art is therefore familiar with the techniques and apparatus used to perform solid phase synthesis. In solid phase peptide synthesis, an amino acid or peptide is bound, usually via the C-terminus, to a solid support. New amino acids are added to the bound amino acid or peptide via coupling reactions. Due to the possibility of unintended reactions, protection groups are typically used. The use of solid phase synthesis makes it possible to isolate and purify intermediates by simple filtration and rinsing, avoiding long and costly isolation and purification of intermediates.

As used herein, the terms "supported compound" refer to a compound which is chemically bound to an insoluble material, typically a resin.

As used herein, the terms "resin-based compound" refer to a compound that is chemically bound to a resin, which is a solid support. The resin-based compound is used in solid phase synthesis.

As used herein, the term "linker" refers to a divalent moiety connecting the reactant molecule to the insoluble material.

As used herein, the terms "protecting group" refer to a chemical substituent which can be selectively removed by readily available reagents which do not attack the regenerated functional group or other functional groups in the molecule. Suitable protecting groups are known in the art and continue to be developed. Suitable protecting groups may be found, for example in Wutz et al. ("Greene's Protective Groups in Organic Synthesis, Fourth Edition," Wiley-Interscience, 2007).

Protecting groups for protection of the carboxyl group, as described by Wutz et al. (pages 533-643), are used in certain embodiments. In some embodiments, the protecting group is removable by treatment with acid. Representative examples of carboxyl protecting groups include, but are not limited to, benzyl, p-methoxybenzyl (PMB), tertiary butyl (t-Bu), methoxymethyl (MOM), methoxyethoxymethyl (MEM), methylthiomethyl (MTM), tetrahydropyranyl (THP), tetrahydrofuranyl (THF), benzyloxymethyl (BOM), trimethylsilyl (TMS), triethylsilyl (TES), t-butyldimethylsilyl (TBDMS), and triphenylmethyl (trityl, Tr). Persons skilled in the art will recognize appropriate situations in which protecting groups are required.

Protecting group for protection of the amino group as described by Wutz et al. (pages 696-927), are used in certain embodiments. Representative examples of amino protecting groups include, but are not limited to, t-butyloxycarbonyl (Boc), 9-fluorenyl methoxycarbonyl (Fmoc), allyloxycarbonyl (alloc), N-(1-(4,4-dimethyl-2,6-dioxocyclohexylidene) ethyl) (Dde), 1-(1-Adamantyl)-1-Methylethoxycarbonyl (Adpoc), N-(1-(4,4-dimethyl-2,6-dioxocyclohex-1-ylidene)-3-methylbutyl) (ivDde), monomethoxytrityl (MMt) and 4-methyltrityl (Mtt). Persons skilled in the art will recognize appropriate situations in which protecting groups are required.

As used herein, the terms "activating ester group" refers to an electron-withdrawing group used to activate the ester function and make it more susceptible to nucleophilic attack. Active esters are commonly used in organic chemistry. Among activating ester groups, one can cite succinimidyl, p-nitrophenyl, tetrafluorophenyl, 3,4-dihydro-4-oxo-1,2,3-benzotriazine-3-yl, pentafluorophenyl, and 2,4,5-trichlorophenyl.

Various embodiments of the disclosure are described herein. It will be recognized that features specified in each embodiment may be combined with other specified features to provide further embodiments.

The present disclosure encompasses the compounds of formula (I)-(XIII) and the compounds of formula (II')-(XIII'), their stereoisomers, tautomers, enantiomers, diastereomers, racemates or mixtures thereof, and their hydrates, solvates or pharmaceutically acceptable salts.

The terms "pharmaceutically acceptable salts" refers to salts that retain the biological effectiveness and properties of the compounds of this disclosure and, which typically are not biologically or otherwise undesirable. Examples of pharmaceutically acceptable salts include trifluoroacetic acid (TFA), acetate or hydrochloride salts.

Synthesis of the Compound of Formula (I)

The present disclosure also relates to a method for synthesizing a compound of formula (I), preferably using solid phase synthesis.

According to an embodiment, the compound of formula (I) is a trifluoroacetic acid (TFA) salt, or an acetate salt.

The resin used in the present process can be any type of resin conventionally used in solid phase synthesis. These resins are well known to the person skilled in the art. Among resins, one can cite polystyrene resin, like microporous polystyrene resin or macroporous polystyrene resin, polyacrylamide resins, and copolymers resins. The linker L or L' is preferably an acid labile linker. The acid labile linker can be cleaved during step h) or h') when acid conditions are used. The linker L or L' varies depending on the resin used, and are well known to the person skilled in the art. Among resins comprising a linker group L or L', one can cite p-alkoxybenzyl alcohol resin (Wang resin), 4-(1',1'-dimethyl-1'-hydroxypropyl)phenoxyacetyl-alanyl-aminomethyl resin (DHPP resin), diphenyldiazomethane resin, (PDDM resin), trityl chloride resin and 2-chlorotrityl chloride resin.

Each of the protecting groups PG, PG1, PG5, PG6, PG7, PG', PG1', PG5', PG6', and PG7' can be independently selected from the group consisting of benzyl, p-methoxybenzyl (PMB), tertiary butyl (t-Bu), methoxymethyl (MOM), methoxyethoxymethyl (MEM), methylthiomethyl (MTM), tetrahydropyranyl (THP), tetrahydrofuranyl (THF), benzyloxymethyl (BOM), trimethylsilyl (TMS), triethylsilyl (TES), t-butyldimethylsilyl (TBDMS), and triphenylmethyl (trityl, Tr).

According to an embodiment, PG, PG1, PG5, PG6, and PG7 are tertiary butyl (t-Bu). According to an embodiment, PG', PG1', PG5', PG6', and PG7' are tertiary butyl (t-Bu).

Each of the protecting groups PG2, PG3, PG4, PG2', PG3' and PG4' can be independently selected from the group consisting of t-butyloxycarbonyl (Boc), 9-fluorenyl methoxycarbonyl (Fmoc), allyloxycarbonyl (alloc), N-(1-(4,4-dimethyl-2,6-dioxocyclohexylidene)ethyl) (Dde), monomethoxytrityl (MMt), 1-(1-Adamantyl)-1-Methylethoxycarbonyl (Adpoc), N-(1-(4,4-dimethyl-2,6-dioxocyclohex-1-ylidene)-3-methylbutyl) (ivDde) and 4-methyltrityl (Mtt), preferably from the group consisting of Dde, ivDde and Fmoc.

According to an embodiment, PG2, PG3 and PG4 are 9-fluorenyl methoxycarbonyl (Fmoc). According to an embodiment, PG2' is N-(1-(4,4-dimethyl-2,6-dioxocyclohex-1-ylidene)-3-methylbutyl) (ivDde) or Dde, and PG3' and PG4' are 9-fluorenyl methoxycarbonyl (Fmoc). Dde and ivDde are the preferred protecting groups for PG2'. In particular, the deprotection of these groups does not require the use of a metal catalyst, on the contrary to the Alloc protecting group, which is removed using $Pd(PPh_3)_4$. Moreover, these groups are less bulky than MMt and Mtt, so that the loading on the resin can be higher, and they are less sensitive to acidic conditions than Mtt.

Each of the groups R1, R2, R3, R1', R2' and R3' can be independently selected from the group consisting of H, succinimidyl, p-nitrophenyl, tetrafluorophenyl, 3,4-dihydro-4-oxo-1,2,3-benzotriazine-3-yl, pentafluorophenyl, and 2,4,5-trichlorophenyl, preferably from the group consisting of H and succinimidyl. According to an embodiment, R1, R2 and R3 are H. According to an embodiment, R1', R2' and R'3 are H.

LG and LG' are leaving groups that are independently selected from imidazole, halogens and activating ester groups. Among halogen, one can cite chloride. The fact that compounds (III) and (III') have a —NH—(CO)-LG or LG' moiety, and not a —N═C═O reactive moiety, makes it possible to synthesize the compound of formula (I) without the use of toxic compounds like phosgene or triphosgene, which are very hazardous products. LG or LG' is preferably an imidazole, as it can be synthesized without using of phosgene or triphosgene, which are very hazardous products. Moreover, when imidazole is used as a leaving group, the product is a stable solid, which can be easily handled.

According to a preferred embodiment, the method for synthesizing the compound of formula (I) comprises all the steps a)-h), or all of the steps a')-h').

Each of steps a)-h) or a')-h') can be performed at room temperature or under heating, for example at a temperature between 25 and 70° C. Each of steps a)-h) or a')-h') can be performed for a period of time between 5 minutes and 3 hours. Each of steps a)-h) or a')-h') can be performed under inert atmosphere, for example under argon.

In between each step, the resulting supported compound can be washed with a solvent, like dimethylformamide (DMF), dichloromethane (DCM), or isopropanol (IPA). It can also be alternately washed with different solvents, like alternating DMF and IPA washing.

Each of steps a)-h) or a')-h') can be performed using a polar aprotic solvent. According to an embodiment, the polar aprotic solvent that can be used in each of steps a) to h), or a') to h'), is selected from the group consisting of dimethylformamide (DMF), N-methyl-2-pyrrolidone (NMP), dichloromethane (DCM), a dichloromethane/dimethylformamide mixture, acetonitrile (ACN), an acetonitrile/dimethylformamide mixture, and dimethylsulfoxide (DMSO). Advantageously, the polar aprotic solvent that can be used in any of steps a) to h), or a') to h'), is dimethylformamide (DMF).

Each of step a), c), e), g), a'), c'), e') or g') can be performed using a coupling agent and/or a base. The base that can be used in each of step a), c), e), g), a'), c'), e') or g') can be independently selected from the group consisting of N,N-Diisopropylethylamine (DIPEA), N,N-Diisopropylethylamine ($^{i}$Pr2NEt), triethylamine (TEA), 4-methylmorpholine (NMM), imidazole, pyridine, and collidine, preferably the base is DIPEA. The coupling agent that can be used in any of step a), c), e), a'), c') or e') can be independently selected from the group consisting of benzotriazol-1-yl-oxytripyrrolidinophosphonium hexafluorophosphate (PyBOP), 1-[Bis(dimethylamino)methylene]-1H-1,2,3-triazolo[4,5-b]pyridinium 3-oxid hexafluorophosphate (HATU), 2-(1H-Benzotriazole-1-yl)-1,1,3,3-tetramethyluronium tetrafluoroborate (TBTU), 2-(1H-benzotriazol-1-yl)-1,1,3,3-tetramethyluronium hexafluorophosphate (HBTU), 2-chloro-4,6-dimethoxy-1,3,5-triazine (CDMT), N-[(5-Chloro-3-oxido-1H-benzotriazol-1-yl)-4-morpholinylmethylene]-N-methylmethanaminium hexafluorophosphate (HDMC), 1-Cyano-2-ethoxy-2-oxoethylidenaminooxy)dimethyl-amino-morpholino-carbenium hexafluorophosphate (COMU), dimethylamino(triazolo[4,5-b]pyridin-3-yloxy)methylidene]-dimethylazanium; tetrafluoroborate (TATU), N,N,N',N'-tetramethyl-S-(1-oxido-2-pyridyl)thiouronium tetrafluoroborate (TOTT), N-Ethoxycarbonyl-2-ethoxy-1,2-dihydroquinoline (EEDQ), 1-Propanephosphonic anhydride (T3P), and 4-(4,6-dimethoxy-1,3,5-triazin-2-yl)-4-methyl-morpholinium chloride (DMTMM), preferably from the group consisting of PyBOP and TBTU.

According to an embodiment, step a) is performed using a base, typically DIPEA. According to an embodiment, step a') is performed using a base, typically DIPEA. According to an embodiment, step c) is performed using a coupling agent and a base, typically TBTU and DIPEA. According to an embodiment, step c') is performed using a coupling agent and a base, typically TBTU and DIPEA. According to an embodiment, step e) is performed using a coupling agent and a base, typically TBTU and DIPEA. According to an embodiment, step e') is performed using a coupling agent and a base, typically TBTU and DIPEA. According to an embodiment, step g) is performed using a coupling agent and a base, typically PyBOP and DIPEA. According to an embodiment, step g') is performed using a coupling agent and a base, typically PyBOP and DIPEA.

The deprotecting agent used in any of step b), d), f), b'), d') or f) can be independently selected from the group consisting of hydrazine, piperidine, morpholine, 1,8-Diazabicyclo[5.4.0]undec-7-ene (DBU), diethylamine (DEA), dicyclohexamine, 4-methylpiperidine (4MP), Tris(2-aminoethyl)amine, pyridine and collidine, preferably from the group consisting of hydrazine and piperidine. According to an embodiment, the deprotecting agent used in step b) is piperidine. According to an embodiment, the deprotecting agent used in step b') is hydrazine. According to an embodiment, the deprotecting agent used in step d) is piperidine. According to an embodiment, the deprotecting agent used in step d') is piperidine. According to an embodiment, the deprotecting agent used in step f) is piperidine. According to an embodiment, the deprotecting agent used in step f) is piperidine.

The cleavage reagent of step h) or h') can be an acid, preferably trifluoroacetic acid (TFA) or a trifluoroacetic acid (TFA)/water/triisopropylsilane mixture.

According to an embodiment, the overall yield of the synthesis can be greater than or equal to 10%, based on the supported starting material, compound (II) or (II'), preferably greater than or equal to 15%, and more preferably, greater than or equal to 20%. The overall yield can be between 15 and 100%.

In some cases, the present method can also comprise a deprotection step to give compound (II), prior to step a).

In some cases, the present method can also comprise a deprotection step to give compound (II'), prior to step a').

EMBODIMENTS

The following specific embodiments are disclosed:

1. A method for synthesizing a compound of formula (I), or a pharmaceutically acceptable salt thereof, using solid phase synthesis:

(I)

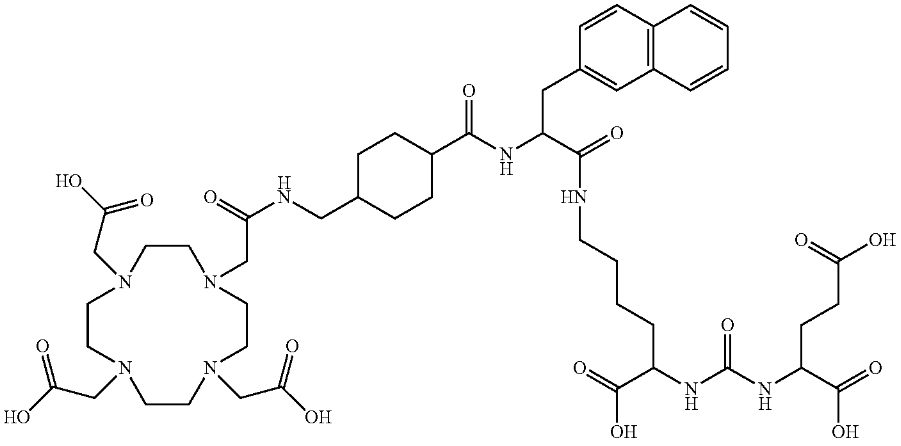

2. The method according to embodiment 1, wherein said method comprises at least one of the following steps:

a) contacting a supported, preferably a resin-based, compound of formula (II)

(II)

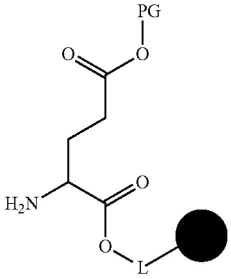

with a compound of formula (III)

(III)

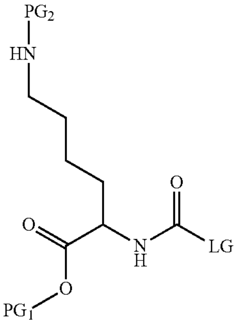

to provide a supported, preferably a resin-based, compound of formula (IV)

(IV)

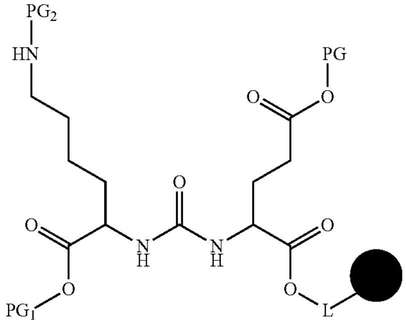

b) contacting the supported, preferably the resin-based, compound of formula (IV) with a deprotecting agent to provide a supported, preferably a resin-based, compound of formula (V)

(V)

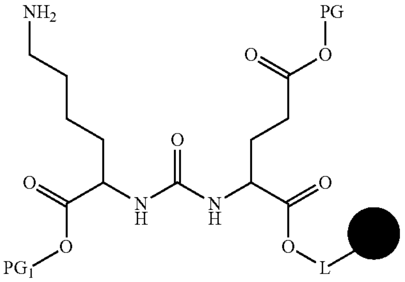

c) contacting the supported, preferably the resin-based, compound of formula (V) with a compound of formula (VI)

(VI)

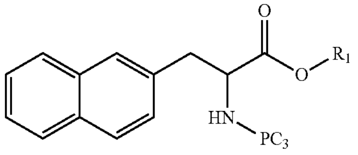

to provide a supported, preferably a resin-based, compound of formula (VII)

(VII)

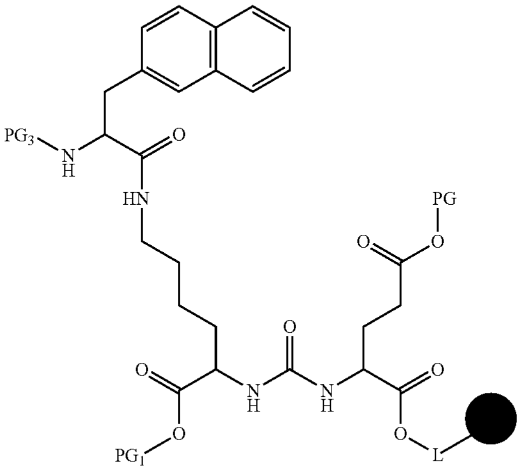

d) contacting the supported, preferably the resin-based compound of formula (VII) with a deprotecting agent to provide a supported, preferably a resin-based, compound of formula (VIII)

(VIII)

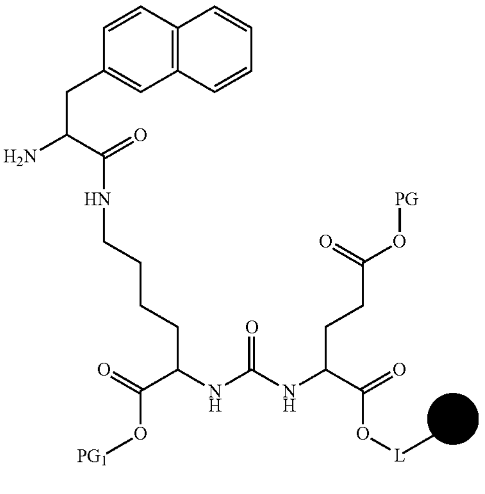

e) contacting the supported, preferably the resin-based, compound of formula (VIII) with a compound of formula (IX)

(IX)

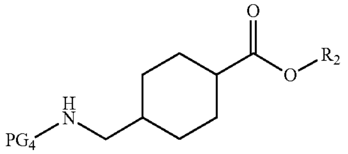

to provide a supported, preferably a resin-based, compound of formula (X)

(X)

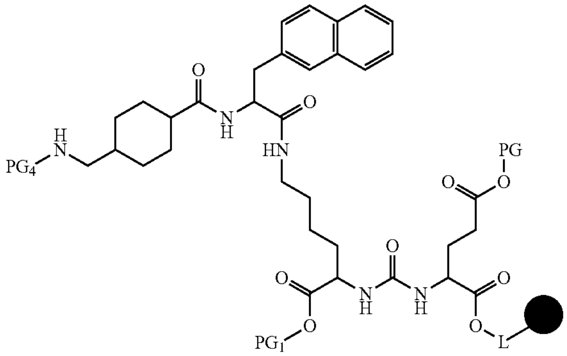

f) contacting the supported, preferably the resin-based compound of formula (X) with a deprotecting agent to provide a supported, preferably a resin-based, compound of formula (XI)

(XI)

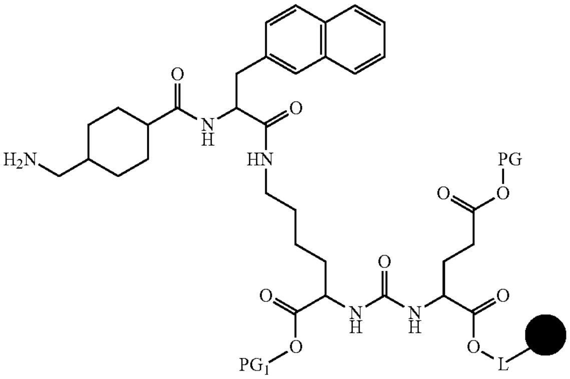

g) contacting the supported, preferably the resin-based, compound of formula (XI) with a compound (XII)

(XII)

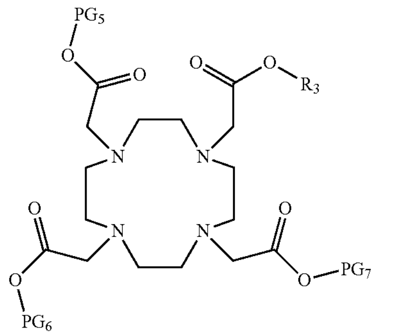

to provide a supported, preferably a resin-based, compound of formula (XIII)

(XIII)

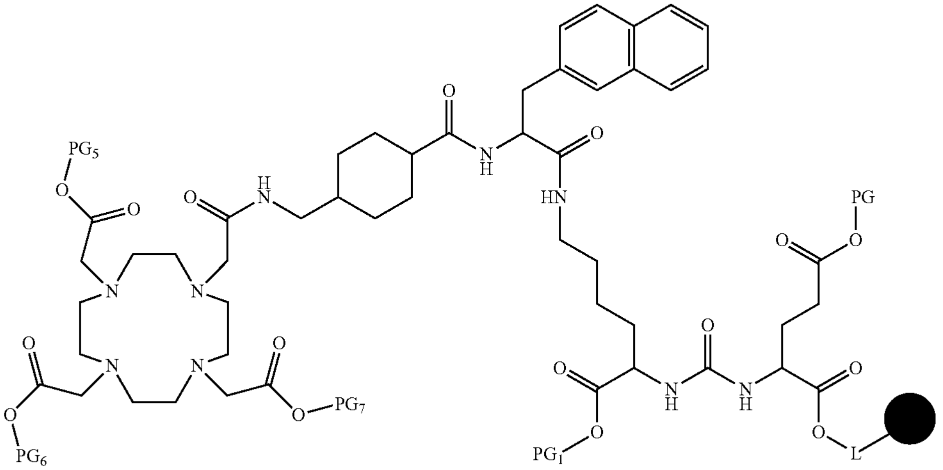

h) contacting the supported, preferably the resin-based, compound of formula (XIII) with a cleavage reagent, and optionally with a deprotecting agent, to provide the compound of formula (I), or a pharmaceutically acceptable salt thereof;

wherein

PG, PG1, PG5, PG6 and PG7 are each independently a carboxyl protecting group;

L is a linker:

PG2, PG3 and PG4 are each independently an amino protecting group;

R1, R2 and R3 are each independently H, or an activating ester group, and

LG is a leaving group selected from the group consisting of imidazole, halogens and activating ester groups.

3. The method according to embodiment 2, wherein said method comprises all the steps a)-h).
4. The method according to any of embodiments 2-3, wherein PG, PG1, PG5, PG6, and PG7, are independently selected from the group consisting of benzyl, p-methoxybenzyl (PMB), tertiary butyl (t-Bu), methoxymethyl (MOM), methoxyethoxymethyl (MEM), methylthiomethyl (MTM), tetrahydropyranyl (THP), tetrahydrofuranyl (THF), benzyloxymethyl (BOM), trimethylsilyl (TMS), triethylsilyl (TES), t-butyldimethylsilyl (TBDMS), and triphenylmethyl (trityl, Tr), preferably PG, PG1, PG5, PG6, and PG7 are tertiary butyl (t-Bu).
5. The method according to any of embodiments 2-4, wherein PG2, PG3 and PG4 are independently selected from the group consisting of t-butyloxycarbonyl (Boc), 9-fluorenyl methoxycarbonyl (Fmoc), allyloxycarbonyl (alloc), N-(1-(4,4-dimethyl-2,6-dioxocyclohexylidene)ethyl) (Dde), monomethoxytrityl (MMt), 1-(1-Adamantyl)-1-Methylethoxycarbonyl (Adpoc), N-(1-(4,4-dimethyl-2,6-dioxocyclohex-1-ylidene)-3-methylbutyl) (ivDde) and 4-methyltrityl (Mtt), preferably, PG2, PG3 and PG4 are 9-fluorenyl methoxycarbonyl (Fmoc).
6. The method according to any of embodiments 2-5, wherein R1, R2 and R3 are independently selected from the group consisting of H, succinimidyl, p-nitrophenyl, tetrafluorophenyl, 3,4-dihydro-4-oxo-1,2,3-benzotriazine-3-yl, pentafluorophenyl, and 2,4,5-trichlorophenyl, preferably R1, R2 and R3 are selected from the group consisting of H or succinimidyl.
7. The method according to any of embodiments 2-6 wherein at least one of the steps a)-h) is performed using a polar aprotic solvent.
8. The method according to embodiment 7, wherein the polar aprotic solvent is selected from the group consisting of dimethylformamide (DMF), N-methyl-2-pyrrolidone (NMP), dichloromethane (DCM), a dichloromethane/dimethylformamide mixture, acetonitrile (ACN), an acetonitrile/dimethylformamide mixture, and dimethylsulfoxide (DMSO), preferably, the solvent is dimethylformamide (DMF).
9. The method according to any of embodiments 2-8, wherein at least one of the step a), c), e) or g) is performed using a coupling agent and/or a base.
10. The method according to embodiment 9, wherein the base is selected from the group consisting of N,N-Diisopropylethylamine (DIPEA), N,N-Diisopropylethylamine ($^{i}$Pr2NEt), triethylamine (TEA), 4-methylmorpholine (NMM), imidazole, pyridine, and collidine.
11. The method according to embodiment 9 or 10, wherein the coupling agent is selected from the group consisting of benzotriazol-1-yl-oxytripyrrolidinophosphonium hexafluorophosphate (PyBOP), 1-[Bis(dimethylamino)methylene]-1H-1,2,3-triazolo[4,5-b]pyridinium 3-oxid hexafluorophosphate (HATU), 2-(1H-Benzotriazole-1-yl)-1,1,3,3-tetramethyluronium tetrafluoroborate (TBTU), 2-(1H-benzotriazol-1-yl)-1,1,3,3-tetramethyluronium hexafluorophosphate (HBTU), 2-chloro-4,6-dimethoxy-1,3,5-triazine (CDMT), N-[(5-Chloro-3-oxido-1H-benzotriazol-1-yl)-4-morpholinylmethylene]-N-methylmethanaminium hexafluorophosphate (HDMC), 1-Cyano-2-ethoxy-2-oxoethylidenaminooxy)dimethylamino-morpholino-carbenium hexafluorophosphate (COMU), dimethylamino(triazolo[4,5-b]pyridin-3-yloxy)methylidene]-dimethylazanium; tetrafluoroborate (TATU), N,N,N',N'-tetramethyl-S-(1-oxido-2-pyridyl)thiouronium tetrafluoroborate (TOTT), N-Ethoxycarbonyl-2-ethoxy-1,2-dihydroquinoline (EEDQ), 1-Propanephosphonic anhydride (T3P), and 4-(4,6-dimethoxy-1,3,5-triazin-2-yl)-4-methyl-morpholinium chloride (DMTMM).

12. The method according to any of embodiments 9-11, wherein step a) is performed using a base, typically DIPEA, step c) is performed using a coupling agent and a base, typically TBTU and DIPEA, step e) is performed using a coupling agent and a base, typically TBTU and DIPEA and step g) is performed using a coupling agent and a base, typically PyBOP and DIPEA.

13. The method according to any of embodiments 2-12, wherein the deprotecting agent that is used in step b), d) or f) is selected from the group consisting of hydrazine, piperidine, morpholine, 1,8-Diazabicyclo[5.4.0]undec-7-ene (DBU), diethylamine (DEA), dicyclohexamine, 4-methylpiperidine (4MP), Tris(2-aminoethyl)amine, pyridine and collidine, preferably from the group consisting of hydrazine and piperidine.

14. The method according to any of embodiments 2-13, wherein step h) is performed using an acid, preferably trifluoroacetic acid (TFA) or a trifluoroacetic acid (TFA)/water/triisopropylsilane mixture.

15. The method according to embodiment 1, wherein said method comprises at least one of the following steps:

a') contacting a supported, preferably a resin-based, compound of formula (II')

(II')

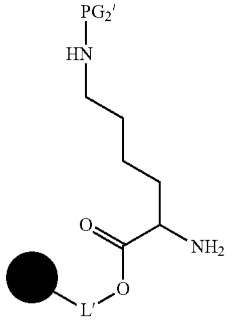

with a compound of formula (III')

(III')

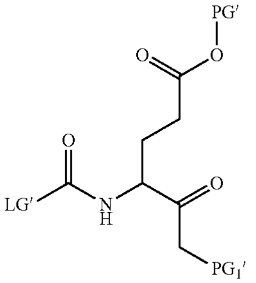

to provide a supported, preferably a resin-based, compound of formula (IV')

(IV')

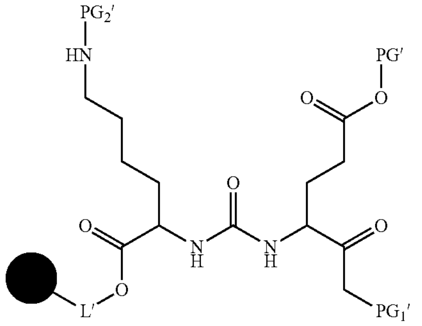

b') contacting the supported, preferably the resin-based, compound of formula (IV') with a deprotecting agent to provide a supported, preferably a resin-based, compound of formula (V')

(V')

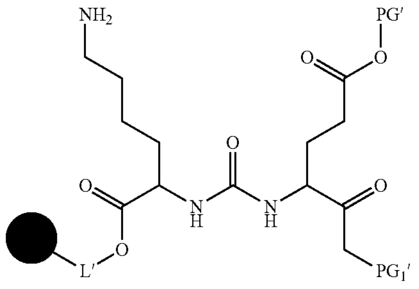

c') contacting the supported, preferably the resin-based, compound of formula (V') with a compound of formula (VI')

(VI')

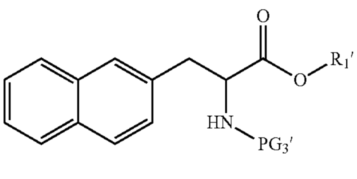

to provide a supported, preferably a resin-based, compound of formula (VII')

(VII')

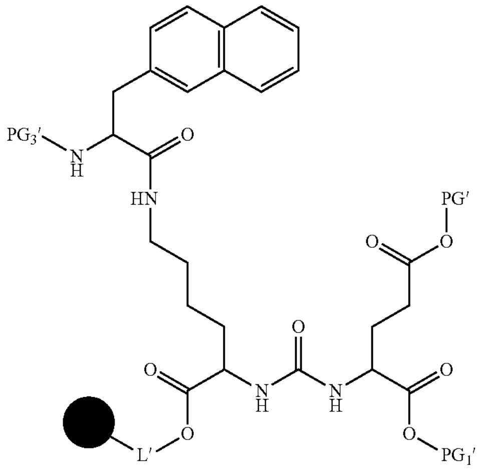

d') contacting the supported, preferably the resin-based, compound of formula (VII') with a deprotecting agent to provide a supported, preferably a resin-based, compound of formula (VIII')

(VIII')

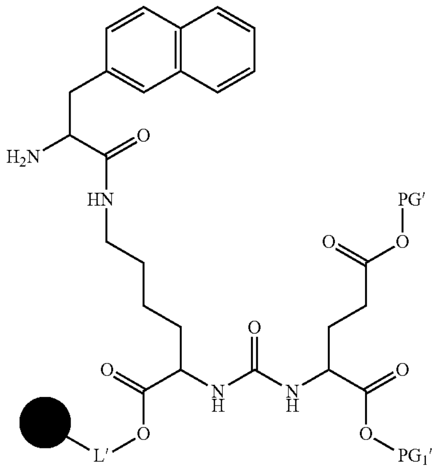

e') contacting the supported, preferably the resin-based, compound of formula (VIII') with a compound of formula (IX')

(IX')

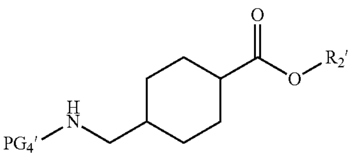

to provide a supported, preferably a resin-based, compound of formula (X')

(X')

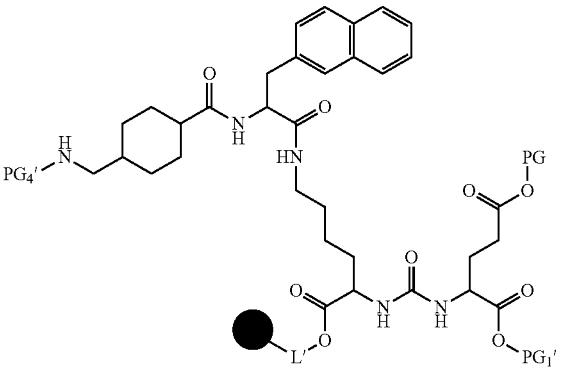

f') contacting the supported, preferably the resin-based, compound of formula (X') with a deprotecting agent to provide a supported, preferably a resin-based, compound of formula (XI')

(XI')

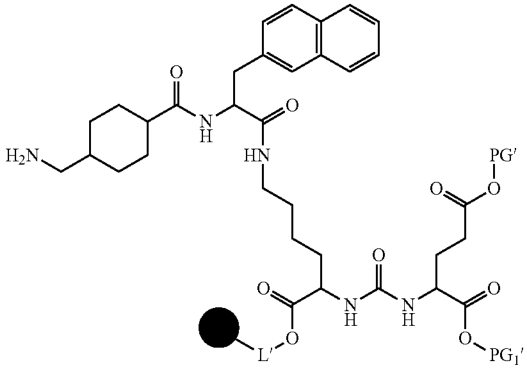

g') contacting the supported, preferably the resin-based, compound of formula (XI') with a compound (XII')

(XII')

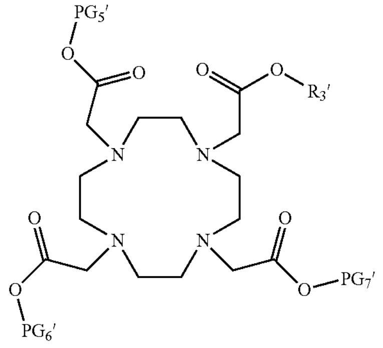

to provide a supported, preferably a resin-based, compound of formula (XIII')

(XIII')

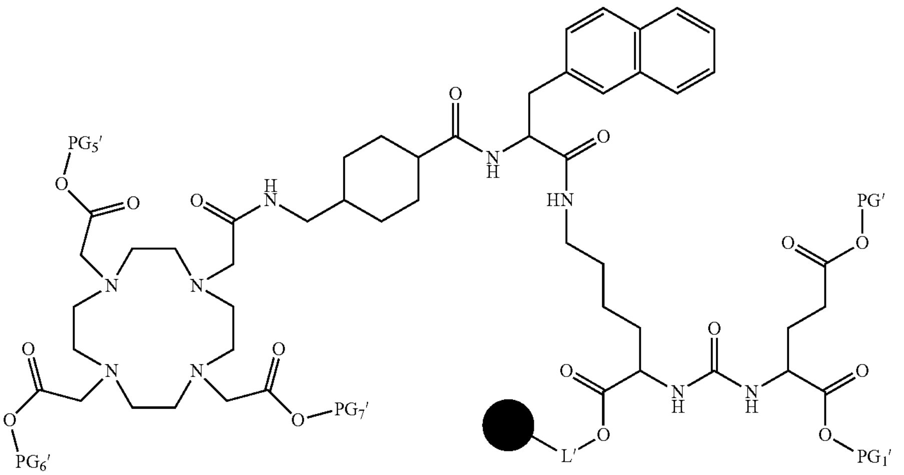

h') contacting the supported, preferably the resin-based, compound of formula (XIII') with a cleavage reagent, and optionally with a deprotecting agent, to provide the compound of formula (I), or a pharmaceutically acceptable salt thereof, wherein PG', PG1', PG5', PG6' and PG7' are each independently a carboxyl protecting group;

L' is a linker;

PG2', PG3' and PG4' are each independently an amino protecting group;

R1', R2' and R3' are each independently H or an activating ester group, and

LG' is a leaving group selected from the group consisting of imidazole, halogens and activating ester groups.

16. The method according to embodiment 15, wherein said method comprises all the steps a')-h').

17. The method according to any of embodiments 15-16, wherein PG', PG1', PG5', PG6', and PG7', are independently selected from the group consisting of benzyl, p-methoxybenzyl (PMB), tertiary butyl (t-Bu), methoxymethyl (MOM), methoxyethoxymethyl (MEM), methylthiomethyl (MTM), tetrahydropyranyl (THP), tetrahydrofuranyl (THF), benzyloxymethyl (BOM), trimethylsilyl (TMS), triethylsilyl (TES), t-butyldimethylsilyl (TBDMS), and triphenylmethyl (trityl, Tr), preferably PG', PG1', PG5', PG6', and PG7' are tertiary butyl (t-Bu).

18. The method according to any of embodiments 15-17, wherein PG2', PG3' and PG4' are independently selected from the group consisting of t-butyloxycarbonyl (Boc), 9-fluorenyl methoxycarbonyl (Fmoc), allyloxycarbonyl (alloc), N-(1-(4,4-dimethyl-2,6-dioxocyclohexylidene)ethyl) (Dde), monomethoxytrityl (MMt), 1-(1-Adamantyl)-1-Methylethoxycarbonyl (Adpoc), N-(1-(4,4-dimethyl-2,6-dioxocyclohex-1-ylidene)-3-methylbutyl) (ivDde) and 4-methyltrityl (Mtt), preferably, PG2' is N-(1-(4,4-dimethyl-2,6-dioxocyclohex-1-ylidene)-3-methylbutyl) (ivDde) or Dde, and PG3' and PG4' are 9-fluorenyl methoxycarbonyl (Fmoc).

19. The method according to any of embodiments 15-18, wherein R1', R2' and R3' are independently selected from the group consisting of H, succinimidyl, p-nitrophenyl, tetrafluorophenyl, 3,4-dihydro-4-oxo-1,2,3-benzotriazine-3-yl, pentafluorophenyl, and 2,4,5-trichlorophenyl, preferably R1', R2' and R3' are selected from the group consisting of H or succinimidyl.

20. The method according to any of embodiments 15-19 wherein at least one of the steps a')-h') is performed using a polar aprotic solvent.

21. The method according to embodiment 20, wherein the polar aprotic solvent is selected from the group consisting of dimethylformamide (DMF), N-methyl-2-pyrrolidone (NMP), dichloromethane (DCM), a dichloromethane/dimethylformamide mixture, acetonitrile (ACN), an acetonitrile/dimethylformamide mixture, and dimethylsulfoxide (DMSO), preferably, the solvent is dimethylformamide (DMF).

22. The method according to any of embodiments 15-21, wherein at least one of the step a'), c'), e') or g') is performed using a coupling agent and/or a base.

23. The method according to embodiment 22, wherein the base is selected from the group consisting of N,N-Diisopropylethylamine (DIPEA), N,N-Diisopropylethylamine (Pr2NEt), triethylamine (TEA), 4-methylmorpholine (NMM), imidazole, pyridine, and collidine.

24. The method according to embodiment 22 or 23, wherein the coupling agent is selected from the group consisting of benzotriazol-1-yl-oxytripyrrolidinophosphonium hexafluorophosphate (PyBOP), 1-[Bis(dimethylamino)methylene]-1H-1,2,3-triazolo[4,5-b]pyridinium 3-oxid hexafluorophosphate (HATU), 2-(1H-Benzotriazole-1-yl)-1,1,3,3-tetramethyluronium tetrafluoroborate (TBTU), 2-(1H-benzotriazol-1-yl)-1,1,3,3-tetramethyluronium hexafluorophosphate (HBTU), 2-chloro-4,6-dimethoxy-1,3,5-triazine (CDMT), N-[(5-Chloro-3-oxido-1H-benzotriazol-1-yl)-4-morpholinylmethylene]-N-methylmethanaminium hexafluorophosphate (HDMC), 1-Cyano-2-ethoxy-2-oxoethylidenaminooxy)dimethylamino-morpholino-carbenium hexafluorophosphate (COMU), dimethylamino(triazolo[4,5-b]pyridin-3-yloxy)methylidene]-dimethylazanium; tetrafluoroborate (TATU), N,N,N',N'-tetramethyl-S-(1-oxido-2-pyridyl)thiouronium tetrafluoroborate (TOTT), N-Ethoxycarbonyl-2-ethoxy-1,2-dihydroquinoline (EEDQ), 1-Propanephosphonic anhydride (T3P), and 4-(4,6-dimethoxy-1,3,5-triazin-2-yl)-4-methyl-morpholinium chloride (DMTMM).

25. The method according to any of embodiments 22-24, wherein step a') is performed using a base, typically DIPEA, step c') is performed using a coupling agent and a base, typically TBTU and DIPEA, step e') is performed using a coupling agent and a base, typically TBTU and DIPEA and step g') is performed using a coupling agent and a base, typically PyBOP and DIPEA.

26. The method according to any of embodiments 15-25, wherein the deprotecting agent that is used in step b'), d') or f) is selected from the group consisting of hydrazine, piperidine, morpholine, 1,8-Diazabicyclo [5.4.0]undec-7-ene (DBU), diethylamine (DEA), dicyclohexamine, 4-methylpiperidine (4MP), Tris(2-aminoethyl)amine, pyridine and collidine, preferably from the group consisting of hydrazine and piperidine.

27. The method according to any of embodiments 15-26, wherein step h') is performed using an acid, preferably trifluoroacetic acid (TFA) or a trifluoroacetic acid (TFA)/water/triisopropylsilane mixture.

The present disclosure further relates to the any one of the compounds as defined herein by the formulas from (II) to (XIII) or from (II') to (XIII'), or their use as intermediate in the method for synthesizing a compound of formula (I), or a pharmaceutically acceptable salt thereof. For example, in one embodiment, the present disclosure relates to the compound as defined herein by formula (II) or a pharmaceutically acceptable salt thereof. In another embodiment, the present disclosure relates to the use of the compound as defined herein by formula (II), or a pharmaceutically acceptable salt thereof, as intermediate in the method for synthesizing a compound of formula (I), or a pharmaceutically acceptable salt thereof. In the same way, further embodiments of the present disclosure as defined with respect to compounds as defined by the formula (III), (IV), (V), (VI), (VII), (VIII), (IX), (X), (XI), (XII), (XIII), (II'), (III'), (IV'), (V'), (VI'), (VII'), (VIII'), (IX'), (X'), (XI'), (XII'), or (XIII'). In another embodiment, the present disclosure relates to the use of two or more of the compounds as defined herein by any one of the formulas from (II) to (XIII) or from (II') to (XIII'), or a pharmaceutically acceptable salts thereof, as intermediates in the method for synthesizing a compound of formula (I), or a pharmaceutically acceptable salt thereof.

EXAMPLES

All chemicals and solvents were obtained from commercial suppliers and used without purification Fmoc-L-Lys (ivDde)-Wang PS-Resin was purchased from Rapp Polymere, DE. 1,1'-Carbonyldiimidazole was purchased from SAF, DE. Fmoc-3-(2-naphthyl)-L-alanine (Fmoc-Nal-OH) was purchased from Iris Biotech, DE. Fmoc-trans-4-aminomethyl)cyclohexanecarboxylic acid (FMOC-AM-CHC) was purchased from Iris Biotech, DE. H-Glu(OtBu)-OtBu×HCl was purchased from Bachem, CH. 3-(3-(((2-(tert-butoxy)-2-oxoethyl)(2-((2-(tert-butoxy)-2-oxoethyl)(5-(3-(tert-butoxy)-3-oxopropyl)-2-hydroxybenzyl)amino)ethyl)amino)methyl)-4-hydroxyphenyl)propanoic acid (DOTA(tBu)3) was purchased from Macrocyclics, US or Chematech FR. Fmoc-L-Glu(otbu)-Wang PS-Resin was purchased from Rapp Polymere, DE. H-Lys(Fmoc)-OtBu·HCl was purchased from CHI Scientific, Inc., USA NMR experiments were performed on a Bruker Avance Neo 500 MHZ.

The synthesis of PSMA-617 (TFA salt) was performed by solid phase peptide synthesis technique (SPPS) by use of a semi-automatic batch synthesizer via 2 different synthesis routes.

Example 1

Synthesis of PSMA-617 (TFA salt); (((S)-1-carboxy-5-((S)-3-(naphthalen-2-yl)-2-((1r,4S)-4-((2-(4,7,10-tris(carboxymethyl)-1,4,7,10-tetraazacyclododecan-1-yl)acetamido)methyl)cyclohexane-1-carboxamido)propanamido)pentyl)carbamoyl)-L-glutamic acid, trifluoroacetate salt, compound [7]

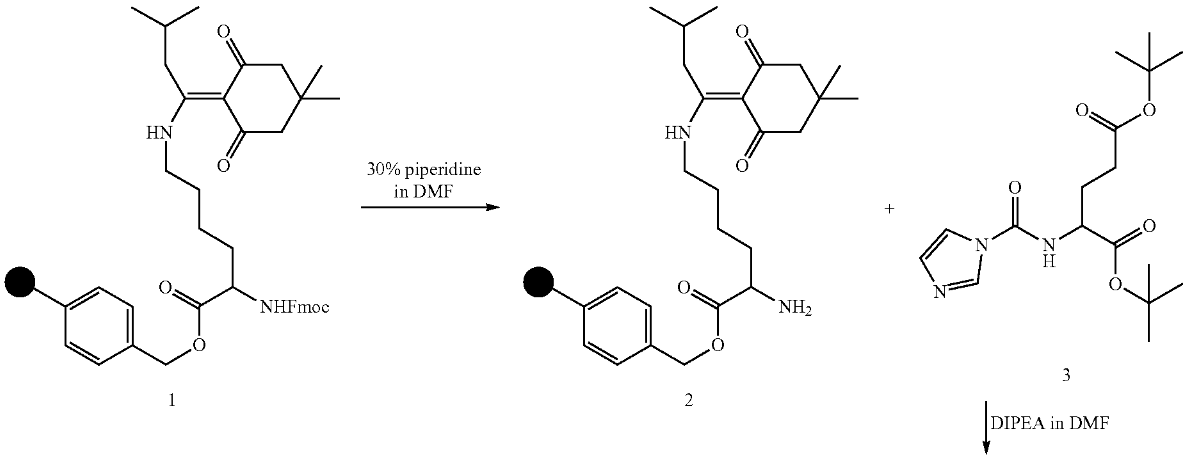

1 2 3

-continued
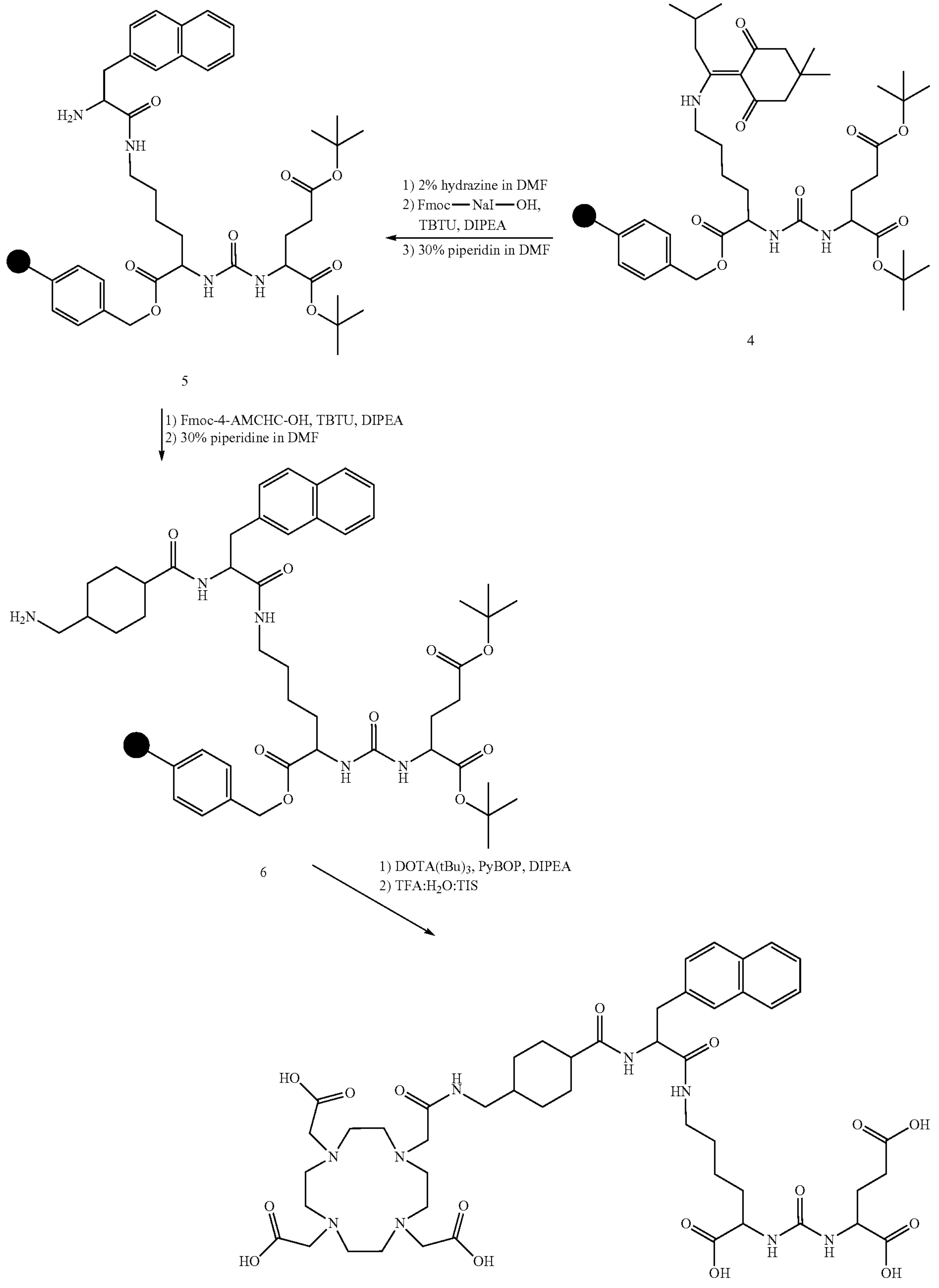
7

Synthesis of di-tert-butyl N-(1H-imidazole-1-carbonyl)glutamate Building block [3]

1,1'-Carbonyldiimidazole (CDI) (430 mg; 1.1 eq.) is transferred into a 250 ml round flask and dissolved in dichloromethane (50 ml). The solution is chilled to 0° C. and DIPEA (3.26 ml; 5 eq.) is added under stirring. H-Glu (OtBu)-OtBu×HCl (714 mg; 1 eq.) is dissolved in DCM (20 ml), cooled to 0° C. and added slowly to the stirred imidazole solution. The ice bath is removed and the reaction mixture is stirred at room temperature for 2-3 h. The progress of the reaction is monitored by in-process control (RP-HPLC; Nucleosil-100 RP-C18, 150×4 mm, 5 μm, gradient 10 min to 90 min in 15 min. Eluent H20/ACN 0.1% TFA).

After full conversion has been checked, the solution is reduced on a rotary evaporator. The residue is dissolved again in DCM, washed with 1 M $NaHCO_3$ and water. The organic layer is first concentrated in vacuo on a rotary evaporator and then dried on a freeze-dryer. Purity and identity of the building block are checked by RP-HPLC Nucleosil-100 RP-C18, 150×4 mm, 5 μm, gradient 10 min to 90 min in 30 min. Eluent H20/ACN 0.1% TFA (14.4 min. with 97% purity @215 nm) and Maldi TOF-MS ([M+H]+ 354.2±1.0) Matrix DHB. This obtained solid was used directly in the next step.

Assembly of PSMA-617 by SPPS-Approach:

Synthesis of Compound [2]

1 g of Fmoc-L-Lys(ivDde)-Wang PS-Resin ([1], 0.69 mmol/g; 0.69 mmol) is loaded into the reaction vessel and after swelling of the resin with 10 ml DMF the FMOC group is cleaved from the resin by use of 30% Piperidine in DMF 3×10 ml. After removal of the cleavage mixture by filtration, the resin is washed 3 times alternately with DMF and i-propanol to remove the piperidine solution. FMOC removal is checked by a Ninhydrin assay as in-process control. (Lit. Weng C. Chan, Peter D. White; Fmoc Solid Phase Peptide Synthesis. A Practical Approach. Oxford University Press, Oxford/New York 2000).

Note: If not otherwise mentioned, all elongation and FMOC-deprotection steps are checked as in-process control by Ninhydrin assay.

Synthesis of compound [4] Glu(otbu)-otBu-ureido-Lys(ivDde)-PS-resin

The freshly prepared building block, Di-tert-butyl N-(1H-imidazole-1-carbonyl)-glutamate (855 mg, 3.5 eq.) [3] is dissolved in 5 ml DMF, mixed with DIPEA (3.5 eq.) and added to the resin. The slurry is stirred for 1 h at RT. Excess Di-tert-butyl N-(1H-imidazole-1-carbonyl)-glutamate and reagents are removed by filtration followed by multiple washing steps with DMF and isopropanol (10 ml each 3 times). Completeness of the ureido-formation is checked again by Ninhydrin-assay.

Synthesis of Compound [5]

iv-Dde of the L-lysine side chain is removed by treating the resin with 2% hydrazine monohydrate in DMF (3×8 ml) and multiple DMF and isopropanol (10 ml each) washing steps.

Fmoc-3-(2-naphthyl)-L-alanine (Fmoc-Nal-OH) (905 mg, 3 eq.) is activated by in situ active ester formation using O-benzotriazol-1-yl-N,N,N',N'-tetramethyluronium tetrafluoro-borate (TBTU) 3 eq. mixed with DIPEA 3 eq. in 5 ml DMF and added to the resin for 1 hour at RT for the elongation step at the ε-amino group of the lysine. As the conversion is uncomplete as demonstrated by in-process control, a double coupling is performed followed by FMOC-cleavage.

Synthesis of Compound [6]

Fmoc-4-AMCHC-OH (785 mg, 3 eq.) is activated by in situ active ester formation using (TBTU) 3 eq. mixed with DIPEA 3 eq. in 5 ml DMF and added to the resin for 1 hour at RT, followed by FMOC-cleavage, resulting the resin bound Glu(otbu)-otBu-ureido-Lys(NH2-AMCHC-2-Nal-)-PS-resin.

Synthesis of Compound [7]

2-(4,7,10-tris(2-(tert-butoxy)-2-oxoethyl)-1,4,7,10-tetraazacyclododecan-1-yl)acetic acid (DOTA(tBu)3) (987 mg, 2.5 eq.) is coupled to the resin attached peptide by use of (1H-benzotriazol-1-yloxy)tripyrrolidino-phosphonium hexafluorophosphate (PyBOP) (2.5 eq.), DIPEA (5 eq.) dissolved in 5 ml DMF. The DOTA attachment is confirmed by performing a test cleavage on a small portion of resin bound peptide and the cleaved peptide sample is analyzed by HPLC and Maldi-TOF MS.

Finally, the resin is transferred to a sintered glass funnel and the resin bound peptide is washed extensively with DMF, ethanol and diethyl ether and dried.

The peptide is cleaved from the solid support by incubation with 10 ml cleavage cocktail, TFA:$H_2O$:TIS (94:3:3) for 4 hours at RT. After removal of the resin by filtration the cleavage solution containing the product is chilled and the product is precipitated by adding the peptide solution into ice-cooled diethyl ether. The product is isolated by centrifugation; the precipitate is washed with diethyl ether, dried and finally dissolved in a mixture of 10% acetonitrile in water and freeze-dried to obtain 670 mg crude product as a lyophilisate. The purity (42%) of the crude product was determined by HPLC and Maldi-TOF.

The purification of the product is done using preparative RP-HPLC method (RP-18, 10 μm) with water/acetonitrile (0.1% TFA) as eluent. The product first was pre-purified using an isocratic gradient of 25% acetonitrile, followed by a final purification using a gradient systems (20% acetonitrile to 70% acetonitrile @225 nm). All fractions that meet specifications for RP-HPLC-purity (≥98.0% were pooled and freeze-dried. Overall yield was 176 mg lyophilisate; 25% theor. based on resin loading.

Analysis of the synthesized molecules was performed using Nucleosil-100 RP-18, 150×4 mm, 5 μm; 1 mL/min @UV 215 nm; solvent A: H2O (0.1% TFA) B: CH3CN (0.1% TFA) with a linear gradient (10% B to 90% B in 30 min).

Mass spectrometry MALDI-MS (Kratos Axima) Calcd. for C49H71N9O16 1041.5 amu. Found [M+H+]: 1042.7 m/z.

The peptide content of the lyophilisate was determined by elemental analysis using the N value only (theory: C, 56.47; H, 6.87; N, 12.10; O, 24.56 (11.6% found) for calculating a net content of 96% (w/w).

Proposed structure was also confirmed by 2D-DQ-COSY, 2D-TOCSY, 2D-ROESY and 13C-HSQC NMR experiments on a Bruker Avance Neo 500 MHZ.

FIG. 1 is the 1D 1H spectrum with Watergate H2=suppression, serving for reference and as fingerprint.

Example 2
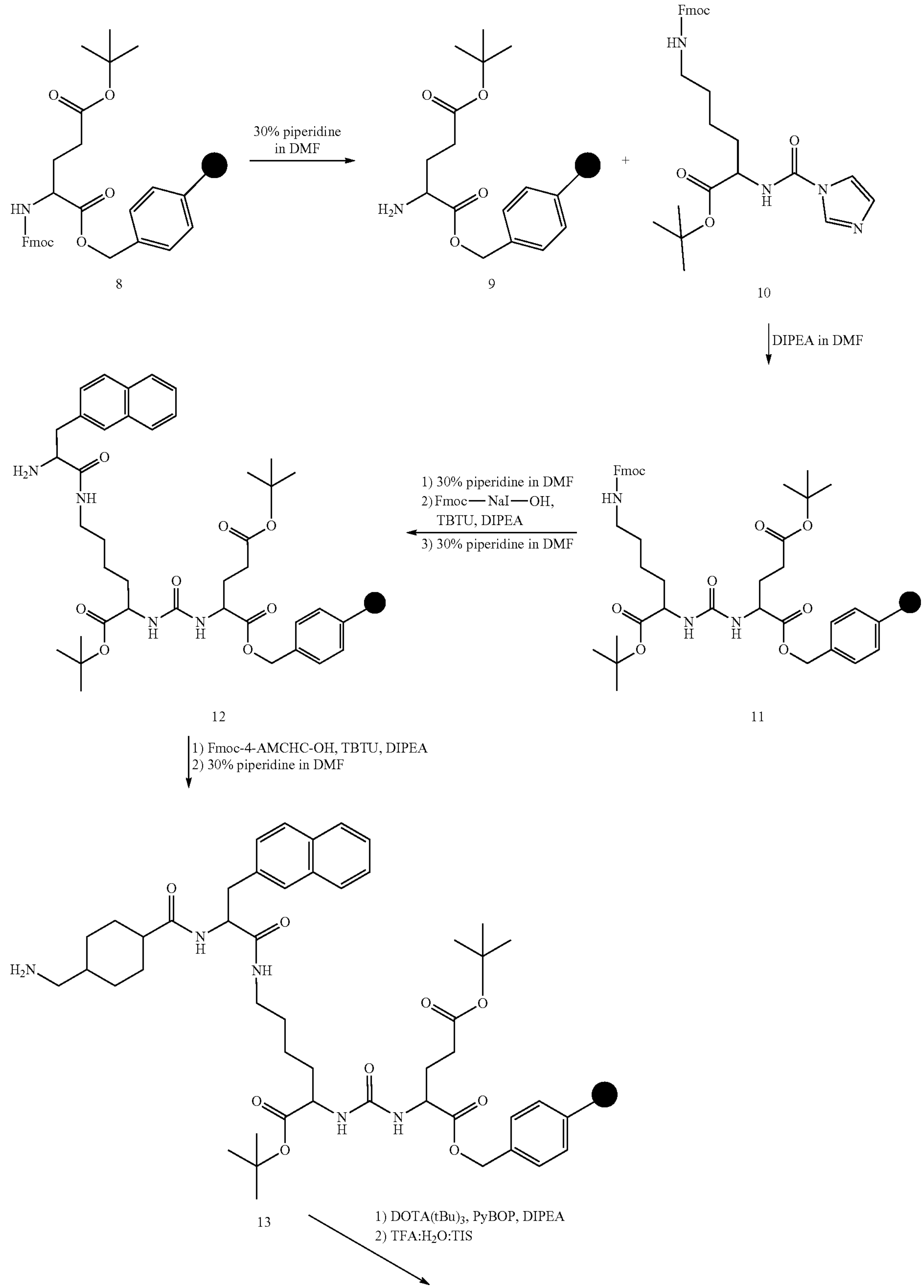

-continued

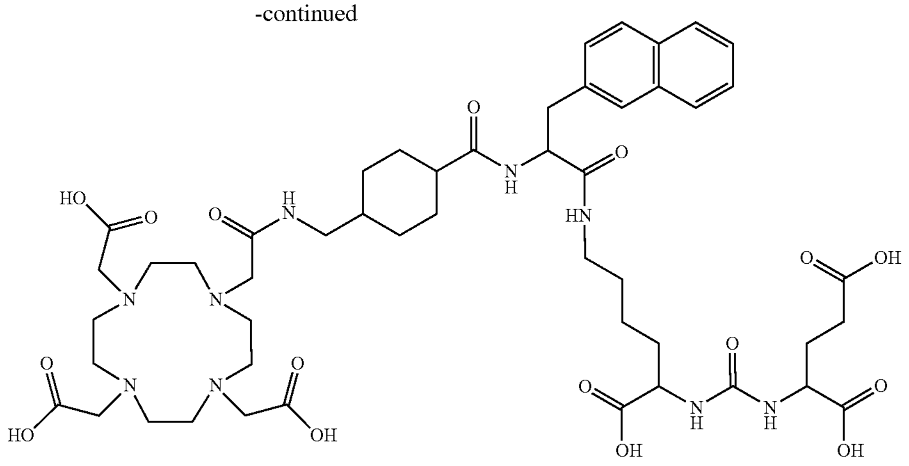

7

Synthesis of PSMA-617 (TFA salt); (((S)-1-carboxy-5-((S)-3-(naphthalen-2-yl)-2-((1r,4S)-4-((2-(4,7,10-tris(carboxymethyl)-1,4,7,10-tetraazacyclododecan-1-yl)acetamido)methyl)cyclohexane-1-carboxamido)propanamido)pentyl)carbamoyl)-L-glutamic acid, trifluoroacetate salt, [7]

Synthesis of tert-butyl N6-(((9H-fluoren-9-yl) methoxy)carbonyl)-N2-(1H-imidazole-1-carbonyl) lysinate (building block [10]

1,1'-Carbonyldiimidazole (CDI) (481 mg; 4.29 mmol; 1.1 eq.) is transferred into a 250 ml round flask and dissolved in dichloromethane (50 ml). The solution is chilled to 0° C. and DIPEA (5 eq.) is added under stirring.

H-Lys(FMOC)-OtBuxHCl (1.24 g; 1 eq.) is dissolved in DCM (40 ml), cooled to 0° C. and added slowly to the stirred imidazole solution. The ice bath is removed and the reaction mixture is stirred at room temperature for 3 hours. The progress of the reaction is monitored by in-process control (RP-HPLC; Nucleosil-100 RP-C18, 150×4 mm, 5 μm, gradient 10 min to 90 min in 15 min. Eluent H20/ACN 0.1% TFA). After conversion is completed, the solution is reduced on a rotary evaporator. The residue is dissolved in DCM, washed with 1 M $NaHCO_3$ and water. The organic layer is first concentrated in vacuo on a rotary evaporator and then dried on a freeze-dryer. The white solid is then used directly for the assembly of the ureido compound. Purity and identity of the building block are checked by RP-HPLC and MS. Nucleosil-100 RP-C18, 150×4 mm, 5 μm, gradient 10 min to 90 min in 30 min. Eluent: H20/ACN 0.1% TFA; Maldi TOF-MS ([M+H]+ 354.3±1.0) Matrix DHB.

Assembly of PSMA-617 by FMOC-SPPS-Strategy:

Synthesis of Compound [9]

1.5 g of Fmoc Glu(t-Bu) Wang resin (0.60 mmol/g) [8] is transferred into the reaction vessel and is swelled with 15 ml DMF, the FMOC group is cleaved by use of 30% Piperidine in DMF (3×15 ml). After alternate DMF/i-propanol washing steps to remove the piperidine solution, the removal of the FMOC group is checked by a Ninhydrin assay used as in-process control. (Lit. Weng C. Chan, Peter D. White; Fmoc Solid Phase Peptide Synthesis. A Practical Approach. Oxford University Press, Oxford/New York 2000).

Synthesis of Compound [11]

The freshly prepared N6-(((9H-fluoren-9-yl)methoxy) carbonyl)-N2-(1H-imidazole-1-carbonyl) lysinate (1.4 g, 3 eq.) [10] is dissolved in 10 ml DMF, mixed with DIPEA (3.5 eq.) and added to the resin. The slurry is stirred for 1 h at RT. Excess reagents are removed by filtration, followed by multiple washing steps with DMF and isopropanol (15 ml each time). Completeness of the reaction is checked by Ninhydrin-assay.

Synthesis of Compound [12]

Lys-otbu-ureido-Glu(otbu)-PS-resin [11]; FMOC group of the L-Lys side is cleaved using 30% Piperidine in DMF and after consecutive washing steps DMF/i-propanol/DMF (3×10 ml each).

Fmoc-2-Nal-OH (1.60 g, 4 eq.) is activated by in situ active ester formation using 0-benzotriazol-1-yl-N,N,N',N'-tetramethyluronium tetrafluoro-borate (TBTUxBF4$^-$) 3 eq. mixed with DIPEA 3 eq. dissolved in 10 ml DMF and added to the resin for 1.5 hour at RT for the elongation step at the s-amino group of the Lysine followed by FMOC-cleavage and consecutive washing steps.

Synthesis of Compound [13]

Fmoc-4-trans-AMCHC-OH (1.025 mg, 3 eq.) is activated by in situ active ester formation using TBTU 3 eq. mixed with DIPEA 3 eq. in 10 ml DMF and added to the resin for 1 hour at RT for the next elongation step at the ε-amino group of the lysine followed by FMOC-cleavage, resulting the resin bound Lys(NH2-trans-4-AMCHC-2-Nal-)ureido-Glu(otbu)PS-resin [13].

Synthesis of Compound [7]

(DOTA(tBu)3) (1.3 g, 2.5 eq.) is coupled to the resin attached peptide by use of PyBOP (2.5 eq.), DIPEA (5 eq.) dissolved in 10 ml DMF. Finally, the resin is transferred to a sintered glass funnel and the resin bound peptide is washed extensively with DMF, ethanol and diethyl ether and dried.

The peptide is cleaved from the solid support by incubation with 20 ml cleavage cocktail, TFA:$H_2O$:TIS (94:3:3) for 3 hours at RT. The resin is removed by filtration through a sintered glass funnel and washed thoroughly with small portions of TFA. The pooled cleavage solution is chilled and the product is precipitated by dropping the peptide solution slowly into ice-cooled diethyl ether. The product is isolated by centrifugation; the precipitate is washed with diethyl ether, dried, dissolved in a mixture of water and acetonitrile and freeze-dried.

The purification and isolation of the product is done according to example 1.

Overall yield including SPPS and purification was 22% based on resin loading.

The purity was checked by HPLC and Maldi-TOF MS. HPLC spiking experiments confirms identity with the product derived from example 1.

The invention claimed is:

1. A method for synthesizing a compound of formula (I), or a pharmaceutically acceptable salt thereof, using solid phase synthesis:

(I)

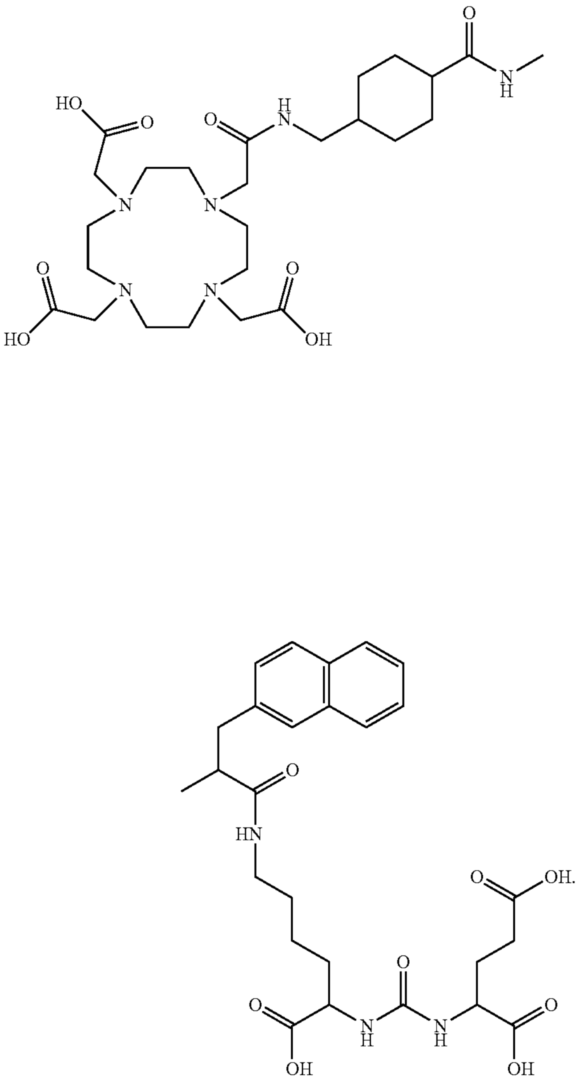

wherein said method comprises at least one of the following steps:

a) contacting a supported compound of formula (II)

(II)

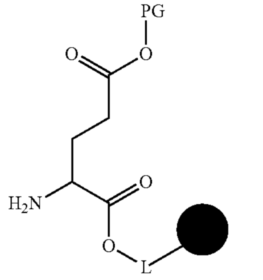

with a compound of formula (III)

(III)

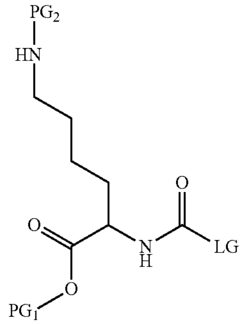

to provide a supported compound of formula (IV)

(IV)

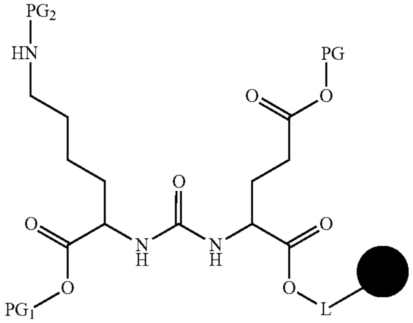

b) contacting the supported compound of formula (IV) with a deprotecting agent to provide a supported compound of formula (V)

(V)

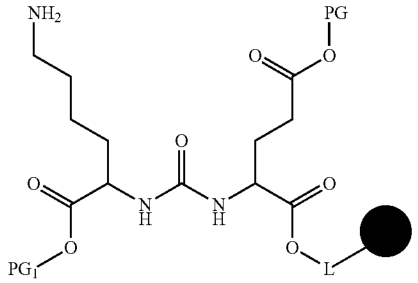

c) contacting the supported compound of formula (V) with a compound of formula (VI)

(VI)

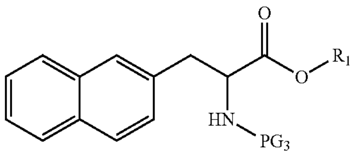

to provide a supported compound of formula (VII)

(VII)

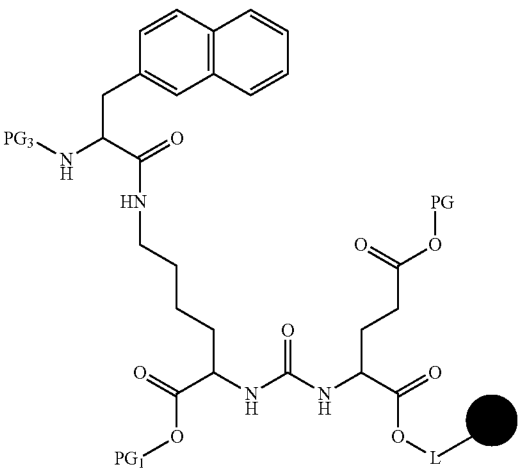

d) contacting the supported compound of formula (VII) with a deprotecting agent to provide a supported compound of formula (VIII)

(VIII)

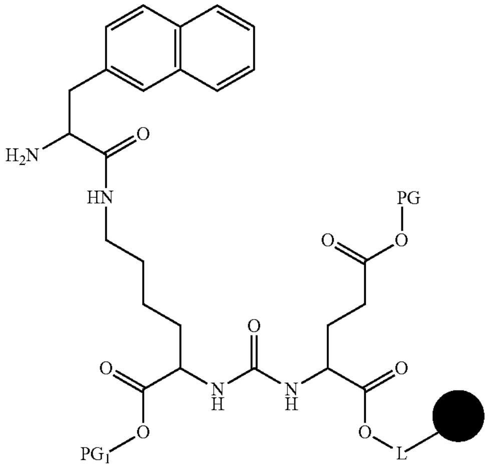

e) contacting the supported compound of formula (VIII) with a compound of formula (IX)

(IX)

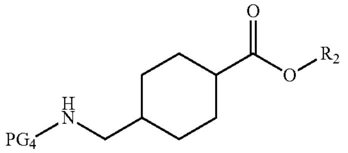

to provide a supported compound of formula (X)

(X)

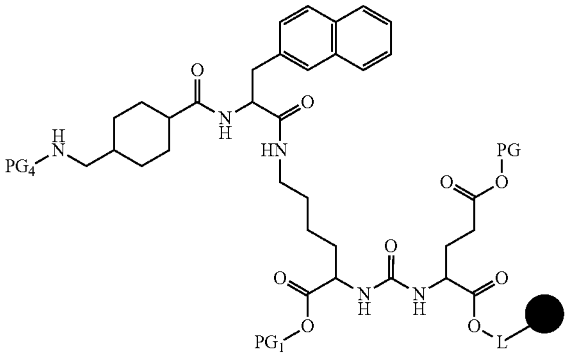

f) contacting the supported compound of formula (X) with a deprotecting agent to provide a supported compound of formula (XI)

(XI)

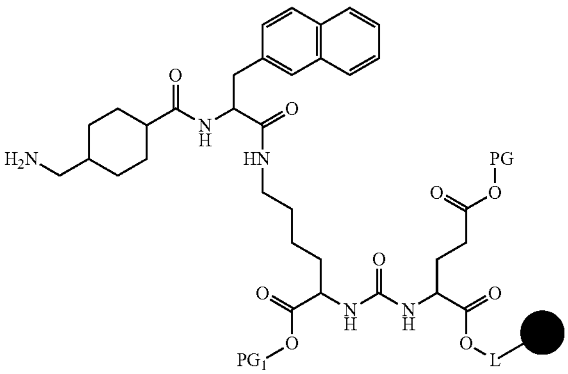

g) contacting the supported compound of formula (XI) with a compound (XII)

(XII)

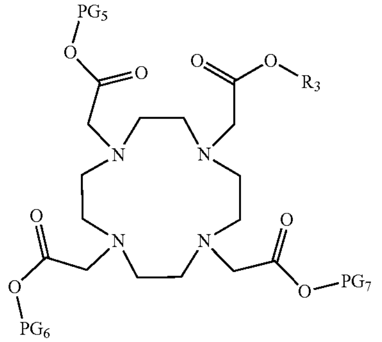

to provide a supported compound of formula (XIII)

(XIII)

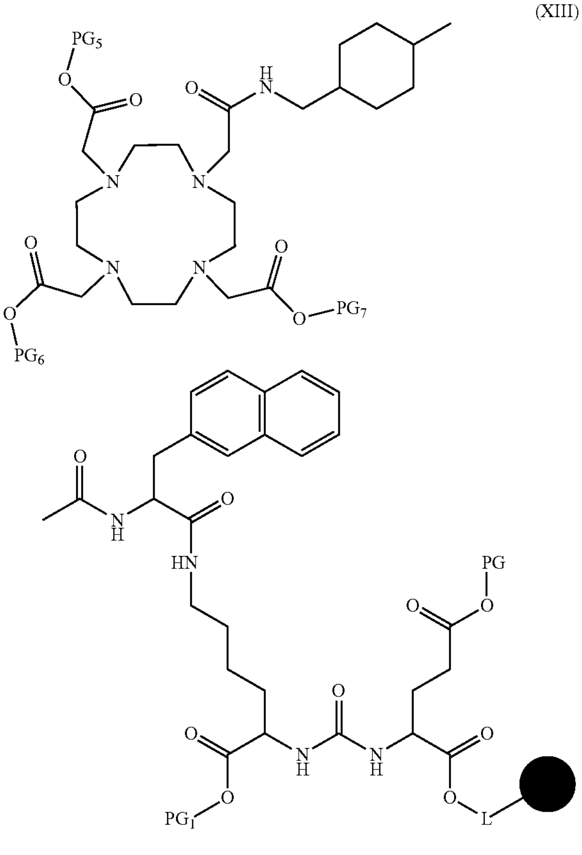

h) contacting the support compound of formula (XIII) with a cleavage reagent, and optionally with a deprotecting agent, to provide the compound of formula (I), or a pharmaceutically acceptable salt thereof;

wherein

PG, PG1, PG5, PG6 and PG7 are each independently a carboxyl protecting group;

L is a linker;

PG2, PG3 and PG4 are each independently an amino protecting group;

R1, R2 and R3 are each independently H, or an activating ester group, and

LG is a leaving group selected from the group consisting of imidazole, halogens and activating ester groups.

2. The method according to claim 1, wherein said method comprises all the steps a)-h).

3. The method according to claim 1, wherein PG, PG1, PG5, PG6, and PG7, are independently selected from the group consisting of benzyl, p-methoxybenzyl (PMB), tertiary butyl (t-Bu), methoxymethyl (MOM), methoxyethoxymethyl (MEM), methylthiomethyl (MTM), tetrahydropyranyl (THP), tetrahydrofuranyl (THF), benzyloxymethyl (BOM), trimethylsilyl (TMS), triethylsilyl (TES), t-butyldimethylsilyl (TBDMS), and triphenylmethyl (trityl, Tr).

4. The method according to claim 1, wherein PG2, PG3 and PG4 are independently selected from the group consisting of t-butyloxycarbonyl (Boc), 9-fluorenyl methoxycarbonyl (Fmoc), allyloxycarbonyl (alloc), N-(1-(4,4-dimethyl-2,6-dioxocyclohexylidene)ethyl) (Dde), monomethoxytrityl (MMt), 1-(1-Adamantyl)-1-Methylethoxycarbonyl (Adpoc), N-(1-(4,4-dimethyl-2,6-dioxocyclohex-1-ylidene)-3-methylbutyl) (ivDde), and 4-methyltrityl (Mtt).

5. The method according to claim 1, wherein at least one of the steps a)-h) is performed using a polar aprotic solvent.

6. The method according to claim 1, wherein at least one of the step a), c), e) or g) is performed using a coupling agent and/or a base.

7. A method for synthesizing a compound of formula (I), or a pharmaceutically acceptable salt thereof, using solid phase synthesis:

(I)

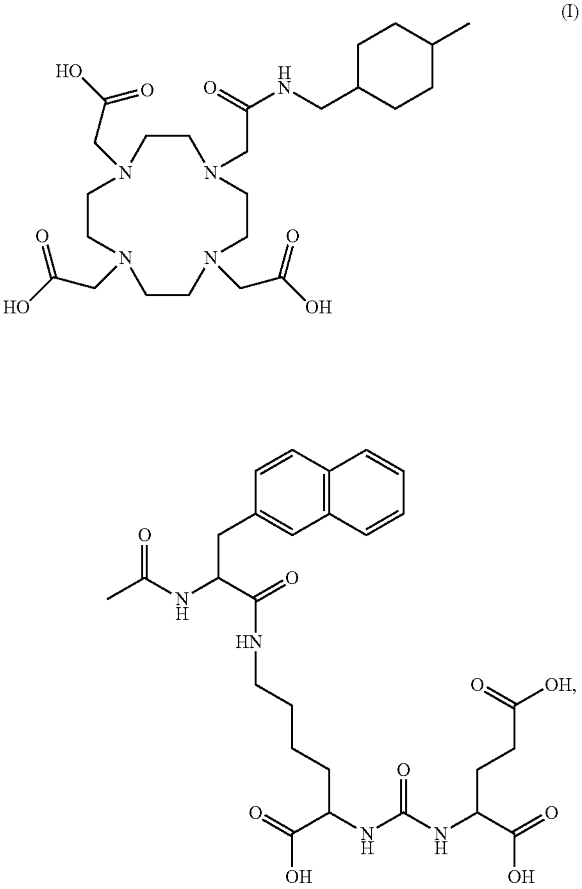

wherein said method comprises at least one of the following steps:

a') contacting a supported compound of formula (II')

(II')

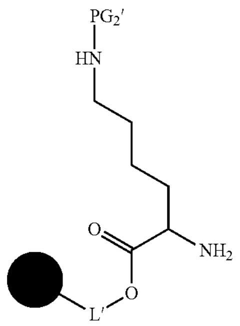

with a compound of formula (III')

(III')

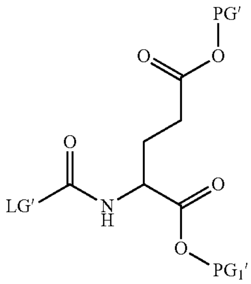

to provide a supported, compound of formula (IV')

(IV')

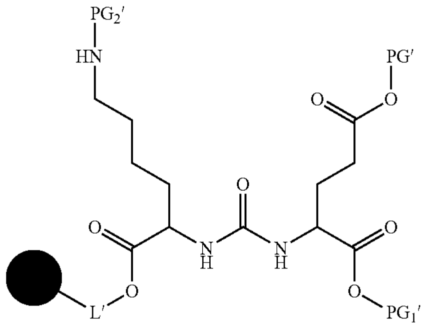

b') contacting the supported compound of formula (IV') with a deprotecting agent to provide a supported, compound of formula (V')

(V')

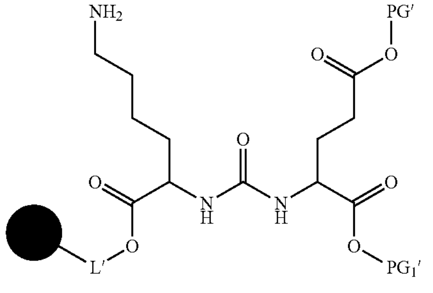

c') contacting the supported, compound of formula (V') with a compound of formula (VI')

(VI')

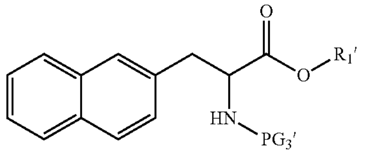

to provide a supported, compound of formula (VII')

(VII')

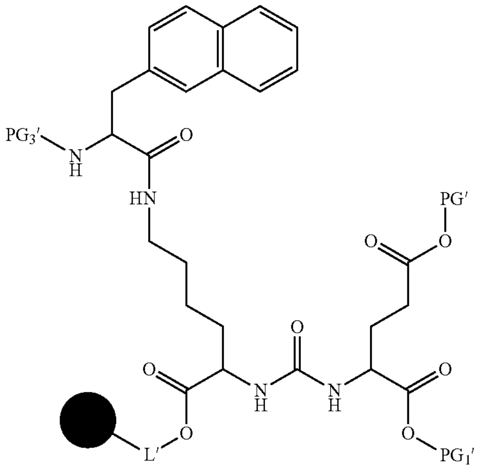

d') contacting the supported compound of formula (VII') with a deprotecting agent to provide a supported, compound of formula (VIII')

(VIII')

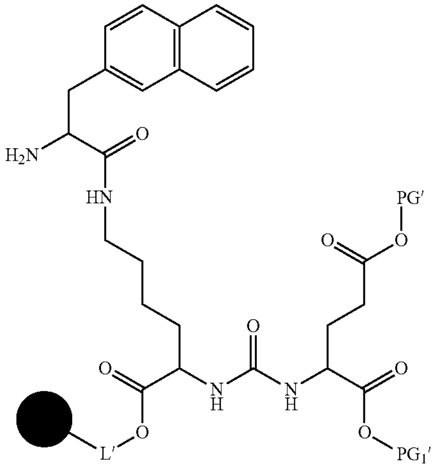

e') contacting the supported, compound of formula (VIII') with a compound of formula (IX')

(IX')

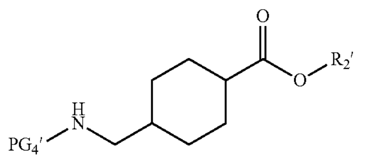

to provide a supported compound of formula (X')

(X')

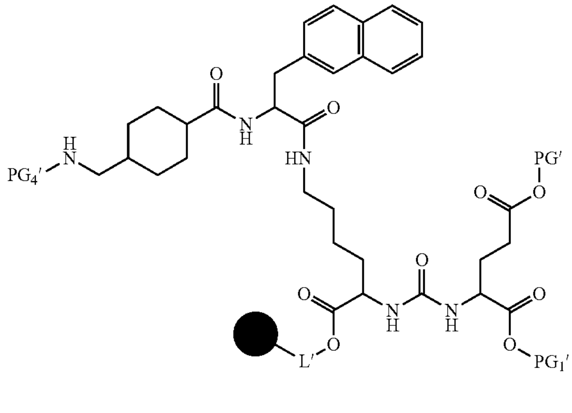

f') contacting the supported compound of formula (X') with a deprotecting agent to provide a supported, compound of formula (XI')

(XI')

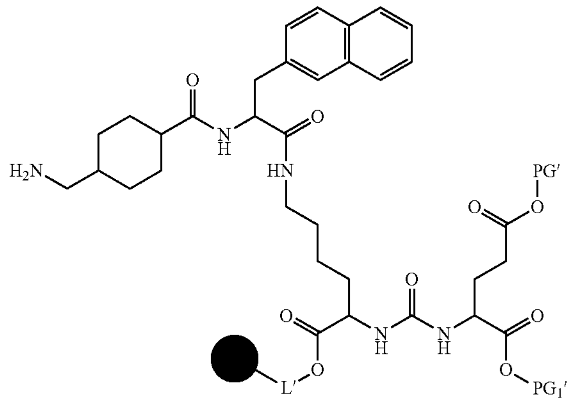

g') contacting the supported, compound of formula (XI') with a compound (XII')

(XII')

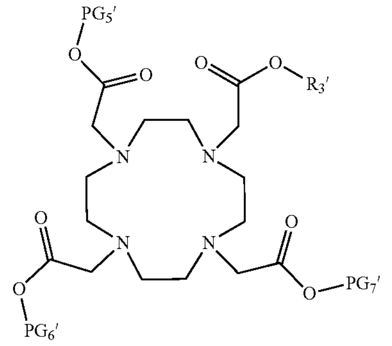

to provide a supported, compound of formula (XIII')

(XIII)

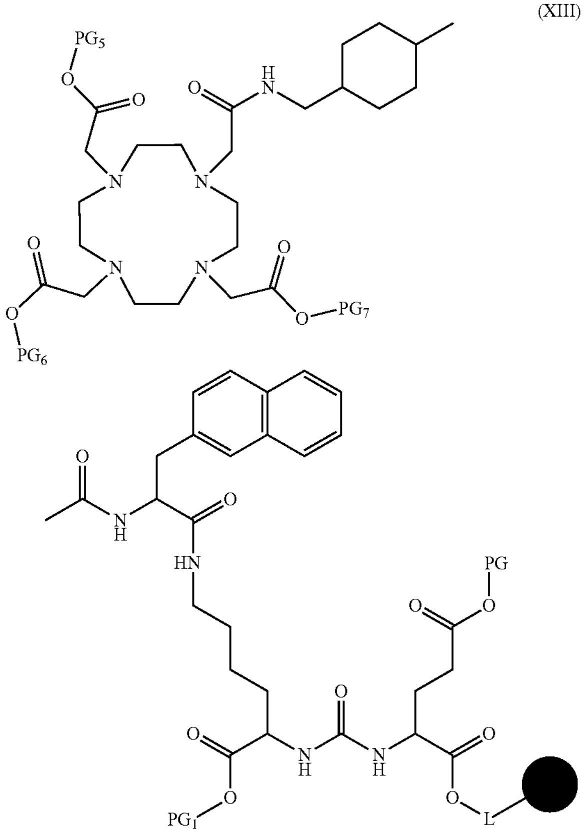

h') contacting the supported compound of formula (XIII') with a cleavage reagent, and optionally with a deprotecting agent, to provide the compound of formula (I), or a pharmaceutically acceptable salt thereof;

wherein

PG', PG1', PG5', PG6' and PG7' are each independently a carboxyl protecting group;

L' is a linker;

PG2', PG3' and PG4' are each independently an amino protecting group;

R1', R2' and R3' are each independently H or an activating ester group, and

LG' is a leaving group selected from the group consisting of imidazole, halogens and activating ester groups.

8. The method according to claim 7, wherein said method comprises all the steps a')-h').

9. The method according to claim 7, wherein PG', PG1', PG5', PG6', and PG7', are independently selected from the group consisting of benzyl, p-methoxybenzyl (PMB), tertiary butyl (t-Bu), methoxymethyl (MOM), methoxyethoxymethyl (MEM), methylthiomethyl (MTM), tetrahydropyranyl (THP), tetrahydrofuranyl (THF), benzyloxymethyl (BOM), trimethylsilyl (TMS), triethylsilyl (TES), t-butyldimethylsilyl (TBDMS), and triphenylmethyl (trityl, Tr).

10. The method according to claim 7, wherein PG2', PG3' and PG4' are independently selected from the group consisting of t-butyloxycarbonyl (Boc), 9-fluorenyl methoxycarbonyl (Fmoc), allyloxycarbonyl (alloc), N-(1-(4,4-dimethyl-2,6-dioxocyclohexylidene)ethyl) (Dde), monomethoxytrityl (MMt), 1-(1-Adamantyl)-1-Methylethoxycarbonyl (Adpoc), N-(1-(4,4-dimethyl-2,6-dioxocyclohex-1-ylidene)-3-methylbutyl) (ivDde) and 4-methyltrityl (Mtt).

11. The method according to claim 7, wherein at least one of the steps a')-h') is performed using a polar aprotic solvent.

12. The method according to claim 7, wherein at least one of the step a'), c'), e') and g') is performed using a coupling agent and/or a base.

* * * * *